(12) United States Patent
Kawakami et al.

(10) Patent No.: US 8,603,647 B2
(45) Date of Patent: *Dec. 10, 2013

(54) ANTHRACENE DERIVATIVE, MATERIAL FOR LIGHT EMITTING ELEMENT, LIGHT EMITTING ELEMENT, LIGHT EMITTING DEVICE, AND ELECTRONIC DEVICE

(75) Inventors: Sachiko Kawakami, Kanagawa (JP); Nobuharu Ohsawa, Kanagawa (JP); Harue Nakashima, Kanagawa (JP); Kumi Kojima, Tokyo (JP); Satoshi Seo, Kanagawa (JP); Masakazu Egawa, Kanagawa (JP); Ryoji Nomura, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/609,956

(22) Filed: Sep. 11, 2012

(65) Prior Publication Data

US 2013/0005067 A1     Jan. 3, 2013

Related U.S. Application Data

(63) Continuation of application No. 13/238,057, filed on Sep. 21, 2011, now Pat. No. 8,298,687, which is a continuation of application No. 11/576,934, filed as application No. PCT/JP2006/306775 on Mar. 24, 2006, now Pat. No. 8,039,122.

(30) Foreign Application Priority Data

| Mar. 28, 2005 | (JP) | 2005-093269 |
| May 27, 2005 | (JP) | 2005-155788 |
| Jun. 27, 2005 | (JP) | 2005-186966 |

(51) Int. Cl.
| H01L 51/54 | (2006.01) |
| H01J 1/63 | (2006.01) |
| C09K 11/06 | (2006.01) |
| C07C 13/58 | (2006.01) |
| C07D 209/86 | (2006.01) |
| C07D 209/88 | (2006.01) |

(52) U.S. Cl.
USPC .............. 428/690; 428/917; 427/58; 427/66; 313/504; 257/40; 585/26; 548/442

(58) Field of Classification Search
None
See application file for complete search history.

(56) References Cited

U.S. PATENT DOCUMENTS

| 5,811,834 A | 9/1998 | Tamano et al. |
| 6,482,986 B1 | 11/2002 | Boigegrain et al. |
| 6,565,996 B2 | 5/2003 | Hatwar et al. |
| 6,617,051 B1 | 9/2003 | Higashi et al. |
| 6,661,023 B2 | 12/2003 | Hoag et al. |
| 6,713,566 B1 | 3/2004 | Marcuccio et al. |
| 6,815,094 B2 | 11/2004 | Lee et al. |
| 6,984,462 B2 | 1/2006 | Kim et al. |
| 7,132,456 B2 | 11/2006 | Gillig et al. |
| 7,161,185 B2 | 1/2007 | Yamazaki et al. |
| 7,173,373 B2 | 2/2007 | Yamada et al. |
| 7,196,466 B2 | 3/2007 | Hieda et al. |
| 7,252,894 B2 | 8/2007 | Yu et al. |
| 7,270,893 B2 | 9/2007 | Fukuda et al. |
| 7,387,845 B2 | 6/2008 | Saitoh et al. |
| 7,541,097 B2 | 6/2009 | Seo et al. |
| 7,597,602 B2 | 10/2009 | Yamada et al. |
| 7,629,060 B2 | 12/2009 | Oshiyama et al. |
| 7,649,197 B2 | 1/2010 | Iwaki et al. |
| 7,651,787 B2 | 1/2010 | Seo et al. |
| 7,704,912 B2 | 4/2010 | Reetz et al. |
| 7,723,722 B2 | 5/2010 | Kawakami et al. |
| 7,745,988 B2 | 6/2010 | Sasaki et al. |
| 7,790,892 B2 | 9/2010 | Ikeda et al. |
| 7,906,224 B2 | 3/2011 | Taka et al. |
| 7,919,773 B2 | 4/2011 | Kawakami et al. |
| 8,039,122 B2 * | 10/2011 | Kawakami et al. ........... 428/690 |
| 8,183,793 B2 | 5/2012 | Egawa et al. |
| 8,298,687 B2 * | 10/2012 | Kawakami et al. ........... 428/690 |
| 2001/0052751 A1 | 12/2001 | Wakimoto et al. |
| 2002/0164415 A1 * | 11/2002 | Van Der Schaft et al. ...... 427/66 |
| 2003/0068524 A1 | 4/2003 | Hatwar |
| 2003/0205696 A1 | 11/2003 | Thoms et al. |
| 2004/0086745 A1 | 5/2004 | Iwakuma et al. |

(Continued)

FOREIGN PATENT DOCUMENTS

| CN | 1526689 A | 9/2004 |
| CN | 1984897 A | 6/2007 |

(Continued)

OTHER PUBLICATIONS

International Search Report (Application No. PCT/JP2006/306775) dated May 2, 2006 (3 pages).
Written Opinion (Application No. PCT/JP2006/306775) dated May 2, 2006 (5 pages).
European Search Report (EP Application No. 06730723) dated Jan. 26, 2010 (6 pages).
Jin-Heng Li et al.; "CuI/Dabco-Catalyzed Cross-Coupling Reactions of Aryl Halides with Arylboronic Acids"; Eur. J. Org. Chem.; 2006; pp. 2063-2066.
Soo-Kang Kim et al.; "Synthesis and Hole-Transporting Properties of Phenyl-Carbazyl Derivatives"; Mol. Cryst. Liq. Cryst., vol. 491; 2008; pp. 133-144.

(Continued)

*Primary Examiner* — Gerard Higgins
*Assistant Examiner* — Andrew K Bohaty
(74) *Attorney, Agent, or Firm* — Fish & Richardson P.C.

(57) ABSTRACT

Disclosed is a composition including an anthracene derivative and a solvent and a method for fabricating a light-emitting element using the composition. The anthracene derivative has a diphenylanthracene moiety and a carbazole moiety linked to one of the phenyl groups of the diphenylanthracene moiety. The use of the composition enables the formation of a light-emitting element by a wet type method such as an ink-jet method, a spin coating method, and a dip coating method.

12 Claims, 33 Drawing Sheets

(56) References Cited

U.S. PATENT DOCUMENTS

| | | |
|---|---|---|
| 2004/0146746 A1 | 7/2004 | Lee et al. |
| 2004/0161632 A1 | 8/2004 | Seo et al. |
| 2004/0161633 A1 | 8/2004 | Seo et al. |
| 2004/0170863 A1 | 9/2004 | Kim et al. |
| 2004/0263069 A1 | 12/2004 | Yamazaki et al. |
| 2005/0031898 A1 | 2/2005 | Li et al. |
| 2005/0058852 A1 | 3/2005 | Tyan et al. |
| 2005/0084711 A1 | 4/2005 | Sasaki et al. |
| 2005/0214565 A1 | 9/2005 | Ikeda et al. |
| 2005/0244670 A1 | 11/2005 | Saitoh et al. |
| 2006/0055305 A1 | 3/2006 | Funahashi et al. |
| 2006/0068221 A1 | 3/2006 | Saitoh et al. |
| 2006/0115680 A1 | 6/2006 | Hwang et al. |
| 2007/0049760 A1 | 3/2007 | Kawakami et al. |
| 2007/0075632 A1 | 4/2007 | Kawakami et al. |
| 2007/0106103 A1 | 5/2007 | Ikeda et al. |
| 2007/0215889 A1 | 9/2007 | Kawakami et al. |
| 2007/0247063 A1 | 10/2007 | Murase et al. |
| 2008/0107918 A1 | 5/2008 | Egawa et al. |
| 2009/0102360 A1 | 4/2009 | Kawakami et al. |
| 2010/0069647 A1 | 3/2010 | Suzuki et al. |
| 2010/0076201 A1 | 3/2010 | Suzuki et al. |
| 2010/0084645 A1 | 4/2010 | Iwaki et al. |
| 2010/0200847 A1 | 8/2010 | Kawakami et al. |

FOREIGN PATENT DOCUMENTS

| | | |
|---|---|---|
| CN | 101200634 A | 6/2008 |
| EP | 0786926 A2 | 7/1997 |
| EP | 1 265 298 A2 | 12/2002 |
| EP | 1496041 A1 | 1/2005 |
| EP | 1515592 A1 | 3/2005 |
| EP | 1 578 175 A1 | 9/2005 |
| EP | 1672048 A1 | 6/2006 |
| EP | 1695952 A1 | 8/2006 |
| EP | 1748045 A1 | 1/2007 |
| EP | 1829871 A1 | 9/2007 |
| JP | 09-268283 A | 10/1997 |
| JP | 11-144876 A | 5/1999 |
| JP | 2003-031371 A | 1/2003 |
| JP | 2003-051388 A | 2/2003 |
| JP | 2003-167550 A | 6/2003 |
| JP | 2003-229273 A | 8/2003 |
| JP | 2003-238534 A | 8/2003 |
| JP | 2003-306454 A | 10/2003 |
| JP | 2004-083513 A | 3/2004 |
| JP | 2004-087363 A | 3/2004 |
| JP | 2004-087396 A | 3/2004 |
| JP | 2004-091334 A | 3/2004 |
| JP | 2004-171828 A | 6/2004 |
| JP | 2004-178895 A | 6/2004 |
| JP | 2004-210786 A | 7/2004 |
| JP | 2004-311415 A | 11/2004 |
| JP | 2005019374 A1 | 3/2005 |
| JP | 2005-170911 A | 6/2005 |
| JP | 2007-131722 A | 5/2007 |
| KR | 20050021888 A | 3/2005 |
| KR | 20050028803 A | 3/2005 |
| WO | 01/23353 A2 | 4/2001 |
| WO | 2004/020388 A1 | 3/2004 |
| WO | 2004/020548 A1 | 3/2004 |
| WO | 2004/075603 A2 | 9/2004 |
| WO | 2004/075604 A2 | 9/2004 |
| WO | 2005/113531 A1 | 12/2005 |
| WO | WO 2006101016 A1 * | 9/2006 |
| WO | 2007/013537 A1 | 2/2007 |

OTHER PUBLICATIONS

Vinich Promarak et al.; "Synthesis and Properties of Stable Amorphous Hole-Transporting Molecules for Electroluminescent Devices"; ScienceDirect, Tetrahedron Letters 47; 2006; pp. 8949-8952.

Roberto Grisorio et al.; "Novel Bifluorene Based Conjugated Systems: Synthesis and Properties"; Tetrahedron 62; 2006; pp. 627-634.

European Search Report (EP Application No. 08003826) dated Jul. 14, 2008 (7 pages).

European Search Report (EP Application No. 09169453) dated Nov. 3, 2009 (4 pages).

International Search Report and Written Opinion (PCT Application No. PCTJP2007066706) dated Oct. 16, 2007 (13 pages).

International Search Report and Written Opinion (PCT Application No. PCTJP2009062568) dated Aug. 11, 2009 (10 pages).

Office Action (PCT Application No. 200680018801.4) dated Apr. 15, 2010 with English translation, 25 pages.

S. Pine ed.; Organic Chemistry; 1987; pp. 744-746.

F. Carey et al.; Advanced Organic Chemistry, Springer, p. 731.

M. Benaglia et al.; "Synthesis of Pyridylstannanes from Halopyridines and Hexamethyldistannane with Catalytic Palladium"; Tetrahedron Letters; 1997; pp. 4737-4740; vol. 38, No. 27.

Z. Li et al.; Synthesis and Functional Properties of End-Dendronized Oligo(9,9-diphenyl)fluorenes; Organic Letters; Mar. 9, 2006, pp. 1499-1502; vol. 8, No. 7.

European Search Report (EP Application No. 12001732.2) dated Jun. 21, 2012 (7 pages).

S. Grigalevicius et al.; "Well defined carbazol-3,9-diyl based oligomers with diphenylamino end-cap as novel 2 amorphous molecular materials for optoelectronics"; J. Photochem. Photobiol. A: Chem. (Journal of Photochemistry and Photobiology A: Chemistry); 2005, pp. 125-129; vol. 174, No. 2.

Korean Office Action (Application No. 2007-7024400), Feb. 28, 2013, 5 pages, with English translation, 3 pages.

Yen-Chun Chen et al.; "High Triplet Energy Polymer as Host for Electrophosphorescence with High Efficiency"; J. Am. Chem. Soc. (Journal of the American Chemical Society); 2006; pp. 8549-8558; vol. 128, No. 26.

L Kurti et al.; Strategic Applications of Named Reactions in Organic Synthesis; Mar. 4, 2005; p. 448; Elsevier Academic Press, Burlington, Massachusetts.

* cited by examiner

ANTHRACENE DERIVATIVE, MATERIAL FOR LIGHT EMITTING ELEMENT, LIGHT EMITTING ELEMENT, LIGHT EMITTING DEVICE, AND ELECTRONIC DEVICE

CROSS-REFERENCE TO RELATED APPLICATIONS

This application is a continuation of U.S. application Ser. No. 13/238,057, filed Sep. 21, 2011, now allowed, which is a continuation of U.S. application Ser. No. 11/576,934, filed Apr. 9, 2007, now U.S. Pat. No. 8,039,122, which is a U.S. National Phase of International Patent Application No. PCT/JP2006/306775 filed Mar. 24, 2006, which claims the benefit of foreign priority applications filed in Japan as Ser. No. 2005-093269 on Mar. 28, 2005, Ser. No. 2005-155788 on May 27, 2005 and Ser. No. 2005-186966 on Jun. 27, 2005, all of which are incorporated by reference.

TECHNICAL FIELD

The present invention relates to a light emitting material. Further, the present invention relates to a light emitting element having a pair of electrodes and a layer containing a light emitting material that can emit light when applied with electric field. Moreover, the present invention relates to a light emitting device having such a light emitting element.

BACKGROUND ART

A light emitting element using a light emitting material has advantages of thinness, lightness in weight, fast response, direct-current low-voltage driving, and so on, and is expected to be applied to a next-generation flat panel display. Further, a light emitting device having light emitting elements arranged in matrix is superior to a conventional liquid crystal display device in a wide viewing angle and high visibility.

A light emitting element has the following light-emission mechanism: voltage is applied to a light emitting layer sandwiched between a pair of electrodes, so that electrons injected from a cathode and holes injected from an anode are recombined in a light-emission center of the light emitting layer to form molecular excitons; thus, light is emitted by releasing energy when the molecular exciton returns to the ground state. As the excited state, a singlet-excited state and a triplet-excited state are known, and the light emission is possible in either of the excited states.

Emission wavelength of a light emitting element is determined by energy difference between a ground state and an excited state, that is, a band gap, of a light emitting molecule included in the light emitting element. Therefore, various emission colors can be obtained by devising structures of the light emitting molecules. By manufacturing a light emitting device using light emitting elements each capable of emitting red light, blue light, and green light, which are the three primary colors of light, a full-color light emitting device can be manufactured.

However, there is a problem in a full-color light emitting device that a light emitting element with excellent color purity can not always be manufactured easily. This is because it is difficult to realize a light emitting element with high reliability and excellent color purity, although light emitting elements for red, blue and green with excellent color purity are needed for manufacturing a light emitting device having superior color reproducibility. As a result of recent development of materials, light emitting elements for red and green with high reliability and excellent color purity have achieved with respect to light emitting elements for red and green. However, as to a light emitting element for blue with high reliability and excellent color purity has not been realized, so many studies have been done (For example, Patent Document 1: Japanese Patent Laid-Open No. 2003-31371).

SUMMARY OF THE INVENTION

The present invention has been made in view of the above-described problem. It is an object of the present invention to provide a novel material capable of realizing excellent color purity of blue, and a light emitting element and a light emitting device using the novel material.

Further, it is an object of the present invention to provide a novel material which is highly reliable, and a light emitting element and a light emitting device using the material.

An anthracene derivative which can be used for solving the above problems simultaneously contains a diphenylanthracene structure and a carbazole skeleton in a molecule as represented by structural formula (1).

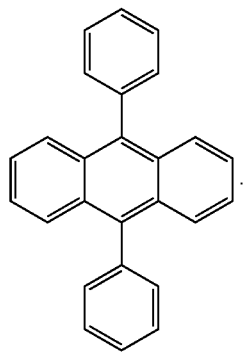

(1)

An anthracene derivative which can be used for solving the above problems has a structure represented by structural formula (1). Further, any one of phenyl groups is substituted by a carbazolyl group, and a nitrogen atom at the 9 position of the carbazolyl group is directly coupled with the phenyl group.

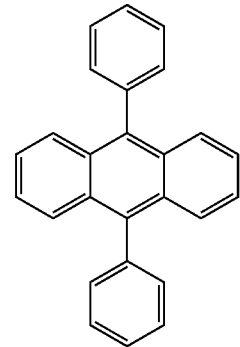

(1)

An anthracene derivative which can be used for solving the above problems has a structure represented by structural formula (1). Further, any one of phenyl groups is substituted by a carbazolyl group which may have a substituent, and a nitrogen atom at the 9 position of the carbazolyl group is directly coupled with the phenyl group.

(1)

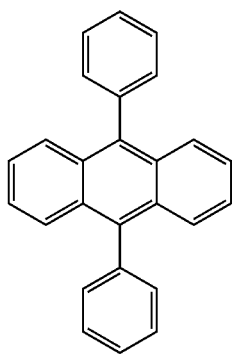

An anthracene derivative which can be used for solving the above problems is represented by general formula (2).

(2)

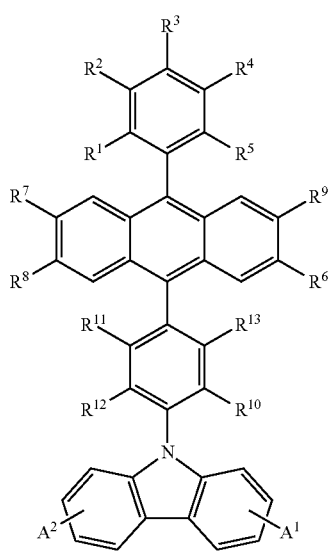

wherein $R^1$ to $R^{13}$ are independently hydrogen, an alkyl group having 1 to 6 carbon atoms, or an aryl group having 6 to 14 carbon atoms, which may have a substituent, and $R^1$ to $R^{13}$ may be the same or different. Further, in the formula, $A^1$ and $A^2$ are independently hydrogen, an alkyl group having 1 to 6 carbon atoms, an aryl group having 6 to 14 carbon atoms, which may have a substituent, or a diarylamino group which may have a substituent, and $A^1$ and $A^2$ may be the same or different.

An anthracene derivative which can be used for solving the above problems is represented by general formula (3).

(3)

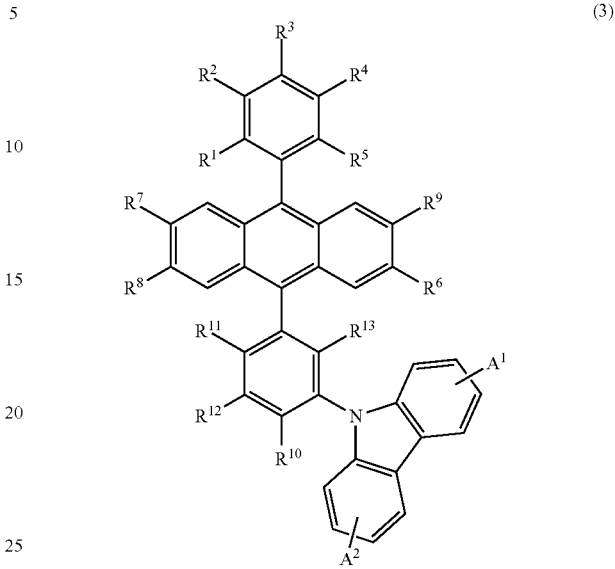

wherein $R^1$ to $R^{13}$ are independently hydrogen, an alkyl group having 1 to 6 carbon atoms, or an aryl group having 6 to 14 carbon atoms, which may have a substituent, and $R^1$ to $R^{13}$ may be the same or different. Further, in the formula, $A^1$ and $A^2$ are independently hydrogen, an alkyl group having 1 to 6 carbon atoms, an aryl group having 6 to 14 carbon atoms, which may have a substituent, or a diarylamino group which may have a substituent, and $A^1$ and $A^2$ may be the same or different.

An anthracene derivative which can be used for solving the above problems is represented by general formula (2).

(2)

wherein $R^1$ to $R^{13}$ are independently hydrogen, an alkyl group having 1 to 6 carbon atoms, or an aryl group having 6 to 14 carbon atoms, which may have a substituent, and $R^1$ to $R^{13}$ may be the same or different. Further, in the formula, $A^1$ and $A^2$ are independently hydrogen, an alkyl group having 1 to 6 carbon atoms, or an aryl group having 6 to 14 carbon atoms, which may have a substituent, and $A^1$ and $A^2$ may be the same or different.

An anthracene derivative which can be used for solving the above problems is represented by general formula (3).

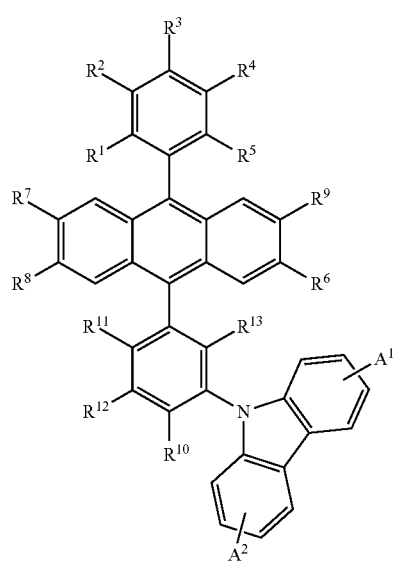

(3)

wherein $R^1$ to $R^{13}$ are independently hydrogen, an alkyl group having 1 to 6 carbon atoms, or an aryl group having 6 to 14 carbon atoms, which may have a substituent, and $R^1$ to $R^{13}$ may be the same or different. Further, in the formula, $A^1$ and $A^2$ are independently hydrogen, an alkyl group having 1 to 6 carbon atoms, or an aryl group having 6 to 14 carbon atoms, which may have a substituent, and $A^1$ and $A^2$ may be the same or different.

An anthracene derivative which can be used for solving the above problems is represented by general formula (2).

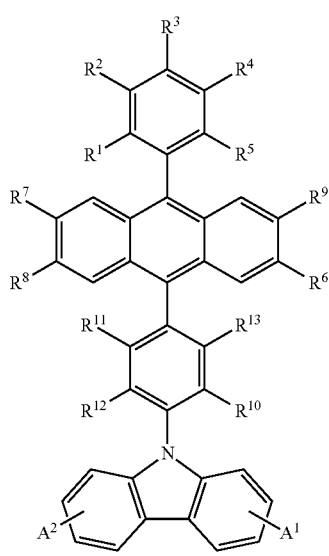

(2)

wherein $R^1$ to $R^{13}$ are independently hydrogen, an alkyl group having 1 to 6 carbon atoms, or an aryl group having 6 to 14 carbon atoms, which may have a substituent, and $R^1$ to $R^{13}$ may be the same or different. Further, in the formula, $A^1$ is a diarylamino group which may have a substituent and $A^2$ is hydrogen or a diarylamino group which may have a substituent.

An anthracene derivative which can be used for solving the above problems is represented by general formula (3).

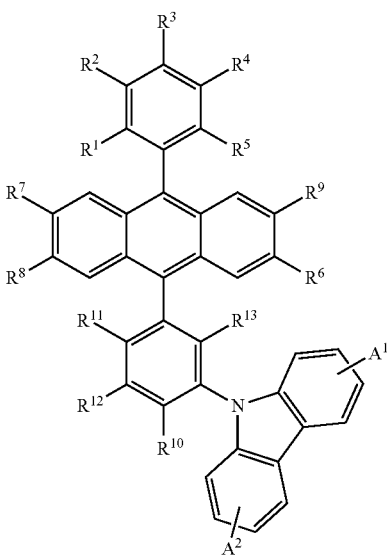

(3)

wherein $R^1$ to $R^{13}$ are independently hydrogen, an alkyl group having 1 to 6 carbon atoms, or an aryl group having 6 to 14 carbon atoms, which may have a substituent, and $R^1$ to $R^{13}$ may be the same or different. Further, in the formula, $A^1$ is a diarylamino group which may have a substituent and $A^2$ is hydrogen or a diarylamino group which may have a substituent.

An anthracene derivative which can be used for solving the above problems is represented by general formula (3).

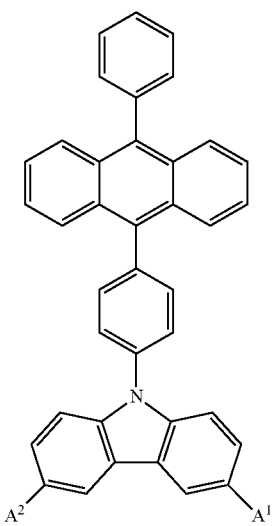

(4)

wherein $A^1$ and $A^2$ are independently hydrogen, an alkyl group having 1 to 6 carbon atoms, or an aryl group having 6 to 14 carbon atoms, which may have a substituent, or a diarylamino group which may have a substituent, and $A^1$ and $A^2$ may be the same or different.

An anthracene derivative which can be used for solving the above problems is represented by general formula (4).

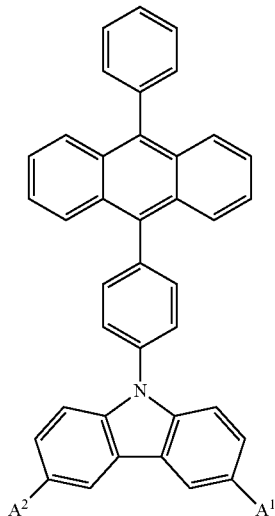

(4)

wherein $A^1$ and $A^2$ are independently hydrogen, an alkyl group having 1 to 6 carbon atoms, or an aryl group having 6 to 14 carbon atoms, which may have a substituent, and $A^1$ and $A^2$ may be the same or different.

An anthracene derivative which can be used for solving the above problems is represented by general formula (4).

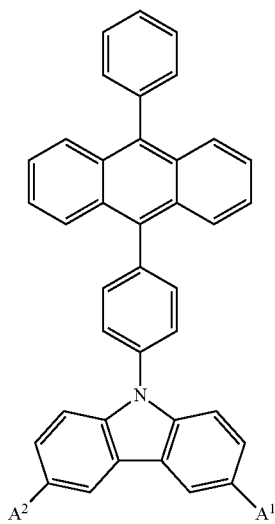

(4)

wherein $A^1$ is a diarylamino group which may have a substituent and $A^2$ is hydrogen or a diarylamino group which may have a substituent.

As to an anthracene derivative which can be used for solving the above problems, the band gap is from 2.7 eV to 3.0 eV.

As to an anthracene derivative which can be used for solving the above problems, the maximum light emission is in the range of 400 nm and 500 nm.

An anthracene derivative which can be used for solving the above problems is represented by structural formula (5).

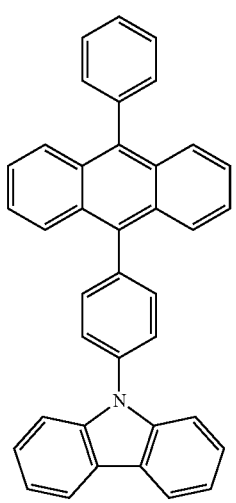

(5)

An anthracene derivative which can be used for solving the above problems is represented by structural formula (6).

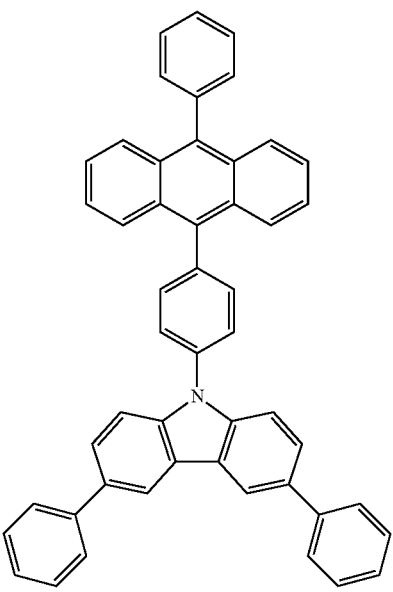

(6)

An anthracene derivative which can be used for solving the above problems is represented by structural formula (7).

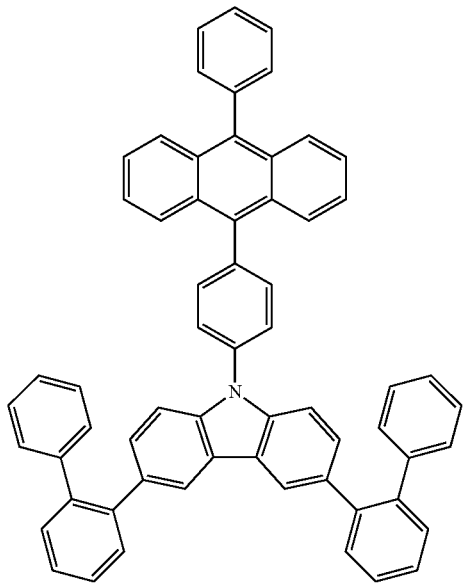

(7)

An anthracene derivative which can be used for solving the above problems is represented by structural formula (8).

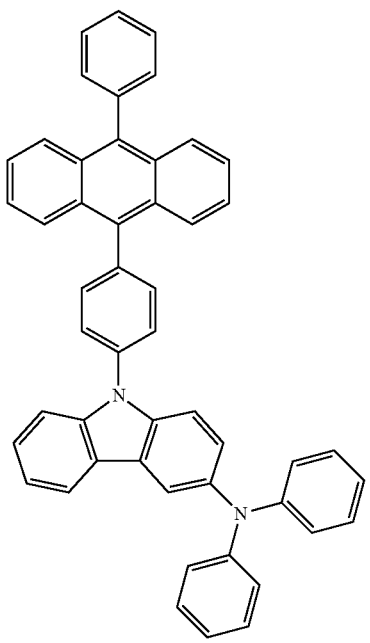

(8)

An anthracene derivative which can be used for solving the above problems is represented by structural formula (9).

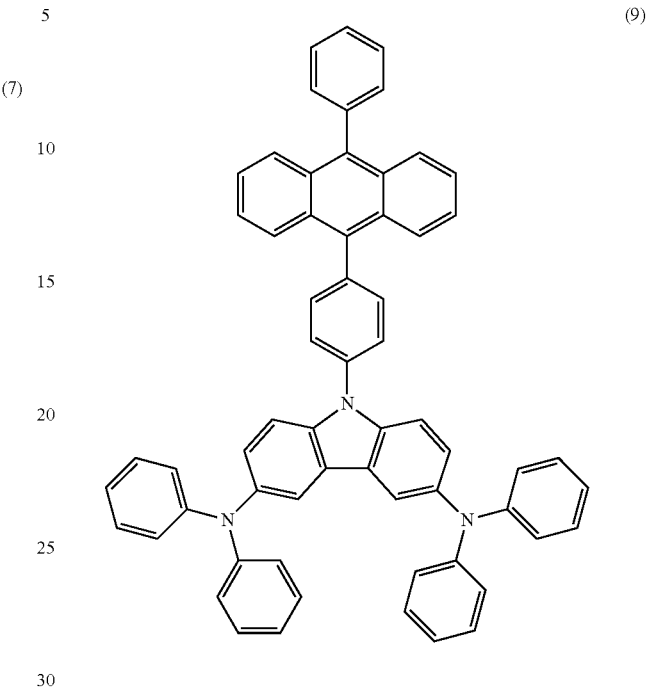

(9)

The structure for solving the above problems in accordance with the present invention is a material for a light emitting element including any one of the anthracene derivatives described above.

The structure for solving the above problems in accordance with the present invention is an organic device including any one of the anthracene derivatives described above.

The structure for solving the above problems in accordance with the present invention is an organic light emitting device including any one of the anthracene derivatives described above.

The structure for solving the above problems in accordance with the present invention is a light emitting element including a first electrode, a second electrode, and a layer containing an organic compound layer between the first electrode and the second electrode. The organic compound layer contains any one of the anthracene derivatives described above.

The structure for solving the above problems in accordance with the present invention is a light emitting device including a light emitting element described above and a device for controlling light emission of the light emitting element.

The structure for solving the above problems in accordance with the present invention is an electronic device including a display area. The display area includes a light emitting element described above and a device for controlling light emission of the light emitting element.

The anthracene derivatives according to the present invention have an extremely large band gap, can emit light with extremely short wavelength, and can emit blue light with good color purity. Further, anthracene derivatives of the present invention has high electrochemical stability.

A light emitting material having a smaller band gap than the anthracene derivatives of the present invention (hereinafter referred to as a dopant) may be added into a layer including the anthracene derivatives of the present invention to obtain light emitted from the dopant. At this time, since the anthracene derivative of the present invention has an extremely large band gap, even if a dopant emitting light of a relatively short wavelength is used, light from the dopant can be obtained efficiently instead of light from the anthracene derivative of the present invention. Specifically, a light emitting material having a maximum emission wavelength around 450 nm can be used as a dopant to provide excellent color purity of blue, and such a material.

Further, anthracene derivatives according to the invention is added into a layer including a material having larger band gap than the anthracene derivative according to the invention (hereinafter referred to as a host) to manufacture a light emitting element; thus, light emitted from the anthracene derivative according to the invention can be obtained. Accordingly, the anthracene derivative according to the invention also functions as a dopant. Hereupon, the anthracene derivative according to the invention has extremely large band gap. and emits light of having short wavelength. Thus, a light emitting element which can provide blue light emission with highly color purity can be manufactured.

Further, as to a light emitting element in which an anthracene derivative having a diarylamine structure according to the invention is used as a dopant, and among anthracene derivatives proposed in the present invention, particularly an anthracene derivative which does not have a diarylamine structure is used as a host, highly electrochemically stable anthracene derivatives of the invention are used for both the host and the dopant. Therefore, a highly reliable light emitting element can be obtained.

Further, using a light emitting material containing the above-described anthracene derivative according to the invention, a light emitting element providing excellent color purity of blue color can be obtained. Still further, a light emitting material containing the above-described anthracene derivative according to the invention is used; thus, a light emitting material with extremely high reliability can be obtained.

A light emitting element according to the invention including the anthracene derivative can provide excellent color purity of blue color. In addition, a light emitting element according to the invention including the anthracene derivative is highly reliable.

A light emitting device having a light emitting element according to the invention is a light emitting device with high color reproducibility. Further, it is a light emitting element with high display quality. In addition, light emitting device having a light emitting element according to the invention is a highly reliable light emitting device.

An electronic device including the above light emitting element according to the invention is an electronic device with high color reproducibility. In addition, it is an electronic device with high display quality. Furthermore, an electronic device having the light emitting element according to the invention is an electronic device with high reliability.

BEST MODE FOR CARRYING OUT THE INVENTION

Figure 1:
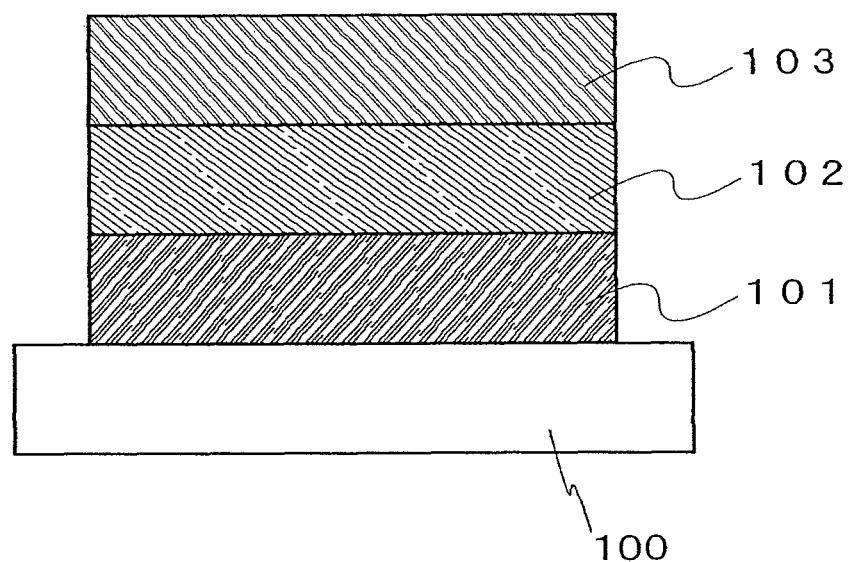
FIG. 1 is a figure showing a light emitting element of the present invention.

Embodiments and Examples according to the present invention will be hereinafter described with reference to the accompanying drawings. The present invention is not limited to the following description. The present invention can be carried out in many different modes, and it is easily understood by those skilled in the art that modes and details disclosed herein can be modified in various ways without departing from the spirit and the scope of the present invention. It should be noted that the present invention should not be interpreted as being limited to the description of the embodiments and examples below.

Embodiment 1

Anthracene derivatives of the present invention will be described in this embodiment.

It is a feature of an anthracene derivative of the present invention that the anthracene derivative has diphenylanthracene structure and a carbazole group in each molecule as shown in the following general formulae (2) to (4). That is based on the reason below.

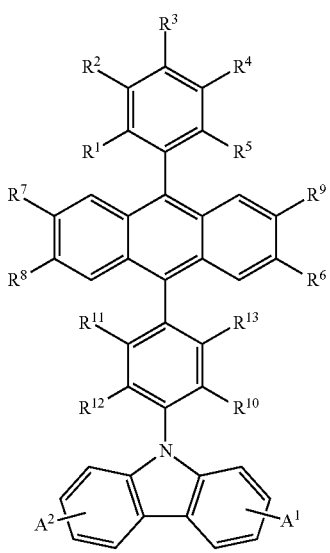

(2)

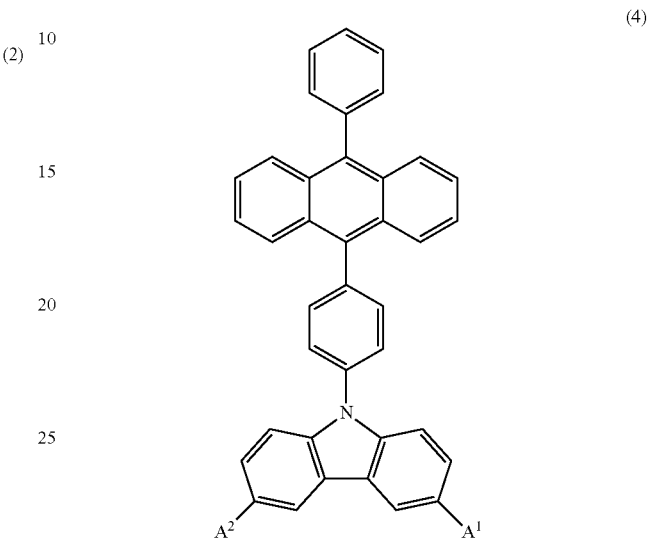

(4)

wherein R1 to R10 each independently represent hydrogen, an alkyl group having 1 to 6 carbon atoms, or an aryl group having 6 to 14 carbon atoms which may be substituted or unsubstituted, each of which may be the same or different. Further, A1 represents a diarylamino group which may be substituted or unsubstituted. A2 represents hydrogen or a diarylamino group which may be substituted or unsubstituted.

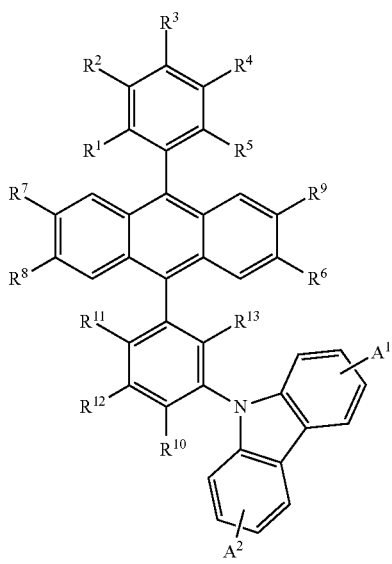

(3)

wherein R1 to R10 each independently represent hydrogen, an alkyl group having 1 to 6 carbon atoms, or an aryl group having 6 to 14 carbon atoms which may be substituted or unsubstituted, each of which may be the same or different. Further, A1 represents a diarylamino group which may be substituted or unsubstituted. A2 represents hydrogen or a diarylamino group which may be substituted or unsubstituted.

wherein A1 and A2 each independently represent hydrogen, an alkyl group having 1 to 6 carbon atoms, an aryl group having 6 to 14 carbon atoms which may be substituted or unsubstituted, or a diarylamino group which may be substituted or unsubstituted, each of which may be the same or different.

A blue color light emitting material generally has low reliability, and blue color light emitting materials known as relatively reliable ones are poor in color purity, so that blue color emission with high purity can not be obtained. It can be considered this is because electrochemical stability and stability of the excited state of a blue color material are low. In other word, high electrochemical stability and stability of the excited state are essential for a highly reliable material for blue color. Furthermore, taking into account that a light emitting element and a light emitting device having a light emitting element are used under various external environments, stability at high temperature is also required in particular.

An anthracene derivative is known as a compound capable of blue light emission; however, anthracene itself tends to form excimer in a solid state; accordingly, efficient light emission can not be obtained even when anthracene itself is used for a light emitting element. Further, chromaticity is reduced. Accordingly, introduction of bulky substituent is required to prevent the formation of excimer. In particular, it is an advantageous method to introduce a substituent into 9 and 10 positions that are most reactive. Further, in order to keep the high carrier transporting property of an anthracene skeleton, it is particularly effective to introduce an aryl group.

The present inventors found that a phenyl group is particularly effective as a substituent introduced into the 9 and 10 positions of anthracene, and the stability of the excited state can be greatly increased compared with a condensed aromatic group such as a naphthyl group. Accordingly, an anthracene derivative of the invention includes an anthracene skeleton into which a phenyl group is introduced into 9 and 10 positions as a substituent shown in the above general formulae (2)

to (4), that is, a diphenylanthracene skeleton as represented by the structural formula (1) below.

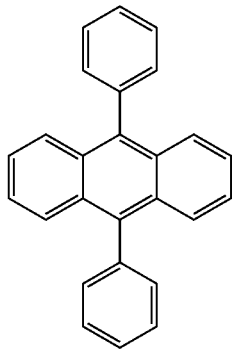

(1)

Meanwhile, a carbazolyl group represented by the structural formula (10) has a structure in which phenyl groups of diphenylamine are bridged, so that it has high thermal stability. Accordingly, by introducing a carbazolyl group, thermal stability (glass transition temperature or melting point) of a compound can be improved. Further, the present inventors revealed that electrochemical stability is increased greater in the case of using a compound in which one carbazolyl group is introduced, for example, a compound in which a carbazolyl group is introduced into only one of phenyl groups in diphenylanthracene, than the case of using a compound in which two carbazolyl groups are introduced in both the phenyl groups in diphenylanthracene.

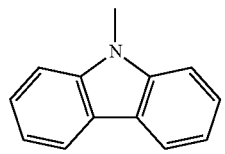

(10)

On the other hand, the inventors revealed that the electrochemical stability is greatly improved by introducing a carbazolyl group to only one phenyl group. Therefore, it is a feature of the present invention that an anthracene derivative of the invention has one diphenylanthracene skeleton as well as one carbazolyl group as shown in the general formulae (2) to (4). In addition, the carbazolyl group preferably has a structure in which a nitrogen atom at the 9 position is directly coupled with the phenyl group.

An anthracene derivative according to the invention having the above-described structure has an extremely large band gap; thus, blue light emission with high color purity can be obtained. Further, the anthracene derivative according to the invention has high electrochemical stability. Further, the anthracene derivative according to the invention has high thermal stability. Further, the anthracene derivative according to the invention has an extremely large band gap; accordingly, when it is used as a host in a light emitting layer of a light emitting element, blue light emission with high color purity can be obtained. Further, the anthracene derivative according to the invention has an extremely large band gap; accordingly, when it is used as a dopant in a light emitting layer of a light emitting element, blue light emission with high color purity can be obtained. A light emitting element using an anthracene derivative according to the invention can be highly reliable. Especially, when an anthracene derivative according to the invention is used as both a host and a dopant in a light emitting layer in a light emitting element, a light emitting element with extremely high reliability can be obtained.

In an anthracene derivative disclosed in the present invention, an aryl group or an alkyl group may be contained in an anthracene skeleton or a phenyl group directly coupled with the anthracene skeleton. That is based on the reason below.

In an organic light emitting element, crystallization of a material causes capital damage to an element. Specifically, it may be an immediate cause of a short circuit between electrodes, which inhibits light emission. Therefore, the crystallinity of a material is required to be lowered. Correspondingly, it is effective to introduce an appropriate substituent into an anthracene skeleton or a phenyl group directly coupled with the anthracene skeleton. An alkyl group or an aryl group can be used as such a substituent.

An alkyl group or an aryl group to be introduced is not limited; however, a phenyl group, an o-biphenyl group, or the like is preferable as the aryl group, and a methyl group a t-butyl group, or the like is preferable as the alkyl group.

An alkyl group has an extremely great effect of suppressing crystallization, and it can suppress crystallization of a structure of which crystallization can not be suppressed by introducing an aryl group. Note that introduction of an alkyl group may reduce carrier transporting property; therefore, in the case where the crystallinity of the material into which a substituent is to be introduced is not so high, an aryl group is more effective as the substituent to be introduced in terms of keeping the carrier transporting property.

Further, in an anthracene derivative disclosed in the present invention, a diarylamino group may be introduced into a carbazolyl group. This is particularly effective when the anthracene derivative is used as a light emitting material for a dopant. That is based on the reason below.

In general, in an organic light emitting element having high efficiency, a light emitting layer is provided between a hole transporting material and an electron transporting material. The light emitting region is on either an electron transporting material side or a hole transporting material side of the light emitting region. Hereupon, when the band gap of an electron transporting material or a hole transporting material is small, and the tight-emission wavelength is shorter than the light-emission wavelength of the light emitting layer, a part of or all of the excitation energy of the light emitting material formed in the light emitting layer is moved to a transporting layer. Accordingly, light emission from the light emitting layer can not be obtained, or light emission of a transporting material is mixed in the light emission from the light emitting layer, which causes reduction in color purity and light emission efficiency.

As to a hole transporting material a compound having a large band gap and short light emission wavelength is known, and there are many materials which are highly reliable even in the case of being applied to a light emitting element. On the other hand, as to an electron transporting material, although some reliable materials are known, they generally have small band gap. Therefore, in the case of manufacturing a light emitting element which emits light especially in a short wavelength region, when the light emission region is on the electron transporting region side, light in a long wavelength region is easily emitted. In order to obtain short wavelength light emission, the light emission region is preferably arranged close to the hole transporting material.

Accordingly, the light emitting layer preferably has an electron transporting property, so that an anthracene skeleton having an appropriate electron transporting property is suitable. However, since the anthracene skeleton also has a hole transporting property, the light-emission region is relatively difficult to be limited. Therefore, the light emitting layer is preferably doped with a small amount of a light emitting material having a high hole transporting property, which can trap holes. Accordingly, an element structure in which an electron transporting material based on an anthracene skeleton is used as a host compound, and a dopant which can trap holes and has high light emission quantum yields is added is most suitable.

Considering the above, the dopant is required to have a hole transporting property and have a positively high HOMO level as compared with the host of the light emitting layer. A structure satisfying such requirements is an arylamine structure. Further, as a skeleton having extremely high light emission efficiency, a diphenylanthracene skeleton is suitable.

Note that an anthracene derivative according to the invention into which an arylamine structure is introduced tends to have a smaller band gap, compared with the anthracene derivative according to the invention into which an arylamine structure is not introduced. Therefore, a preferable light emitting layer of a light emitting element can be manufactured by using the anthracene derivative according to the invention into which an arylamine structure is introduced as a dopant and the anthracene derivative according to the invention into which an arylamine structure is not introduced as a host.

For the above reason, an anthracene derivative according to the invention preferably has a carbazolyl group into which an acylamino group is introduced. Using the compound, since light emission from an anthracene skeleton can be obtained, a blue color light emission with good color purity can be obtained.

Further, such an anthracene derivative having a band gap of 2.7 eV or more and 3.0 eV or less or an anthracene derivative having the maximum emission wavelength (peak in the emission spectrum) in the range of 400 nm and 500 nm displays good chromaticity of blue color so that it is suitably used as the dopant.

Based on the above-described design guideline, typical examples of anthracene derivatives according to the invention which are represented by the above general formulae (2) to (4) are shown in the structural formulae (11) to (120). The present invention is not limited to those.

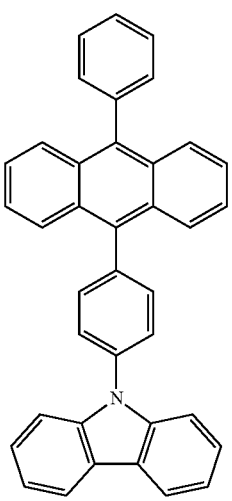

(11)

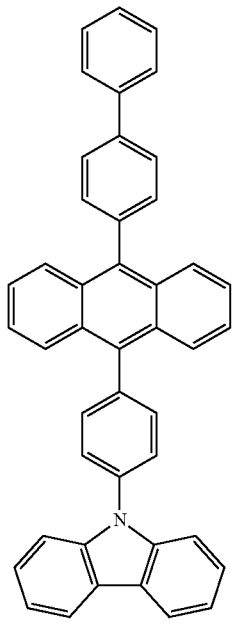

(12)

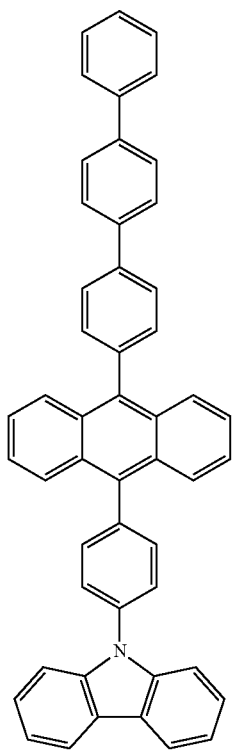

(13)

(14)
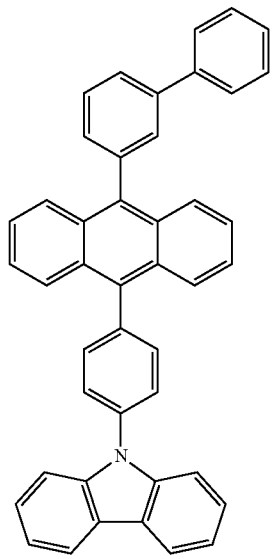
(15)
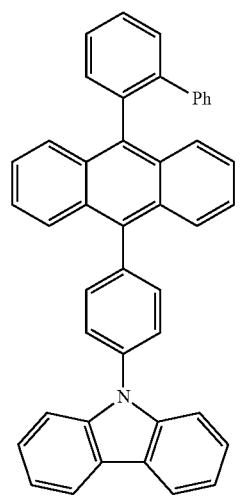
(16)
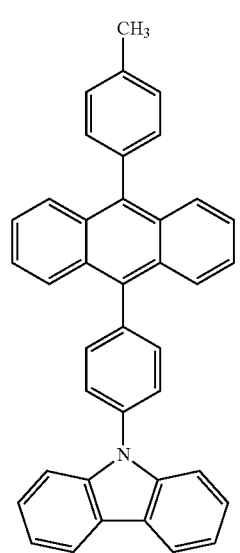
(17)
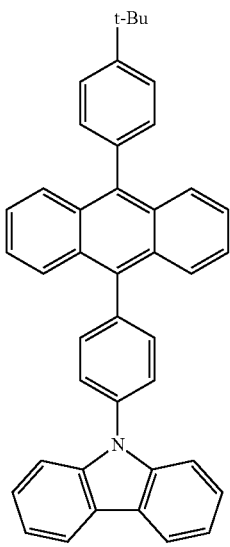
(18)
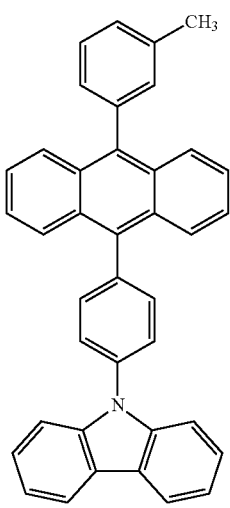
(19)
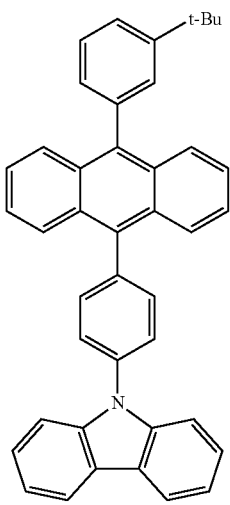

(20)
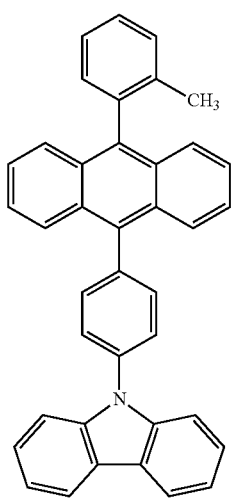
(21)
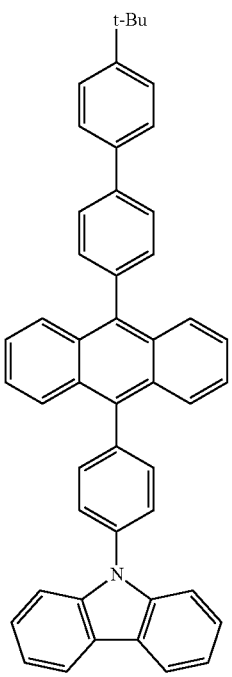
(22)
(23)
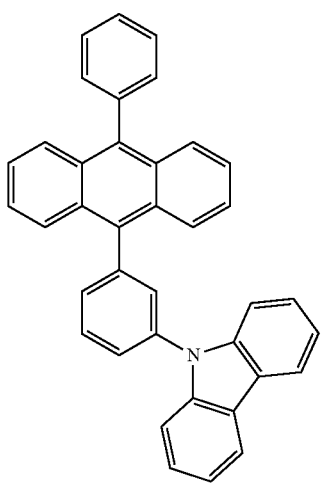

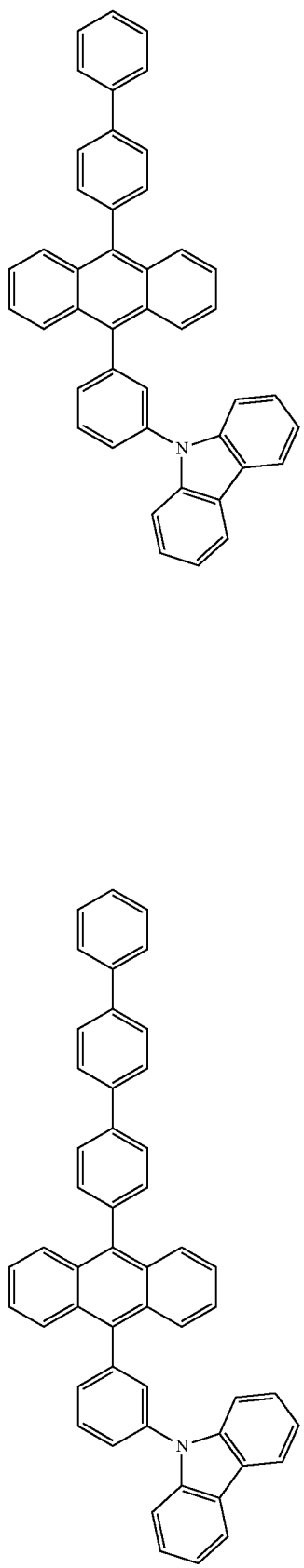
(24)
(25)
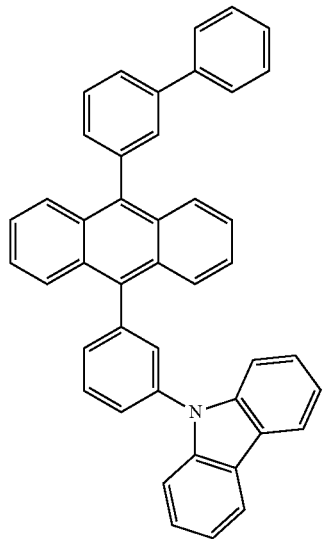
(26)
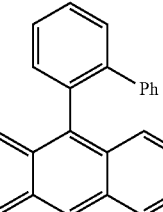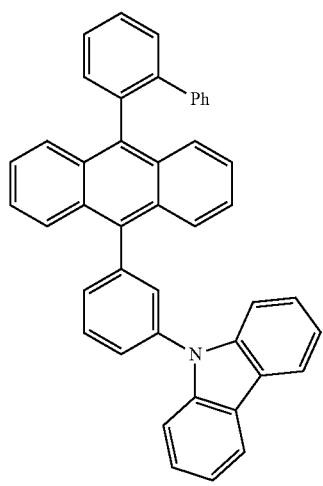
(27)
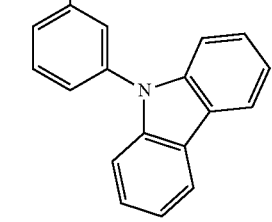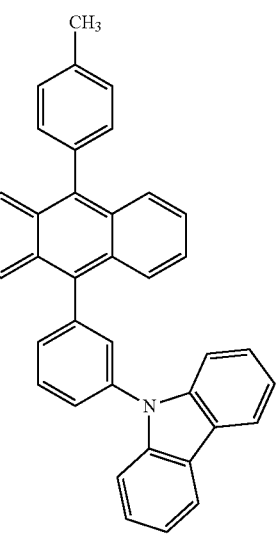
(28)

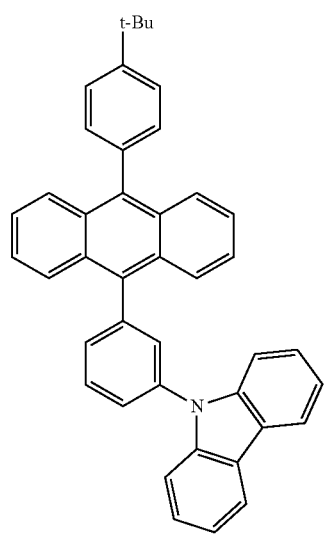
(29)
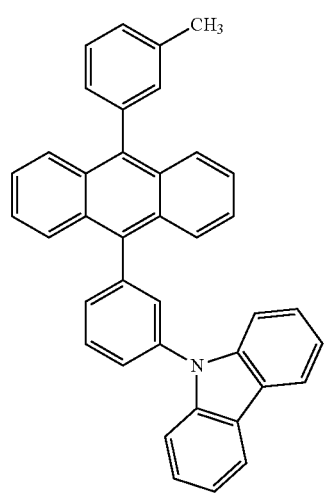
(30)
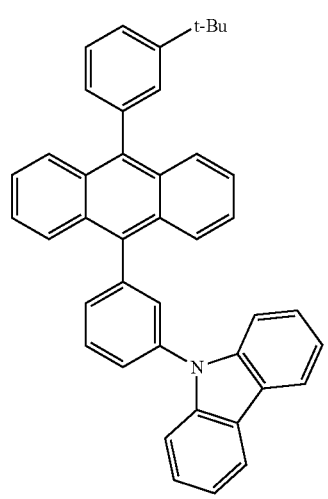
(31)
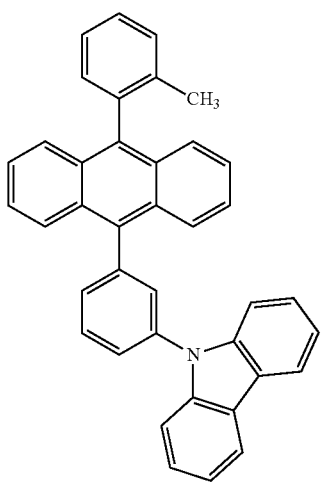
(32)
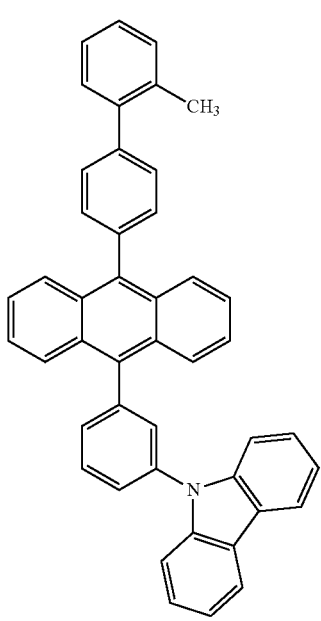
(33)

27
-continued
(34)
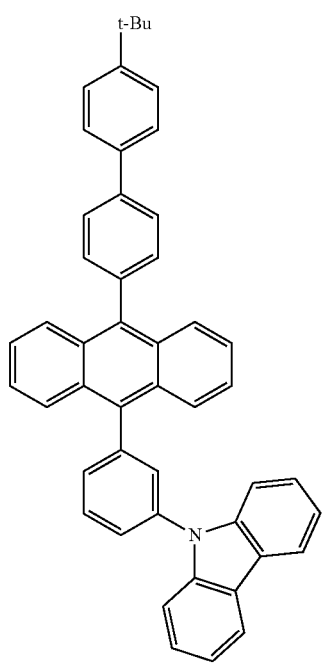
(35)
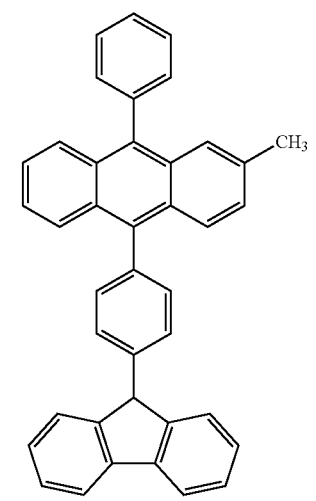
(36)
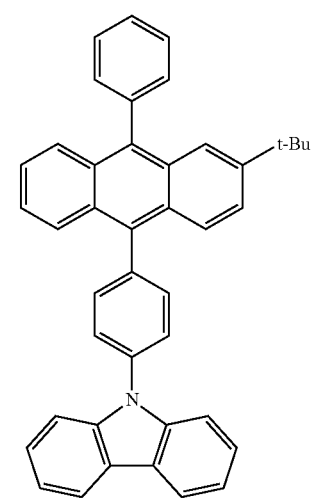
28
-continued
(37)
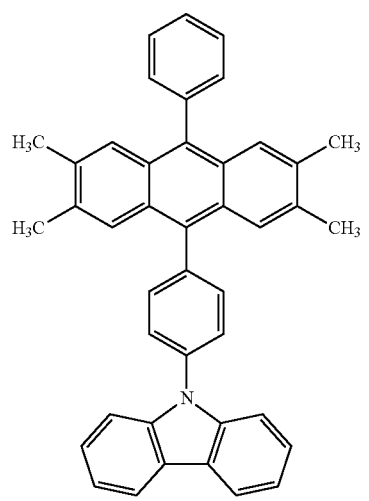
(38)
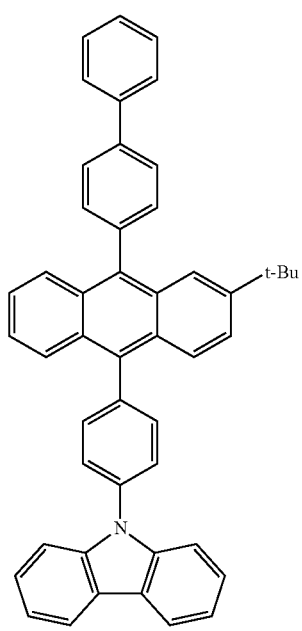
(39)
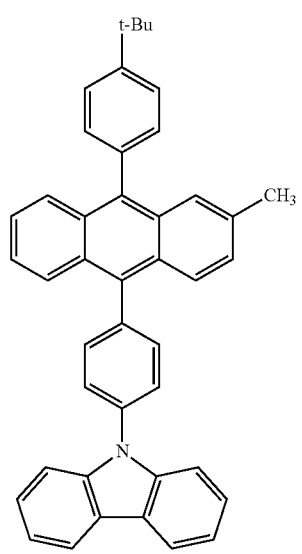

(40)
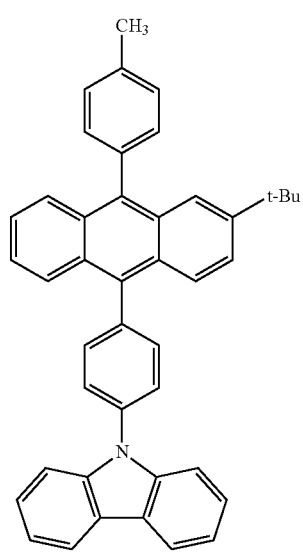
(41)
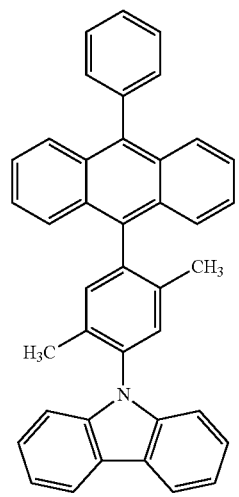
(42)
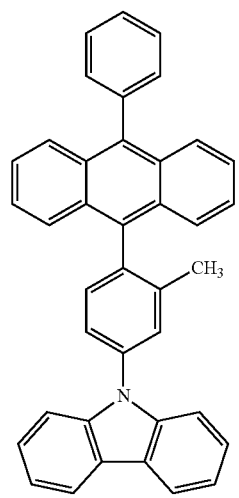
(43)
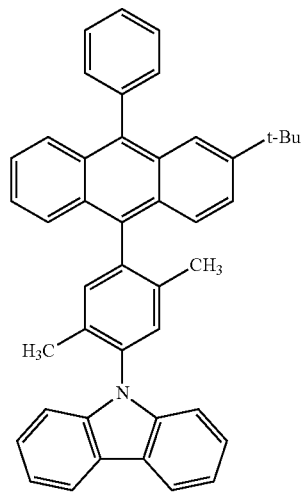
(44)
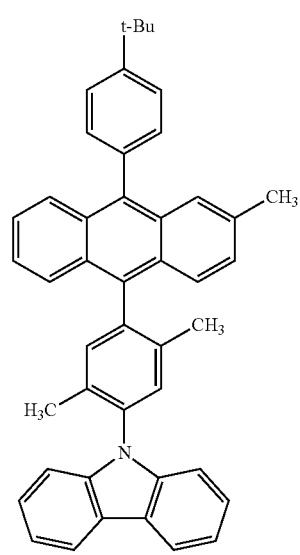
(45)
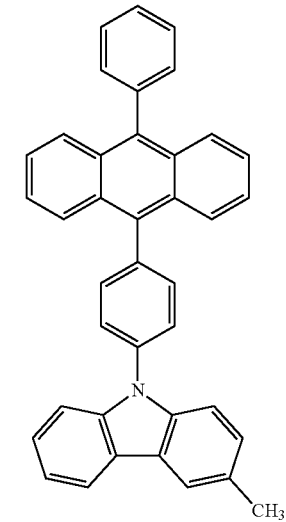

(46)
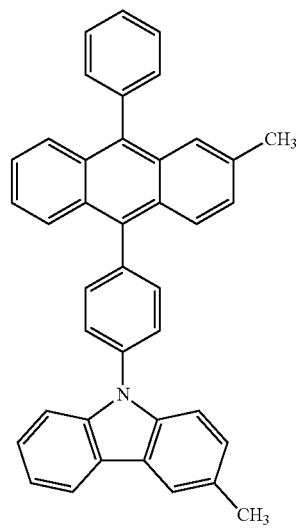
(47)
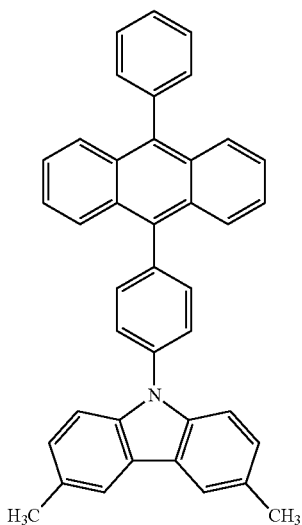
(48)
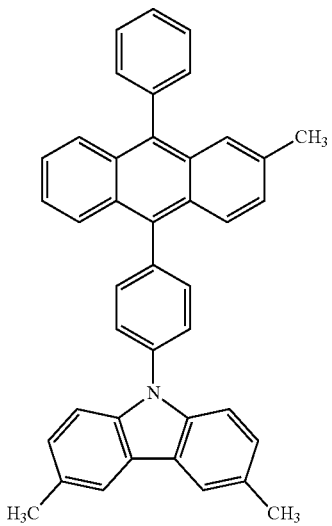
(49)
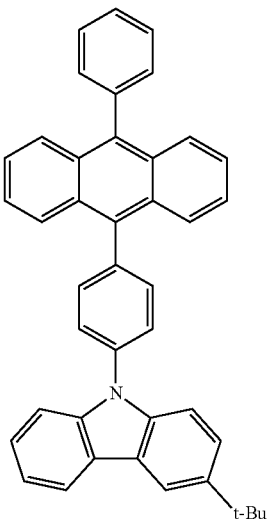
(50)
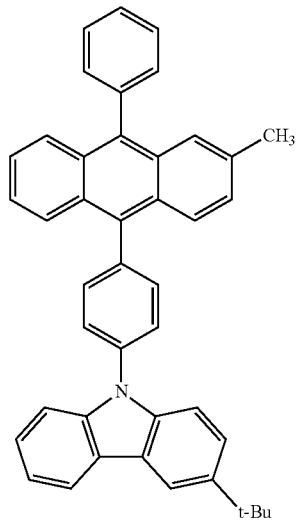
(51)
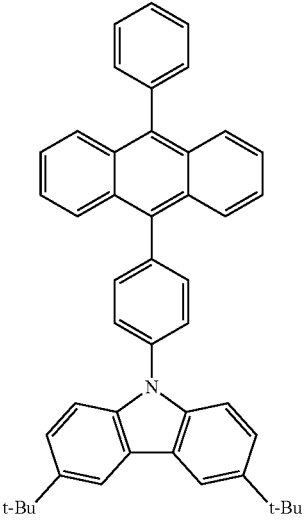

(52)
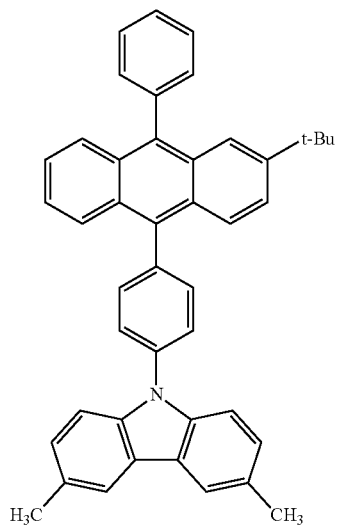
(53)
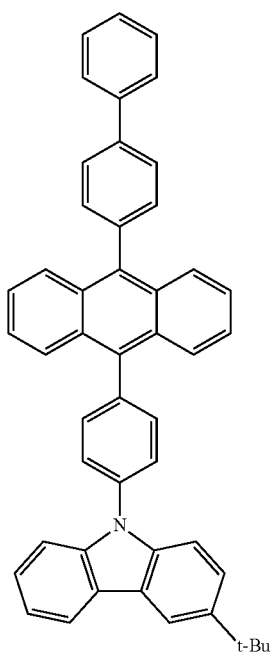
(54)
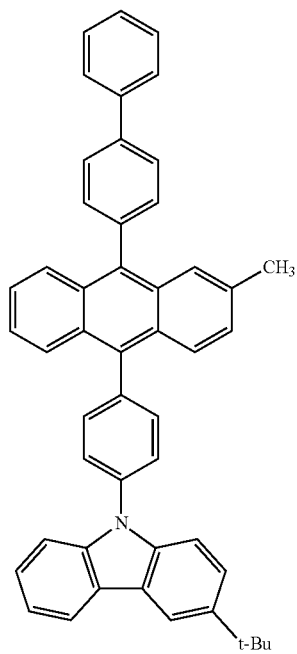
(55)
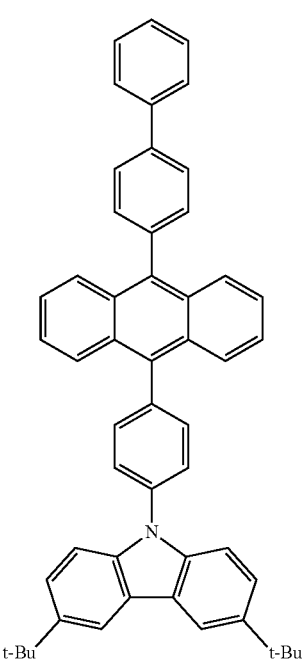

(56)
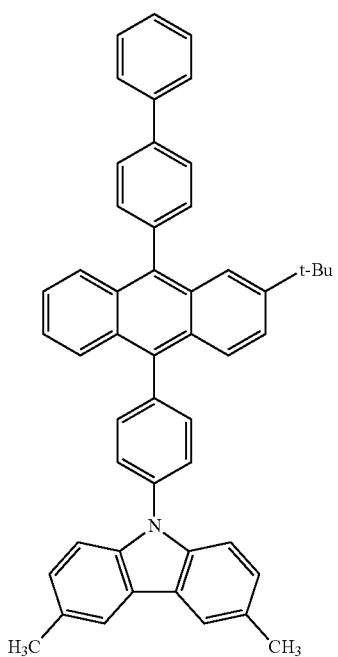
(58)
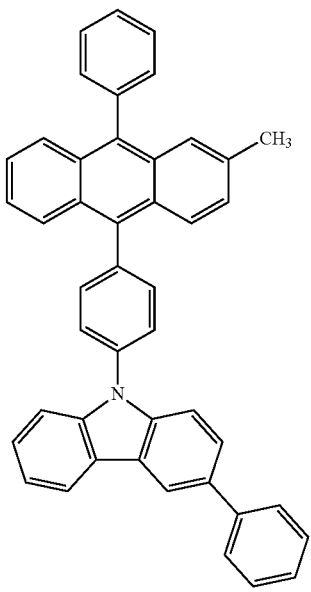
(57)
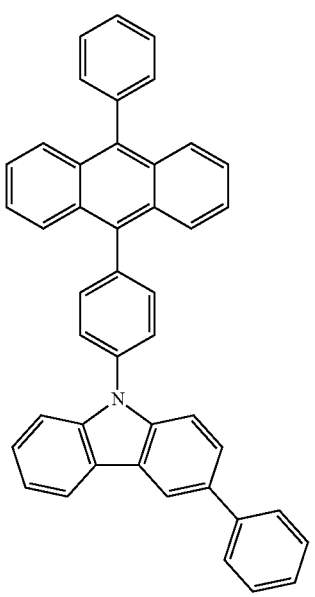
(59)
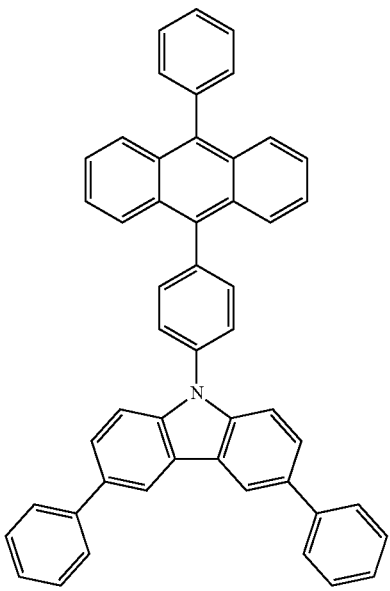

(60)
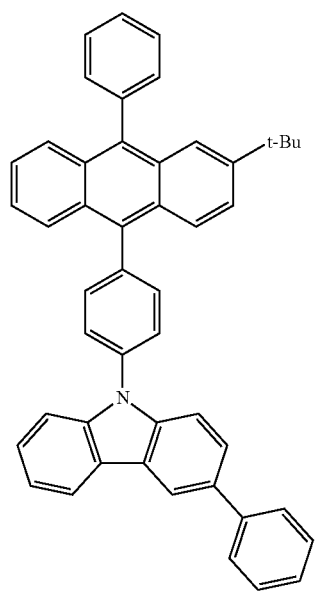
(61)
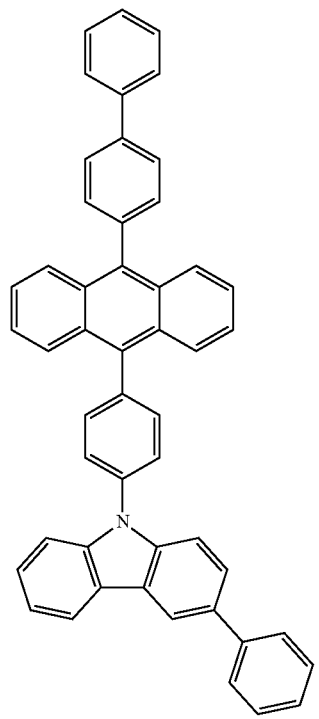
(62)
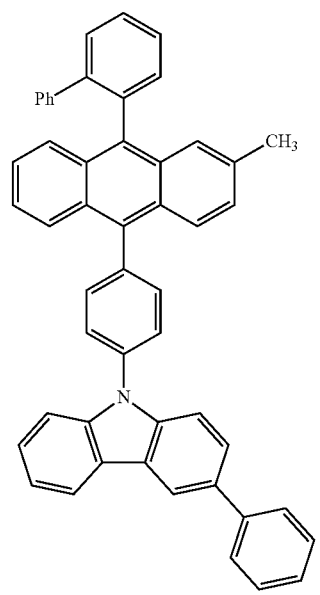
(63)
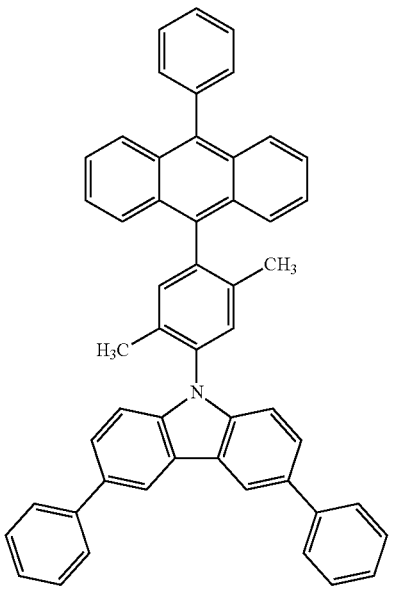

(64)
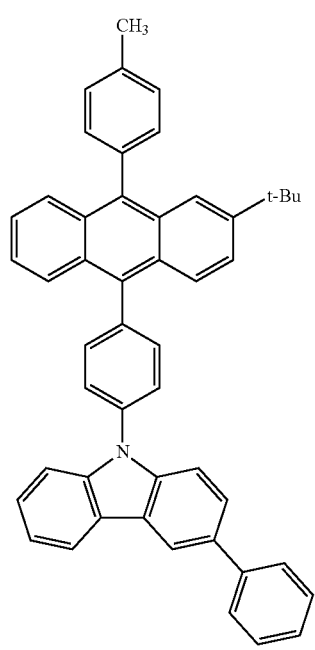
(66)
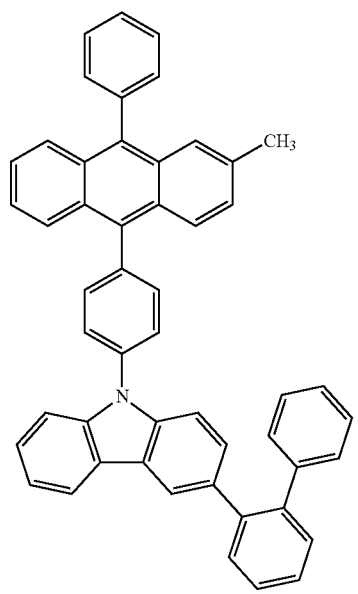
(65)
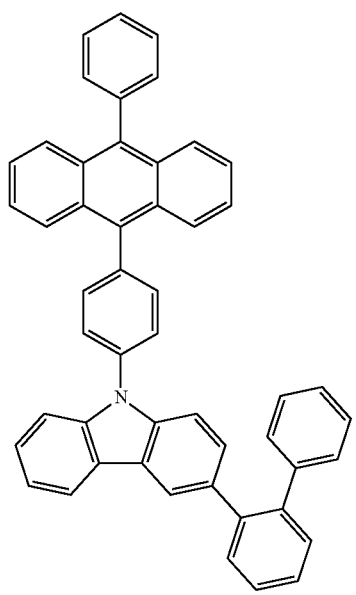
(67)
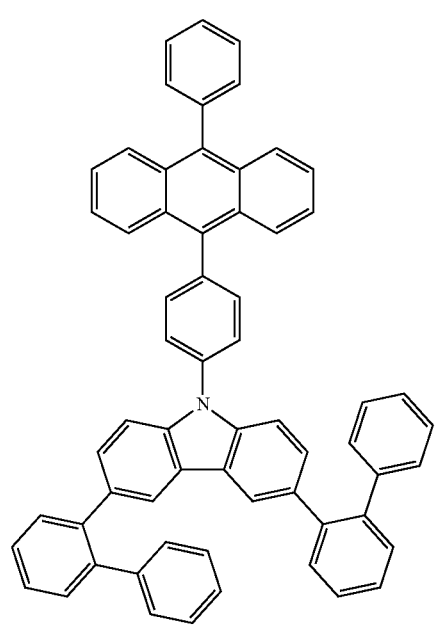

(68)
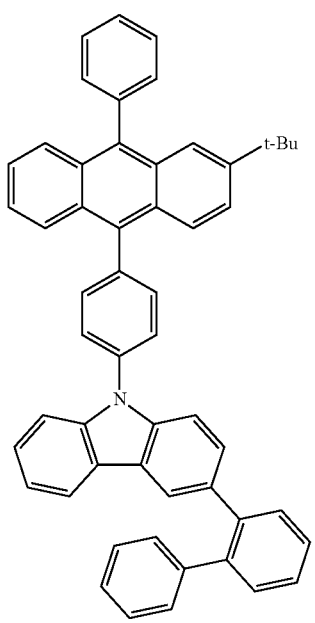
(69)
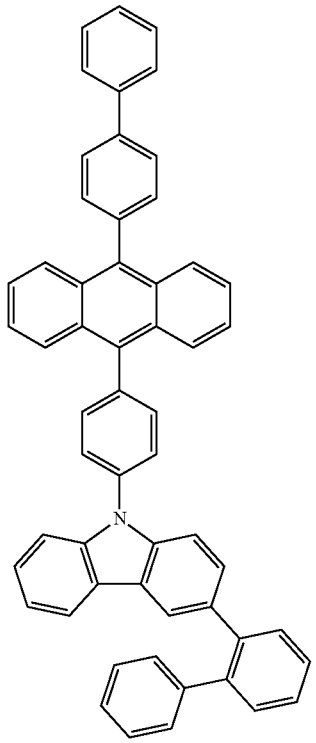
(70)
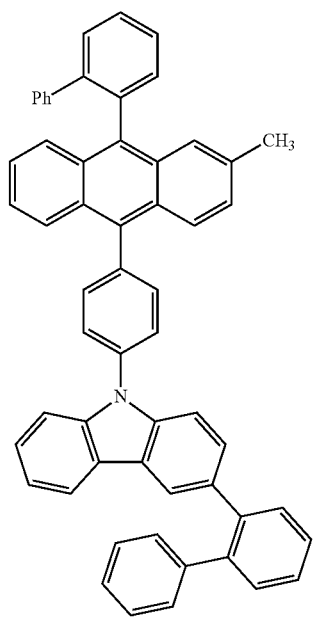
(71)
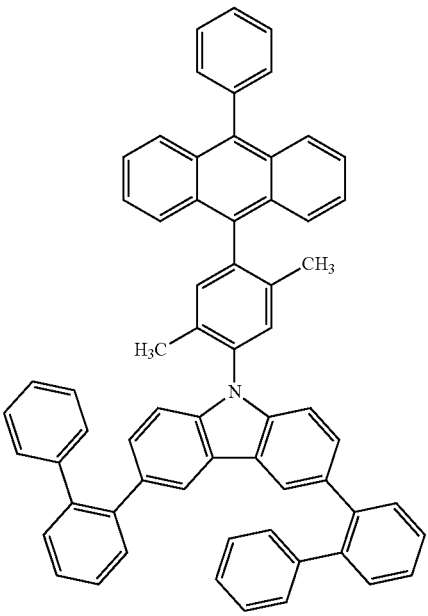

(72)
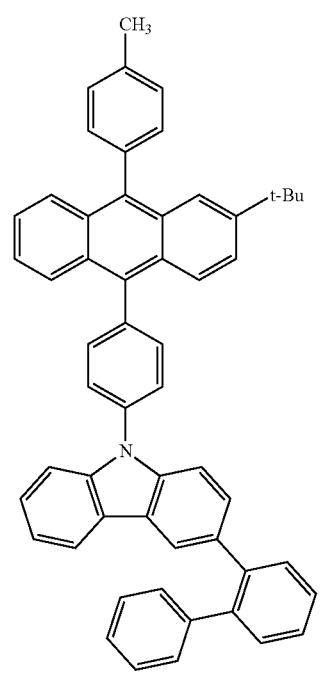
(73)
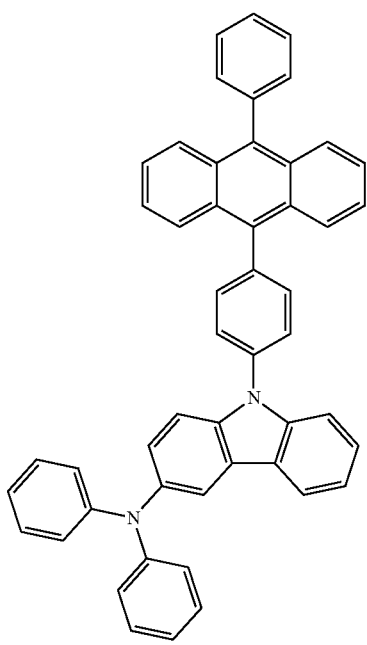
(74)
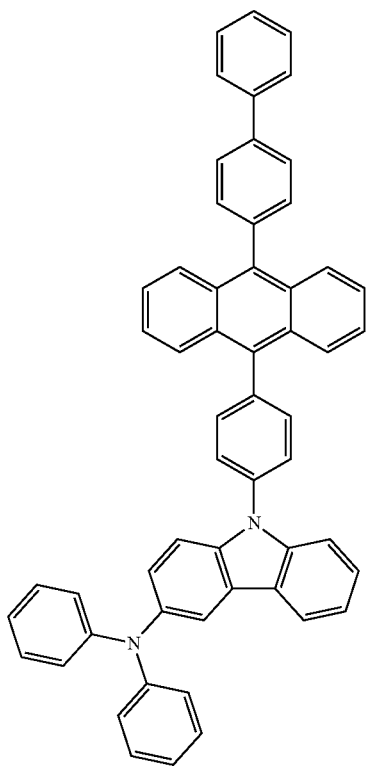
(75)
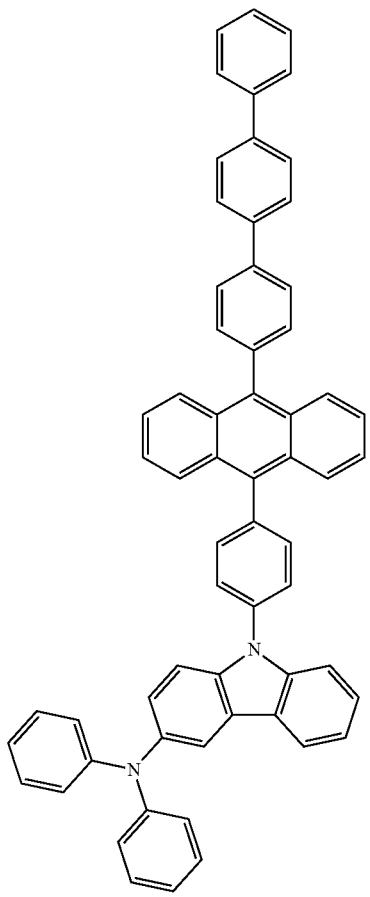

(76)
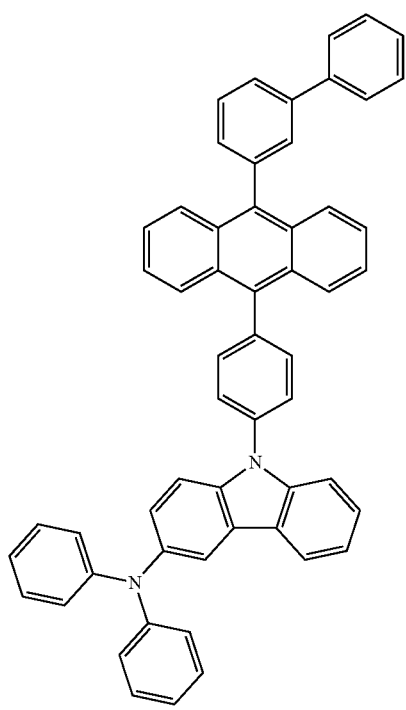
(77)
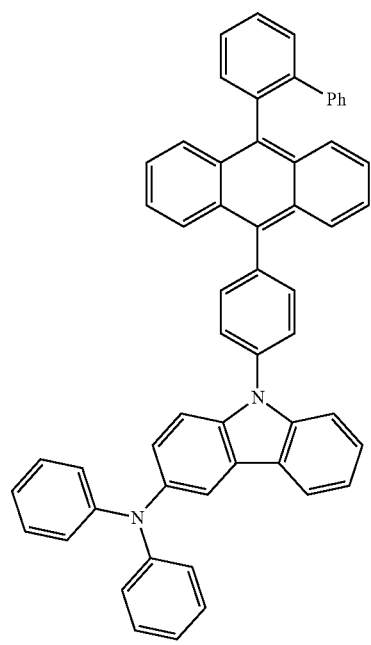
(78)
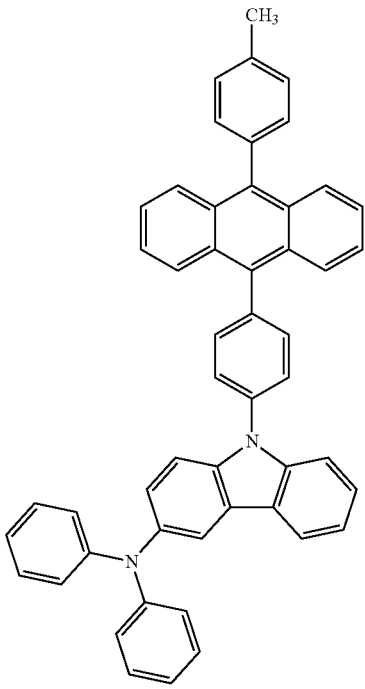
(79)
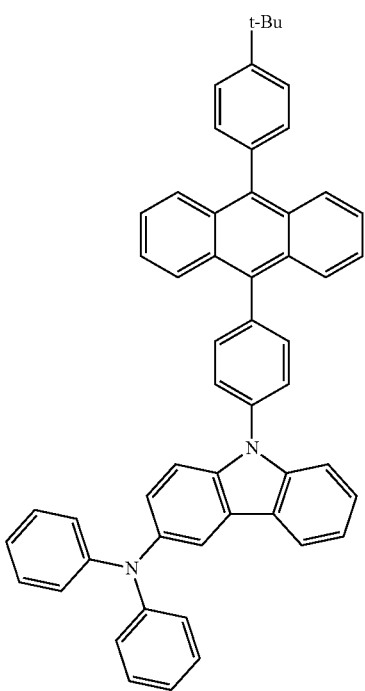

(80)
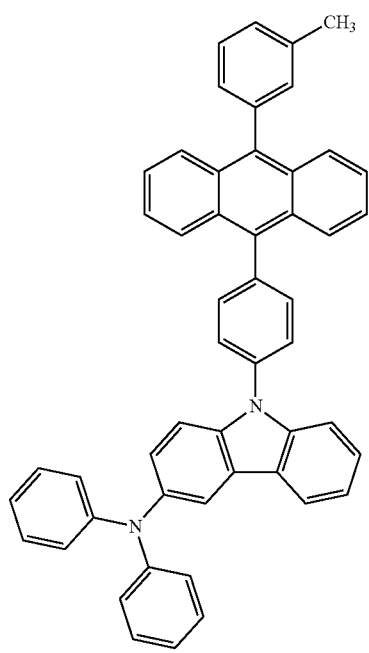
(81)
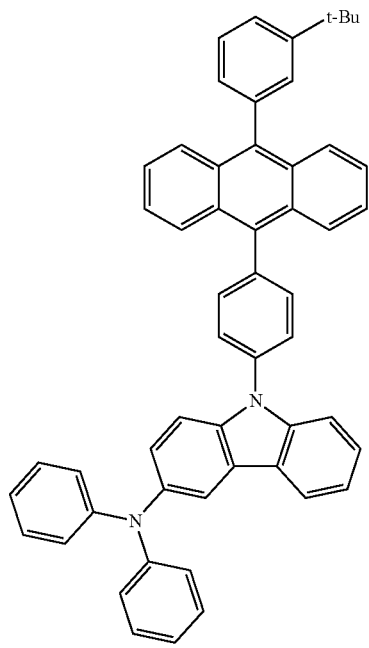
(82)
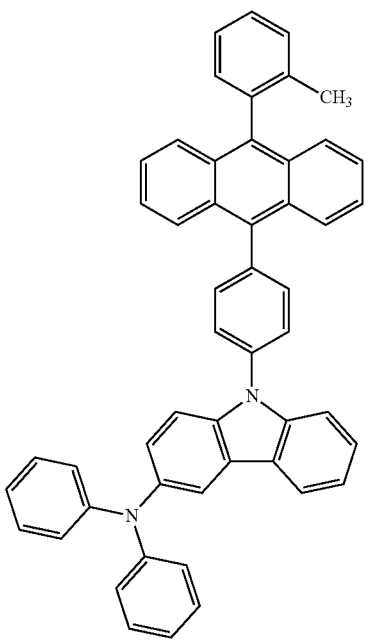
(83)
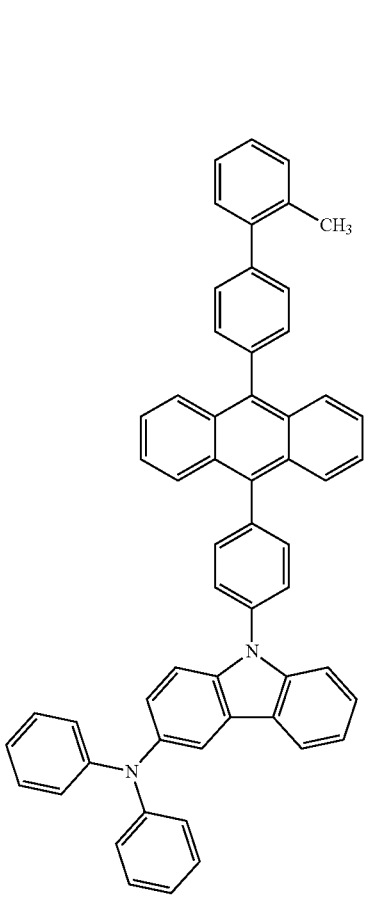

-continued
(84)
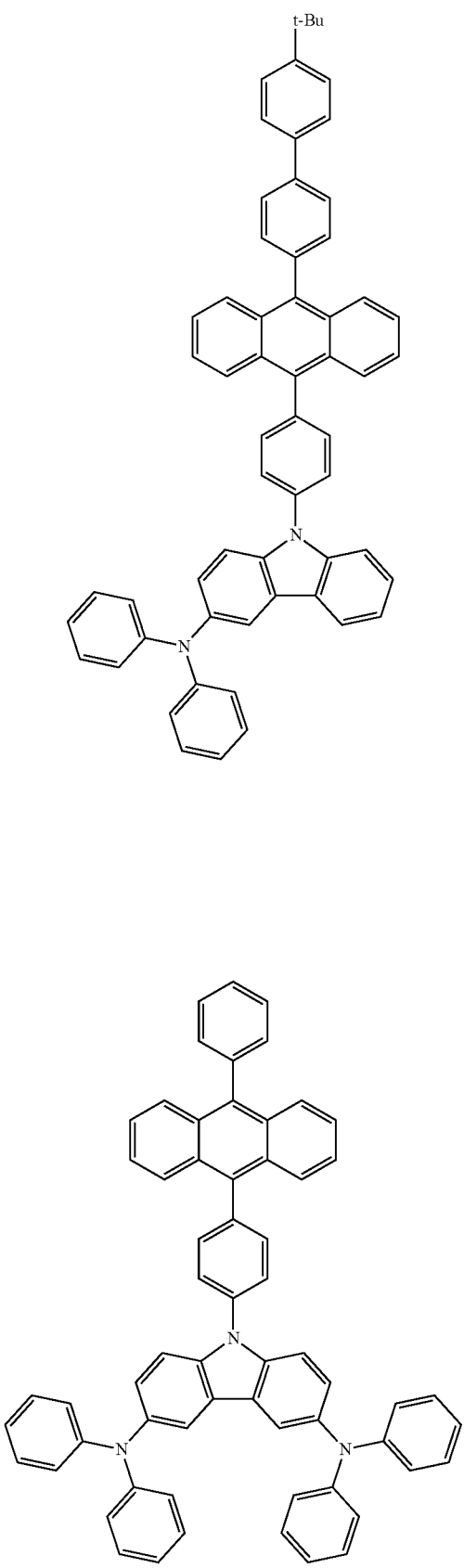
(85)
(86)
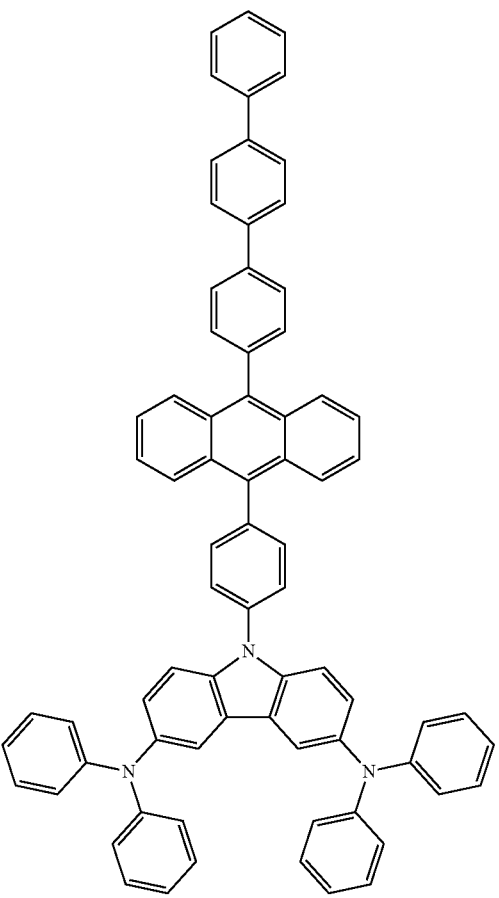

(87)
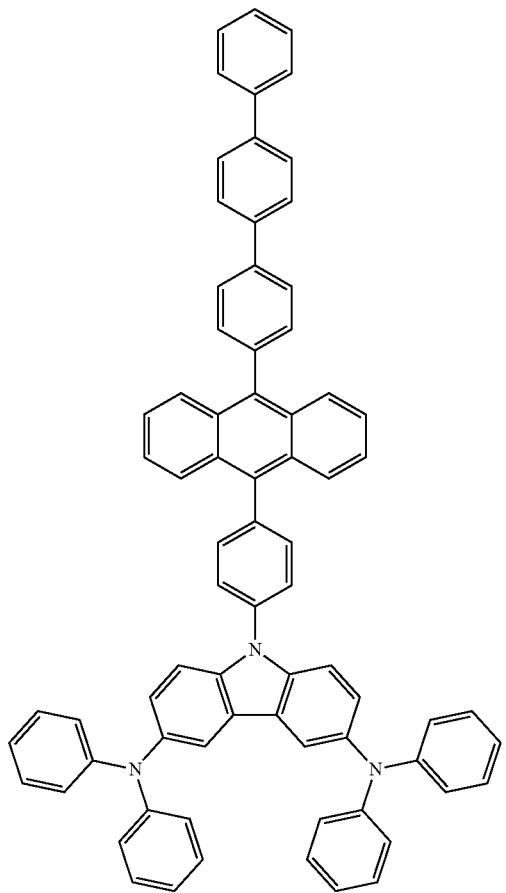
(88)
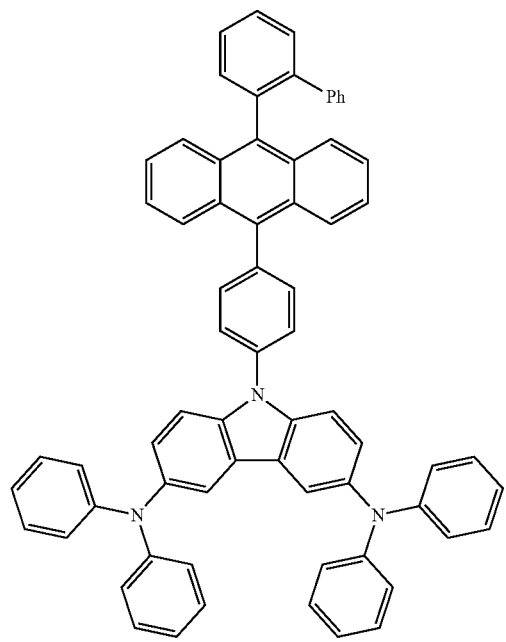
(89)
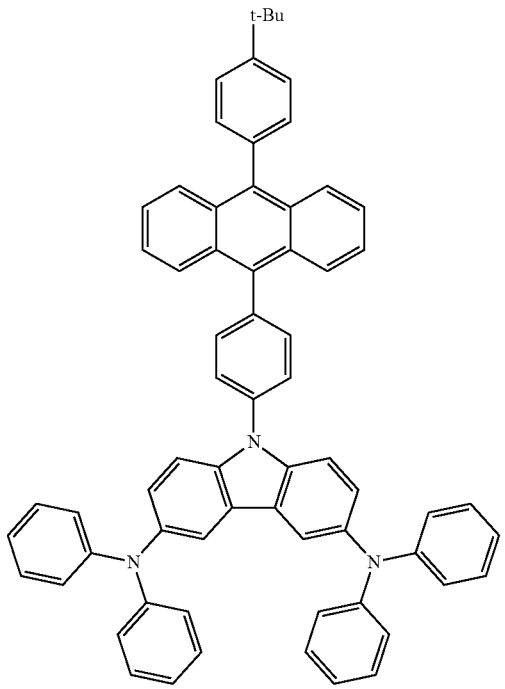
(90)
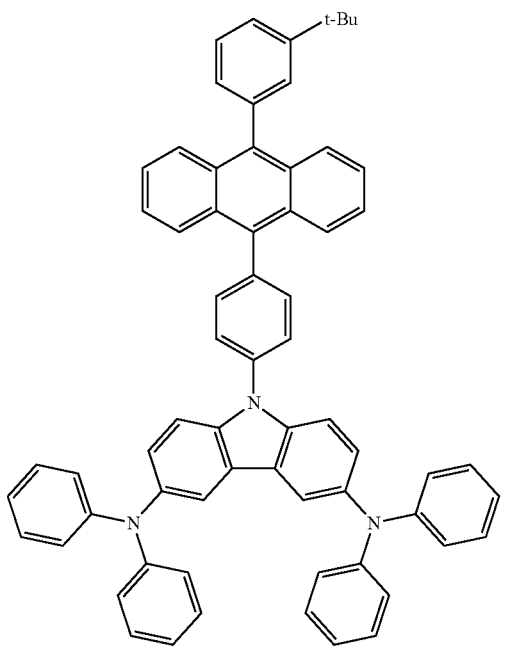

(91)
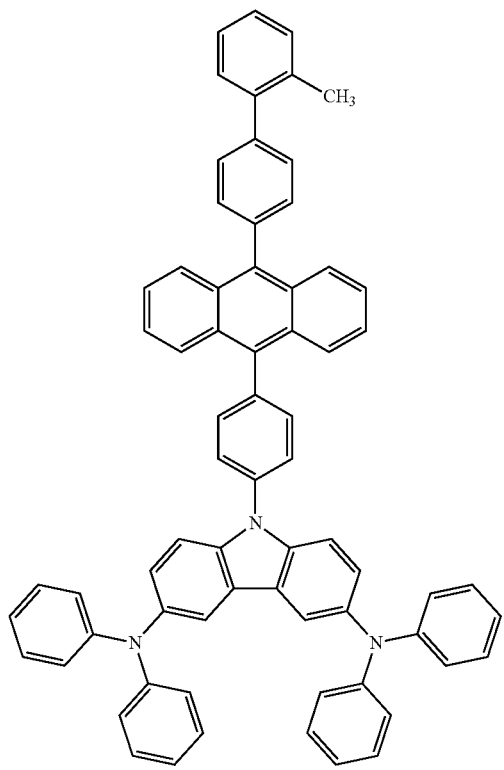
(93)
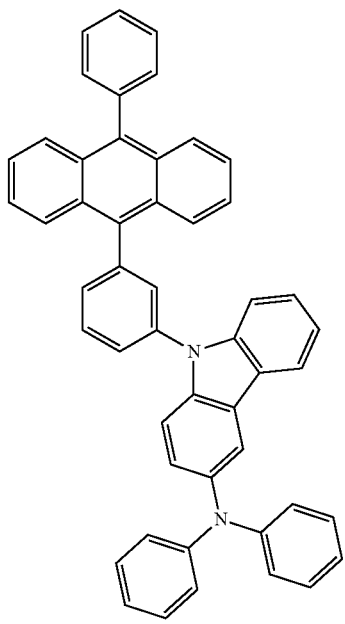
(92)
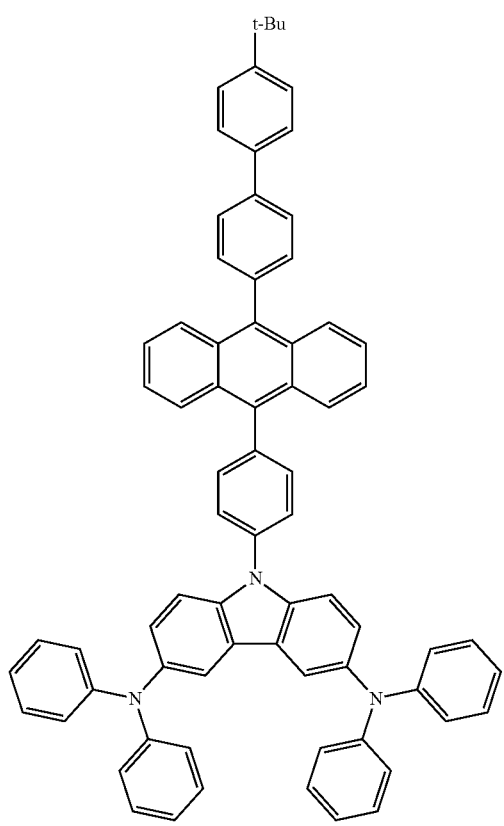
(94)
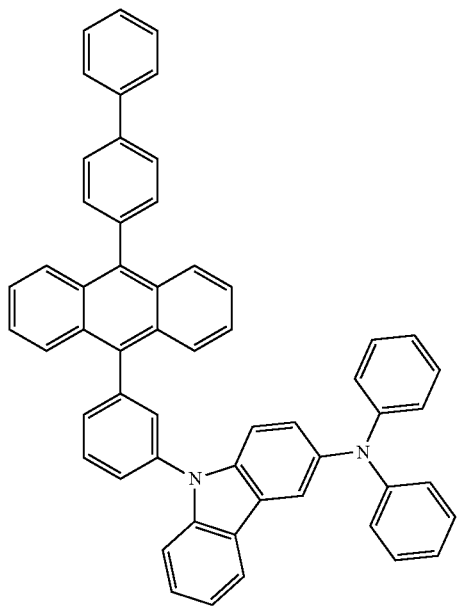

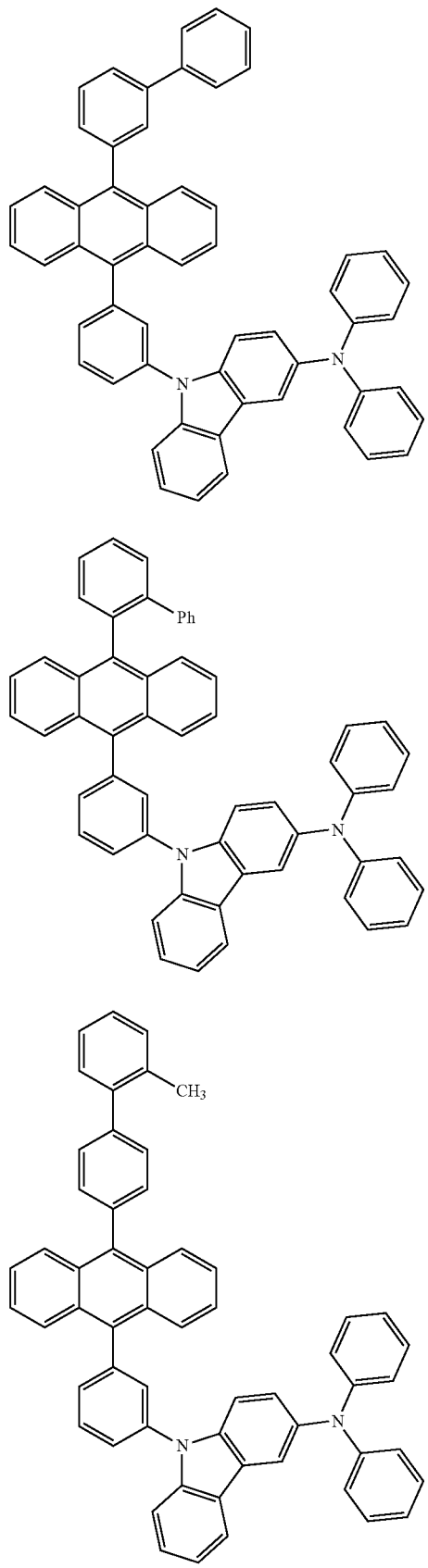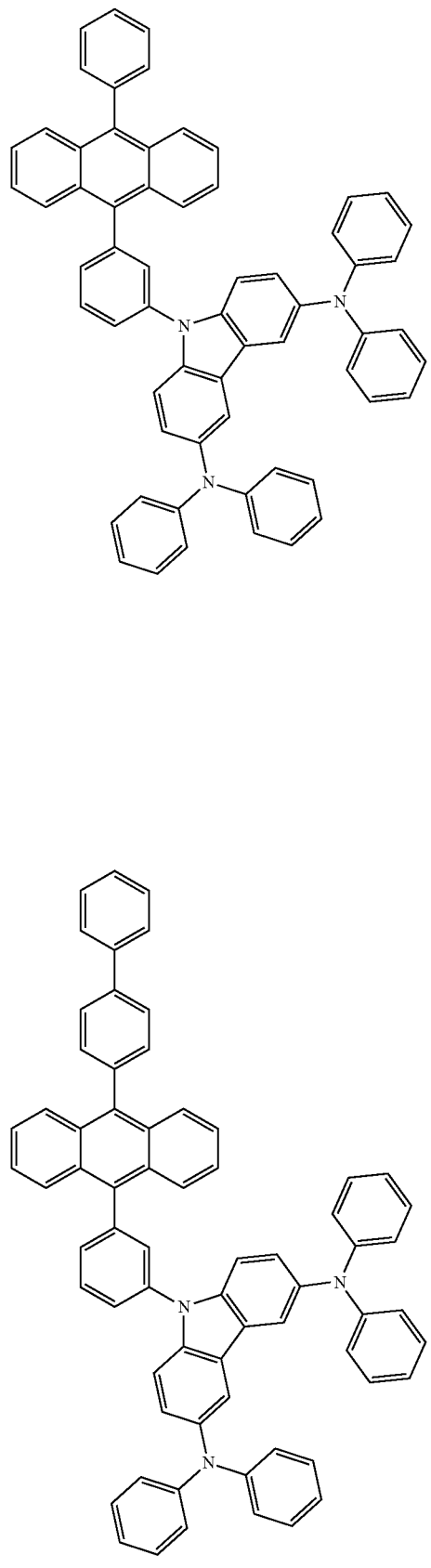

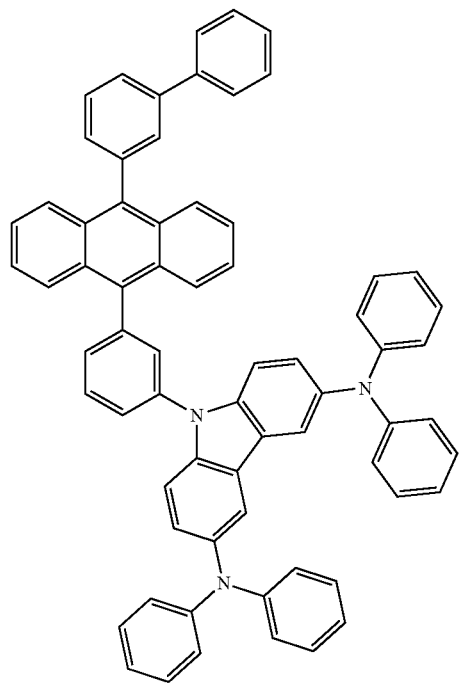# (100)
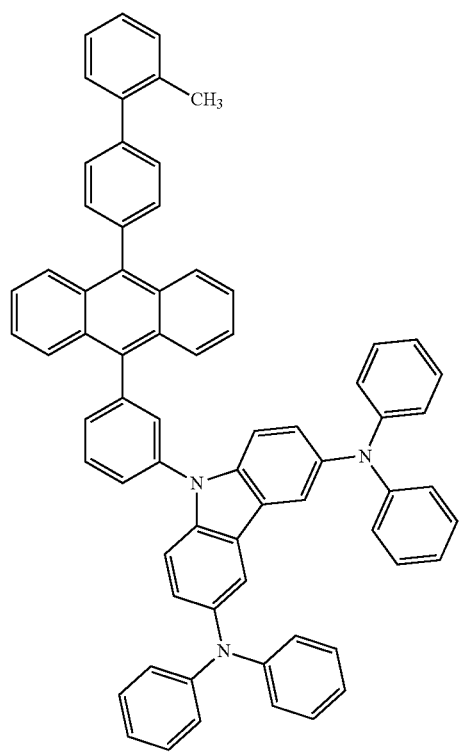# (101)
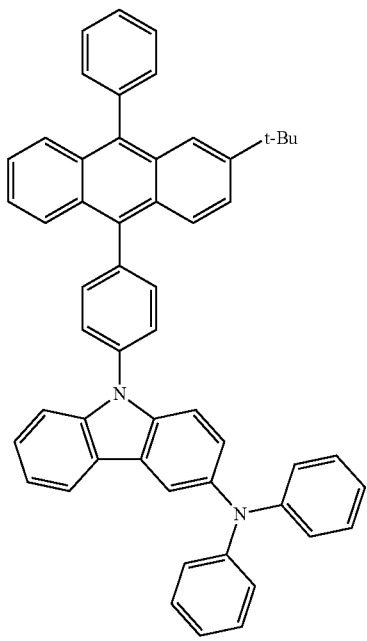# (102)
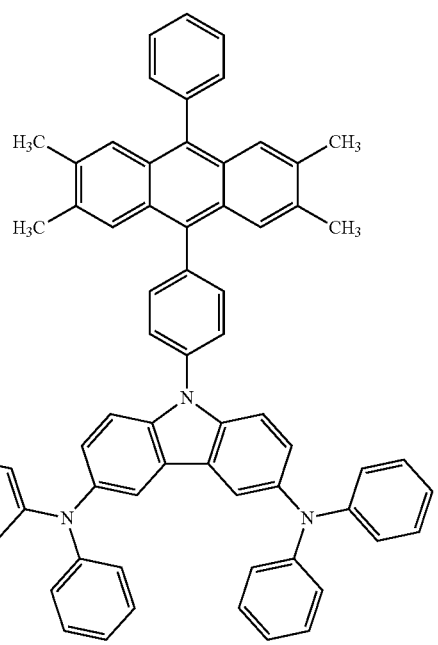# (103)

(104)
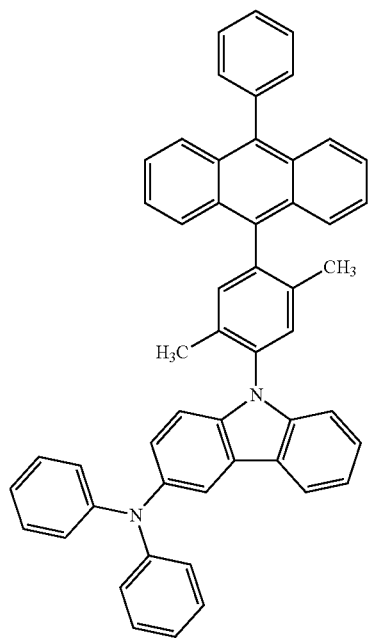
(106)
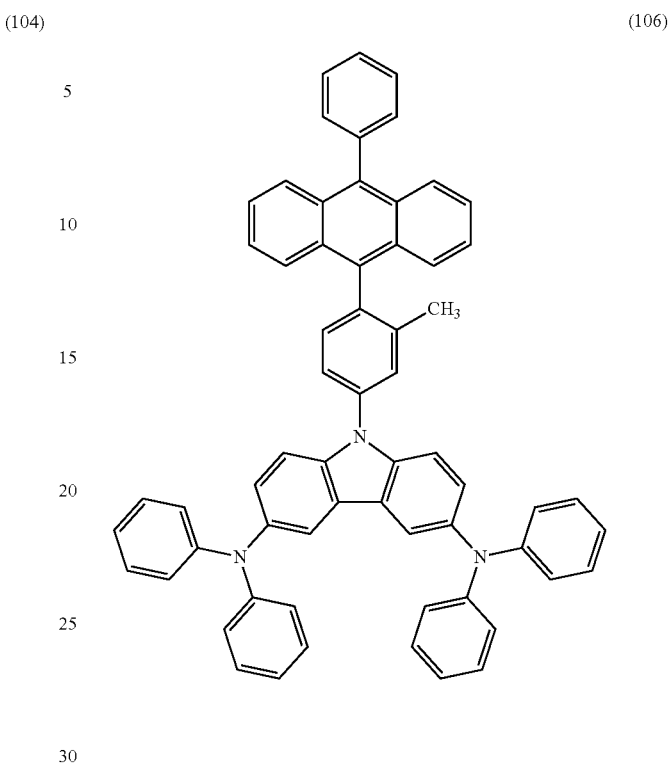
(105)
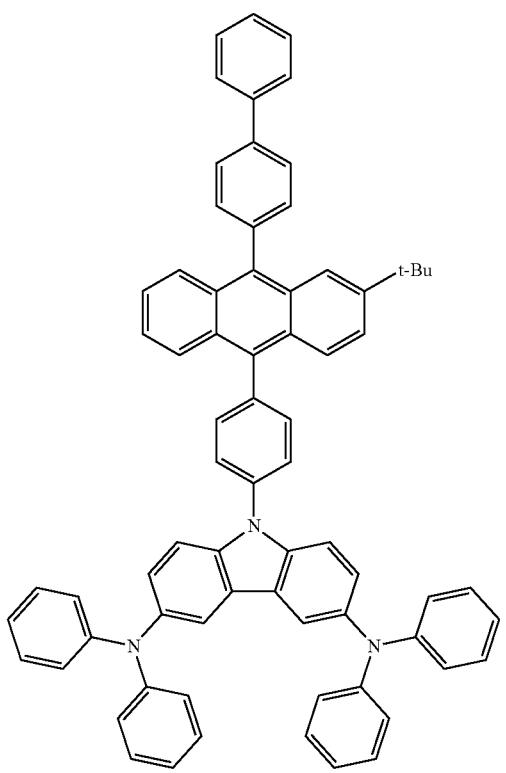
(107)
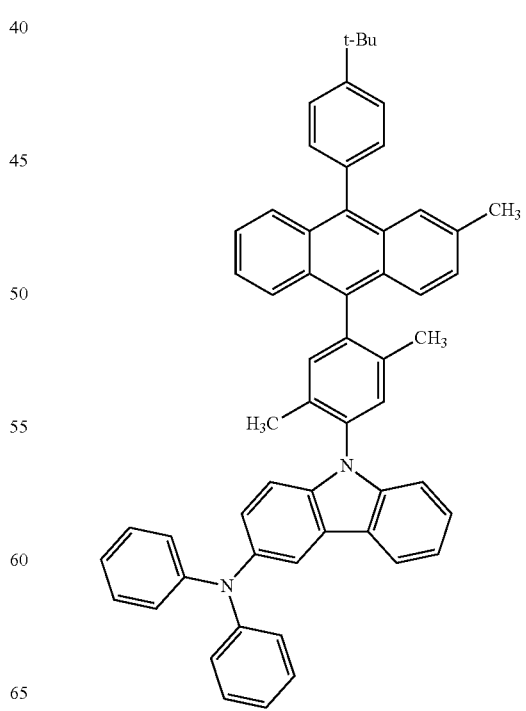

-continued
(108)
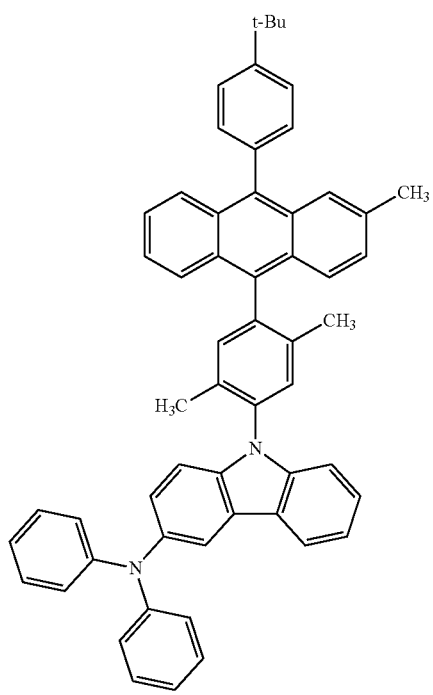
(109)
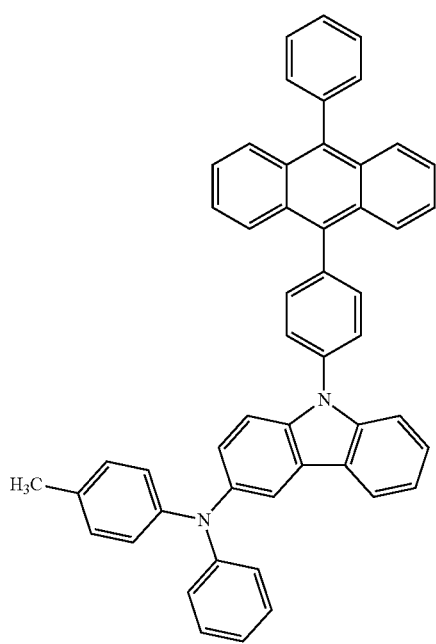
(110)
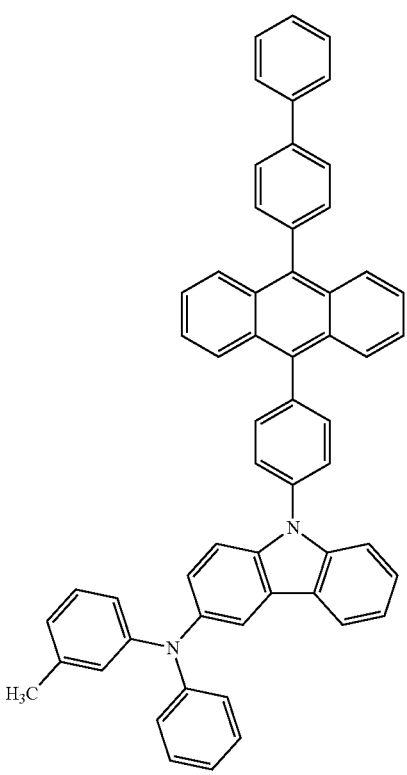
(111)
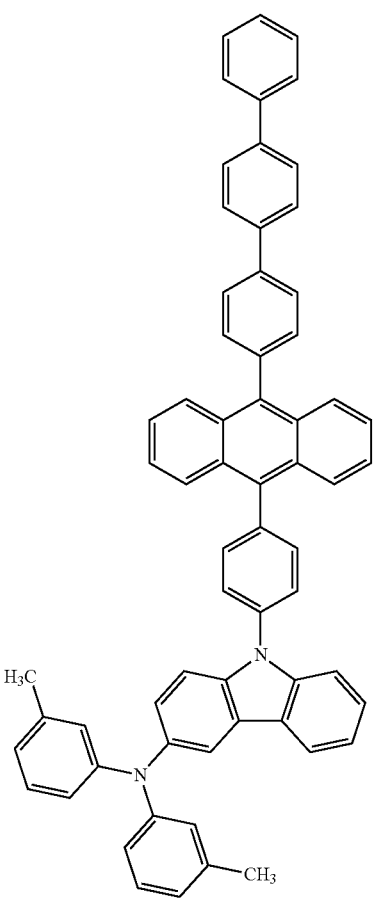

(112)
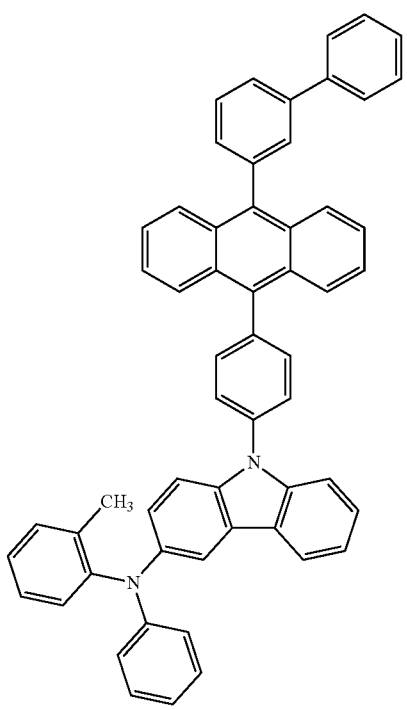
(113)
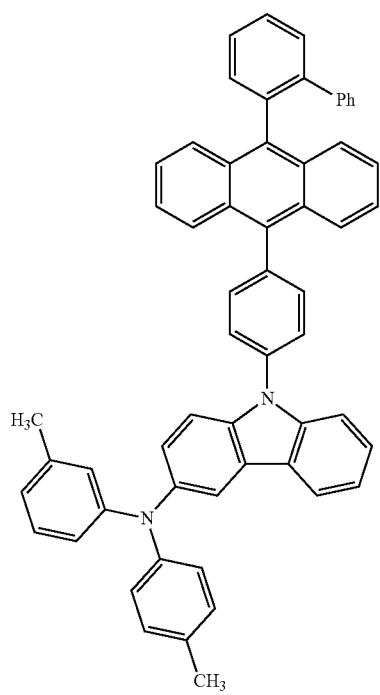
(114)
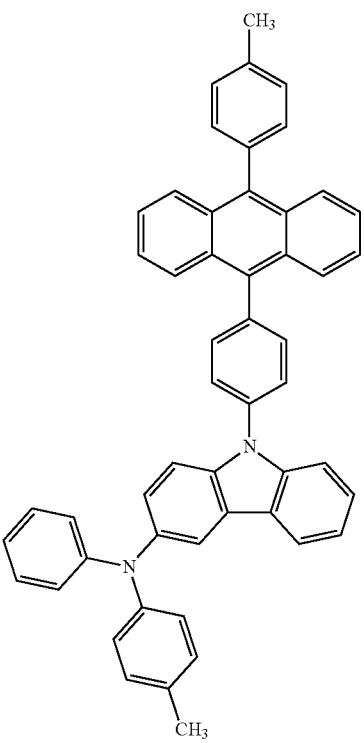
(115)
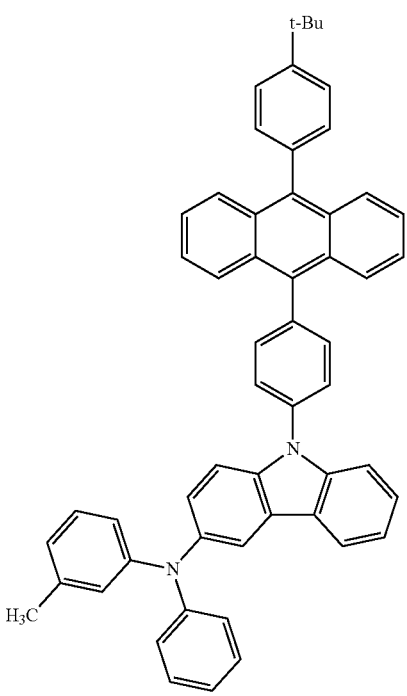

(116)
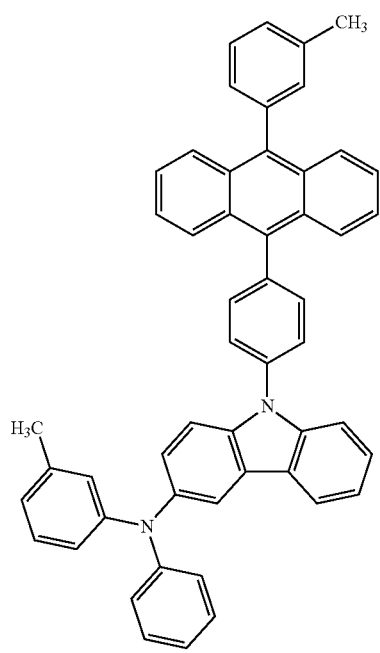
(117)
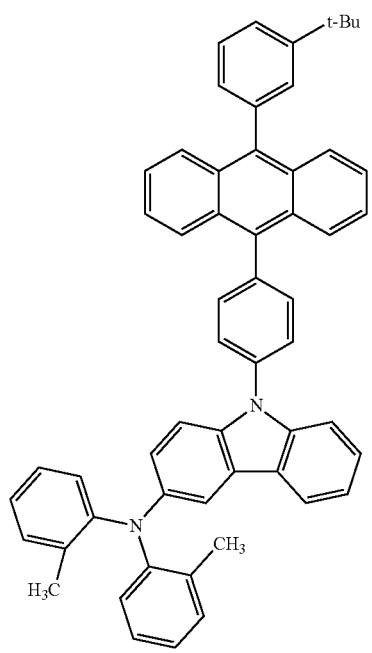
(118)
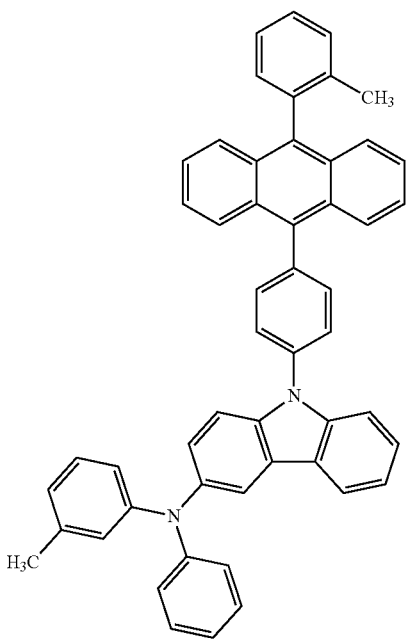
(119)
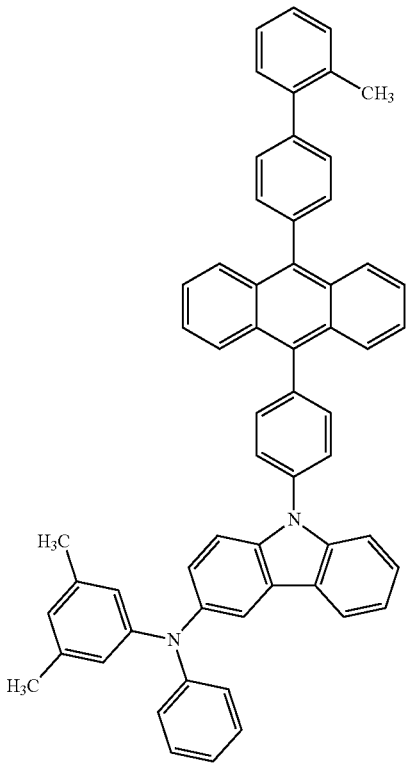

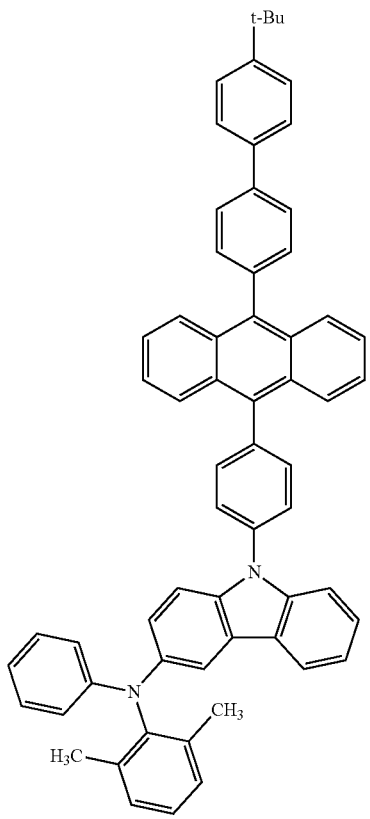

(120)

Embodiment 2

Embodiment 2 will describe a light emitting element using an anthracene derivative described in Embodiment 1.

In a structure of a light emitting element of the present invention, a layer containing a light emitting material is formed between a pair of electrodes. The element structure is not limited in particular; a known structure can be appropriately selected in accordance with the purpose.

FIG. 1 schematically shows an element structure of a light emitting element according to the present invention as one example. The light emitting element shown in FIG. 1 includes a layer 102 containing a light emitting material between a first electrode 101 and a second electrode 103. The layer 102 containing a light emitting material includes an anthracene derivative of the Embodiment 1. An anode in the present invention is an electrode for injecting holes into the layer including a light emitting material. A cathode in the present invention is an electrode for injecting electrons into the layer containing a light emitting material. One of the first and second electrodes is an anode and the other is a cathode. Note that in FIG. 1, reference numeral 100 denotes an insulator.

As the anode, known materials can be used; for example, a metal, an alloy, a conductive compound, or a mixture thereof each having a high work function (specifically, 4.0 eV or more) is preferably used. Specifically, indium tin oxide (also, referred to as ITO), indium tin oxide containing silicon, indium oxide containing zinc oxide (ZnO) of 2 to 20 wt % (IZO), or the like can be used. Such conductive metal oxide films are generally formed by sputtering; however, they may be formed by applying a sol-gel method or the like. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride (TiN)), or the like can also be used.

As the cathode, known materials can be used, and a metal, an alloy, a conductive compound, or a mixture thereof each having a low work function (specifically, 3.8 eV or less) is preferably used. Specifically, a metal that belongs to Group 1 or 2 of the periodic table, namely, an alkali metal such as lithium (Li) and cesium (Cs); an alkaline earth metal such as magnesium (Mg), calcium (Ca), and strontium (Sr); an alloy containing the alkali metal or the alkaline earth metal (e.g., MgAg, AlLi); a rare earth metal such as europium (Eu) and ytterbium (Yb); an alloy containing the rare earth metal, or the like can be used. Note that, a material having a high work function, namely, a material that is normally used for an anode, can be used to form the cathode by using the electron injecting layer having high electron injecting property. For example, the cathode can also be formed using a metal or a conductive inorganic compound such as Al, Ag, or ITO.

As the layer 102 containing a light emitting material, a known material can be used, and whichever of a low molecular weight material and a high molecular weight material can be used. It is to be noted that the structure of the material for forming the layer 102 containing a light emitting material includes not only a structure containing only an organic compound but also a structure partially containing an inorganic compound. In addition, the layer containing a light emitting material is formed by appropriately combining a hole injecting layer, a hole transporting layer, a hole blocking layer, a light emitting layer, an electron transporting layer, an electron injecting layer, and the like which have various functions. Further, the layer including a light emitting material may have a single layer structure or a structure in which a plurality of the above described layers are stacked. In addition, a layer having two or more functions of the respective functions of the layers may be included.

The layer containing a light emitting material can be formed by a wet type or dry type method such as vapor deposition, an ink-jet method, spin coating, or dip coating.

The anthracene derivative described in Embodiment 1 has a large band gap, and can emit light having short wavelength. Therefore, since the anthracene derivative can emit blue light with good color purity, it can be used as a light emitting material of the light emitting layer. In this case, only one kind of the anthracene derivatives described in Embodiment 1 may be used so that the light emitting layer may be formed with a so-called single layer film.

In addition, a light emitting material having a band gap smaller than the anthracene derivative of Embodiment 1 (hereinafter referred to as a dopant) is added into a layer containing the anthracene derivative of Embodiment 1 to obtain a structure in which light emitted from the dopant can be obtained. At this time, the anthracene derivative described in Embodiment 1 functions as a host. Since the anthracene derivative of Embodiment 1 has a large band gap, even if a dopant emitting light of a relatively short wavelength is used, light emitted from the dopant can be obtained efficiently instead of light emitted from the anthracene derivative. Specifically, a light emitting material having a maximum emission wavelength around 450 nm exhibits excellent color purity of blue, and such a material can be used as the dopant. Further a light emitting material having a maximum emission wavelength at about 500 nm exhibits excellent color purity of green color, and such a material can be used as the dopant. Similarly, a light emitting material having a maximum emission wavelength at about 650 nm, which displays excellent color purity of red, and such a material can be used as the dopant. However, a dopant having long wavelength generally presents in a long wavelength region. In the case where the anthracene derivative described in Embodiment 1 is used as a host, it is desirable that there is an overlap between the emission spectrum of the anthracene derivative and the absorption spectrum of the dopant. This is because the energy transfer becomes difficult in the absence of overlap between the emission spectrum of the host and the absorption spectrum of the dopant.

In the case where a dopant is added into a host containing an anthracene derivative of Embodiment 1 in a light emitting layer to obtain light from the dopant, whichever of a fluorescent material and a phosphorescent material can be used as the light emitting material to be added. Note that in the case of using a phosphorescent material, it is essential that the triplet energy level of the phosphorescent material is lower than that of the anthracene described in Embodiment 1. Note that, specifically, as examples of the light emitting materials, coumarin derivatives, oligophenylene derivatives, oxazole derivatives, stilbene derivatives, quinolone derivatives, acridone derivatives, anthracene derivatives, pyrene derivatives, phenanthrene derivatives, and the like are suitable. The dopant is added in small amounts, specifically, at 0.001 to 50 wt %, preferably, 0.03 to 20 wt %.

Meanwhile, a material which is to serve a host can be doped with the anthracene derivative described in Embodiment 1, thereby using it as a dopant. In this case, one of the conditions for the host is a compound having larger band gap than the anthracene derivative of Embodiment 1 which is used as a dopant. Therefore, in this case, the anthracene derivative of Embodiment 1 which has larger band gap than the anthracene derivative of Embodiment 1 which is used as a dopant can be used as a host. Specifically, it is preferable that an anthracene derivative described in Embodiment 1 which does not have a diarylamino group as shown in structural formulae (11) to (72) is suitably used as a host, and the anthracene derivative described in Embodiment 1 which has a diarylamino group as shown in structural formulae (73) to (120) is suitably used as a dopant. Naturally, the anthracene derivatives of the invention having diarylamino groups or the anthracene derivatives of the invention having diarylamino groups can be used as a host and a guest in a light emitting layer, considering the size of the band gap. Thus, an anthracene derivative of the present invention can be used for whichever of light emitting layers; accordingly, a light emitting element with higher reliability can be obtained.

Naturally, a material other than the anthracene derivative described in Embodiment 1 can be used as a host. Specifically, tetraaryl silane derivatives, dinaphthalene derivatives, pyrene derivatives, oligothiophene derivatives, benzophenone derivatives, benzonitrile derivatives, or the like can be used as a host. The host formed of such a material is doped with the anthracene derivative described in Embodiment 1 which has smaller band gap than the host as a dopant; thus, blue light with good color purity can be emitted from the anthracene derivative described in Embodiment 1. Further, a highly reliable light emitting element can be obtained by using an anthracene derivative described in Embodiment 1.

Not only the light emitting layer between the cathode and anode but also layers formed using different materials may be stacked on cathode and anode sides of the light emitting layer. Specifically, when an electron injecting layer and a hole injecting layer for promoting carrier injection from electrodes are arranged between the light emitting layer and the cathode, or between the light emitting layer and the anode, respectively; thus, the driving voltage can be reduced.

As a hole injecting material that forms a hole injecting layer, known materials can be used. Specifically, a metal oxide such as vanadium oxide, molybdenum oxide, ruthenium oxide, or aluminum oxide is preferable. An appropriate organic compound may be mixed with such an oxide. Alternatively, a porphyrin compound is effective among organic compounds, and phthalocyanine (H2-Pc), copper phthalocyanine (Cu-Pc), or the like can also be used. Further, a material that is obtained by chemical doping to a conductive high molecular weight compound, for example, polyethylene dioxythiophene (PEDOT) doped with polystyrene sulfonate (PSS), polyaniline (PAni), or the like can be used.

As an electron injecting material that forms an electron injecting layer, known materials can be used. Specifically, an alkali metal salt or an alkaline earth metal salt such as calcium fluoride, lithium fluoride, lithium oxide, or lithium chloride is preferable. A layer in which a compound with donating property such as lithium is added into a material having an electron transporting property, such as tris(8-quinolinolato) aluminum (Alq3) or bathocuproine (BCP) can also be used.

A carrier injection barrier is reduced and carriers are injected into a light emitting element efficiently by using such electron and hole injecting layers. As a result, decrease in the driving voltage can be achieved.

A carrier transporting layer is preferably formed between a carrier injecting layer and the light emitting layer. This is because, when the carrier injecting layer is in contact with the light emitting layer, a part of light emitted from the light emitting layer is quenched; thus, emission efficiency may be decreased. In the case of using the hole transporting layer, the hole transporting layer is arranged between the hole injecting layer and the light emitting layer. As a preferred material, an aromatic amine based compound (i.e., one having a bond of a benzene ring and nitrogen) can be used. As the material widely used, a star burst aromatic amine compound such as 4,4'-bis[N-(3-methylphenyl)-N-phenyl-amino]-biphenyl; or derivatives thereof such as 4,4'-bis[N-(1-naphthyl)-N-phenyl-amino]-biphenyl (hereinafter referred to as NPB); 4,4', 4"-tris(N,N-diphenyl-amino)-triphenylamine; or 4,4',4"-tris [N-(3-methylphenyl)-N-phenyl-amino]-triphenylamine can be used.

In the case of using an electron transporting layer, the electron transporting layer is arranged between the light emitting layer and an electron injecting layer. As a suitable material, a typical metal complex such as tris(8-quinolinolato) aluminum (Alq3), tris(4-methyl-8-quinolinolato) aluminum (Almq3), bis(10-hydroxybenzo[h]-quinolinato)beryllium (BeBq2), or bis(2-methyl-8-quinolinolato)-(4-hydroxy-biphenyl)-aluminum (BAlq), bis [2-(2-hydroxyphenyl)-benzoxazolato] zinc $(Zn(BOX)_2)$, or bis[2-(2-hydroxyphenyl)-benzothiazolato]zinc $(Zn(BTZ)_2)$ can be used. In addition, hydrocarbon based compounds such as 9,10-diphenylanthracene or 4,4'-bis(2,2-diphenyl ethenyl) biphenyl are preferred. Further, a triazole derivative such as 3-(4-tert-buthylphenyl)-4-(4-ethylphenyl)-5-(4-biphenylyl)-1,2,4-triazole, or a phenanthroline derivative such as bathophenanthroline or bathocuproine may be used.

The anthracene derivative described in Embodiment 1 has an extremely large band gap. Therefore, by using the anthracene derivative described in Embodiment 1 as a light emitting material or a dopant in a light emitting layer, a light emitting element according to the invention can emit light with extremely short wavelength, and can emit blue light with good color purity; further, a highly reliable light emitting element can be obtained. In addition, a light emitting element according to the invention can provide blue light with good color purity using the anthracene derivative described in Embodiment 1 as a host in the light emitting layer; further, a highly reliable light emitting element can be obtained.

The anthracene derivative described in Embodiment 1 has high electrochemical and thermal stability. Further, since not a condensed aromatic group but a phenyl group is coupled with 9 and 10 positions of the anthracene described in Embodiment 1 as a substituent, the excited state is highly stable. Therefore, a light emitting element using the anthracene derivative described in Embodiment 1 is highly reliable and can provide excellent color purity as blue light.

Note that, in this embodiment, the structure of a light emitting element in which light is obtained only from a light emitting layer has been described. However, it may be designed to provide light emitted from not only a light emitting layer but also from another layer, for example, an electron transporting layer or a hole transporting layer. For example, if an electron transporting layer or a hole transporting layer is doped with a dopant which contributes to emit light, light can be emitted not only from a light emitting layer but also from a transporting layer. When light emitting materials used for the light emitting layer and the transporting layer have different light emission colors, a spectrum in which the lights overlap one another can be obtained. When the light emission colors are complementary to each other, white light can be emitted.

Note that, as sorts of the first electrode 101 and the second electrode 103 are varied, light emitting elements of this embodiment have different variations. When the first electrode 101 transmits light, light is emitted toward the first electrode 101 side. Meanwhile, when the first electrode 101 blocks light (particularly, reflects light), and the second electrode 103 transmits light, light is emitted toward the second electrode 103 side. In addition, when both the first electrode 101 and the second electrode 103 transmit light; light can be emitted toward both the first electrode side and the second electrode side.

Embodiment 3

This embodiment will describe a light emitting device according to the present invention shown with reference to FIGS. 2A to 4B showing the manufacturing methods. Although this embodiment shows an example of manufacturing an active matrix light emitting device, the present invention is also applicable to a passive light emitting device.

Figure 2A:
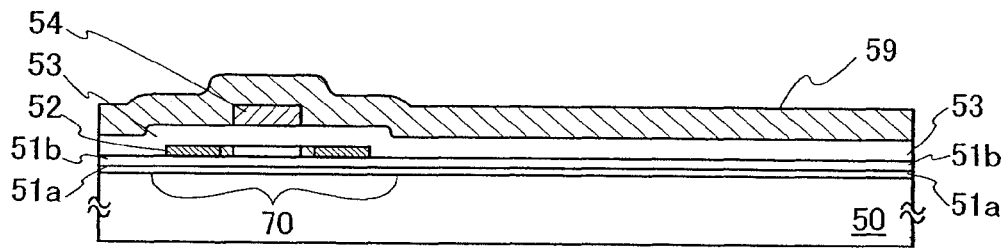
FIGS. 2A to 2E are cross-sectional views for explaining a method of manufacturing an active matrix light emitting device of the present invention.

First, a first base insulating layer 51a and a second base insulating layer 51b are formed over a substrate 50, and then a semiconductor layer is formed over the second base insulating layer 51b (FIG. 2A).

As a material of the substrate 50, glass, quartz, plastic (such as polyimide, acrylic, polyethylene terephthalate, polycarbonate, polyacrylate, or polyethersulfone), or the like can be used. These substrates may be used after being polished by CMP or the like as necessary. In this embodiment, a glass substrate is used.

The first base insulating layer 51a and the second base insulating layer 51b are provided in order to prevent an element, which adversely affects the characteristics of the semiconductor film, such as alkali metal or alkali-earth metal in the substrate 50 from diffusing into the semiconductor layer. As the material of the base insulating layers, silicon oxide, silicon nitride, silicon oxide containing nitrogen, silicon nitride containing oxygen, or the like can be used. In this embodiment, the first base insulating layer 51a is formed of silicon nitride, and the second base insulating layer 51b is formed of silicon oxide. Although the base insulating layer is formed in a two-layer structure including the first base insulating layer 51a and the second base insulating layer 51b in this embodiment, the base insulating layer may be formed in a single-layer structure or a multilayer structure including three or more layers. The base insulating layer may not necessary be provided when the diffusion of the impurity from the substrate does not lead to a significant problem.

In this embodiment, the semiconductor layer formed subsequently is obtained by crystallizing an amorphous silicon film with a laser. The amorphous silicon film is formed to a thickness of 25 to 100 nm (preferably 30 to 60 nm) over the second base insulating layer 51b by a known method such as sputtering, low-pressure CVD, or plasma CVD. After that, heat treatment is conducted for one hour at 500° C. for dehydrogenation.

Subsequently, the amorphous silicon film is crystallized using a laser irradiation apparatus to form a crystalline silicon film. In this embodiment, an excimer laser is used in the laser crystallization. After the emitted laser beam is shaped to have a linear beam spot using an optical system, the amorphous silicon film is irradiated with the linear beam spot. Thus, the crystalline silicon film is formed to be used as the semiconductor layer.

Alternatively, the amorphous silicon film can be crystallized by another method such as a method in which the crystallization is conducted only by heat treatment or a method in which heat treatment is conducted using a catalyst element for promoting the crystallization. As the element for promoting the crystallization, nickel, iron, palladium, tin, lead, cobalt, platinum, copper, gold, or the like is used. By using such an element, the crystallization is conducted at lower temperature in a shorter time than the crystallization only by heat treatment; therefore, damage to the glass substrate is suppressed. In the case of crystallizing only by heat treatment, a quartz substrate or the like which can resist heat is preferably used as the substrate 50.

Subsequently, a minute amount of impurities are added to the semiconductor layer as necessary in order to control the threshold value, which is so-called channel doping. In order to obtain the required threshold value, an impurity of N-type or P-type (such as phosphorus or boron) is added by an ion-doping method or the like.

After that, as shown in FIG. 2A, the semiconductor layer is processed into a predetermined shape so that an island-shaped semiconductor layer 52 is obtained. The process is conducted by etching the semiconductor layer using a mask. The mask is formed in such a way that the semiconductor layer is coated with a photo resist and the photo resist is exposed and baked so that a resist mask having a desired mask pattern is formed over the semiconductor layer.

Next, a gate insulating layer 53 is formed so as to cover the semiconductor layer 52. The gate insulating layer 53 is formed to a thickness of 40 to 150 nm using an insulating layer containing silicon by plasma CVD or sputtering. In this embodiment, silicon oxide is used.

Then, a gate electrode 54 is formed over the gate insulating layer 53. The gate electrode 54 may be formed of an element selected from tantalum, tungsten, titanium, molybdenum, aluminum, copper, chromium, or niobium, or may be formed of an alloy material or a compound material which contains the above element as its main component. Further, a semiconductor film typified by a polycrystalline silicon film doped with an impurity element such as phosphorus may be used. An Ag—Pd—Cu alloy may also be used.

Although the gate electrode 54 is formed from a single layer in this embodiment, the gate electrode 54 may have a layered structure including two or more layers of, for example, tungsten in a lower layer and molybdenum in an upper layer. Even in the case of forming the gate electrode having a layered structure, the above-mentioned material is preferably used. The combination of the above materials may also be selected appropriately. The gate electrode 54 is processed by etching with the use of a mask formed of a photo resist.

Subsequently, impurities are added to the semiconductor layer 52 so as to form a high concentration region using the gate electrode 54 as the mask. Accordingly, a thin film transistor 70 including the semiconductor layer 52, the gate insulating layer 53, and the gate electrode 54 is formed.

The manufacturing method of the thin film transistor is not limited in particular, and may be appropriately modified so that a transistor having a desired structure can be manufactured.

Although this embodiment employs a top-gate thin film transistor using a crystalline silicon film obtained by the laser crystallization, a bottom-gate thin film transistor using an amorphous semiconductor film can also be applied to a pixel area. Not only silicon but also silicon germanium can be used for the amorphous semiconductor. In the case of using silicon germanium, the concentration of germanium preferably ranges from approximately 0.01 to 4.5 atomic %.

Moreover, a microcrystal semiconductor (semiamorphous semiconductor) film which includes crystal grains each having a diameter of 0.5 to 20 nm in an amorphous semiconductor may also be used. The crystal having the crystal grains with a diameter of 0.5 to 20 nm is also referred to as what is called a microcrystal ($\mu$c).

Semiamorphous silicon (also referred to as SAS), which is a semiamorphous semiconductor, can be obtained by decomposing SiH4, Si2H6, SiH2Cl2, SiHCl3, SiCl4, SiF4, or the like by glow discharging. By using such a gas after diluting the silicide gas with hydrogen or hydrogen and one or plural kinds of inert gas selected from helium, argon, krypton, or neon, SAS can be easily formed. The silicide gas is preferably diluted with the dilution ratio of 1:10 to 1:1000. The reaction to form the coating by glow discharge decomposition may be conducted at a pressure ranging from 0.1 to 133 Pa. The electric power for forming the glow discharging may be supplied at high frequency in the range of 1 to 120 MHz, preferably 13 to 60 MHz. The substrate heating temperature is preferably 300° C. or less, preferably in the range of 100 to 250° C.

The Raman spectrum of thus formed SAS shifts to the side of lower wavenumber than 520 cm$^{-1}$. According to X-ray diffraction, diffraction peaks of a silicon crystal lattice are observed at (111) and (220). As a terminating agent of a dangling bond, hydrogen or halogen is added by at least 1 atomic % or more. As the impurity element in the film, the impurity in the air such as oxygen, nitrogen, and carbon is desirably $1\times10^{20}$ cm$^{-1}$ or less, and especially, the concentration of oxygen is $5\times10^{19}$/cm$^3$ or less, preferably $1\times10^{19}$/cm$^3$ or less. The mobility of a TFT manufactured with this film is $\mu=1$ to 10 cm$^2$/Vsec.

This SAS may be used after being crystallized further with a laser beam.

Subsequently, an insulating film (hydride film) 59 is formed of silicon nitride so as to cover the gate electrode 54 and the gate insulating layer 53. After forming the insulating film (hydride film) 59, heat treatment for approximately 1 hour at 480° C. is conducted so as to activate the impurity element and to hydrogenate the semiconductor layer 52.

Figure 2B:
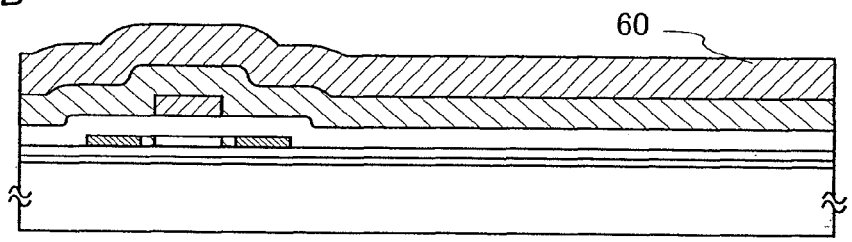

Subsequently, a first interlayer insulating layer 60 is formed to cover the insulating film (hydride film) 59. As a material for forming the first interlayer insulating layer 60, silicon oxide, acrylic, polyimide, siloxane, a low-k material, or the like is preferably used. In this embodiment, the first interlayer insulating layer is formed using a silicon oxide film (FIG. 2B).

Figure 2C:
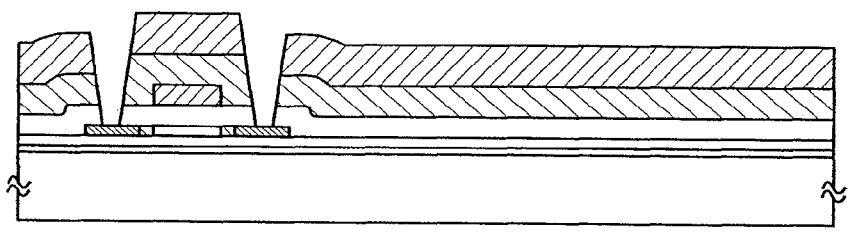

Next, contact holes that reach the semiconductor layer 52 are formed. The contact holes can be formed by etching using a resist mask until the semiconductor layer 52 is exposed. Either wet etching or dry etching can be carried out. The etching may be conducted once or a plurality of times depending on the condition. When the etching is conducted a plurality of times, both the wet etching and the dry etching may be conducted (FIG. 2C).

Figure 2D:
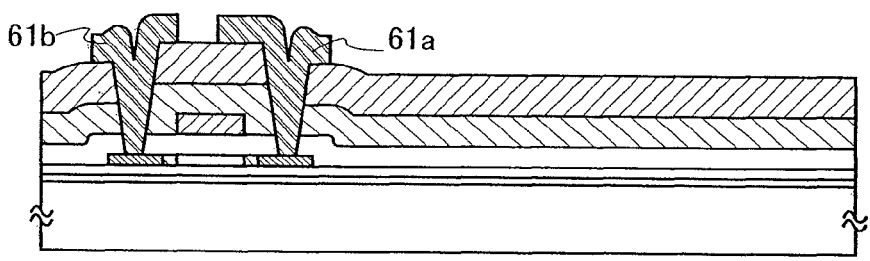

Then, a conductive layer is formed so as to cover the contact holes and the first interlayer insulating layer 60. A connection portion 61a, a wiring 61b, and the like are formed by processing the conductive layer into a desired shape. This wiring may be a single layer of aluminum; copper; an alloy of aluminum, carbon, and nickel; an alloy of aluminum, carbon, and molybdenum; or the like. The wiring is formed in a layered structure of molybdenum, aluminum, molybdenum in the order from the substrate. Alternatively, a structure of titanium, aluminum, titanium or titanium, titanium nitride, aluminum, titanium is also applicable (FIG. 2D).

Figure 2E:
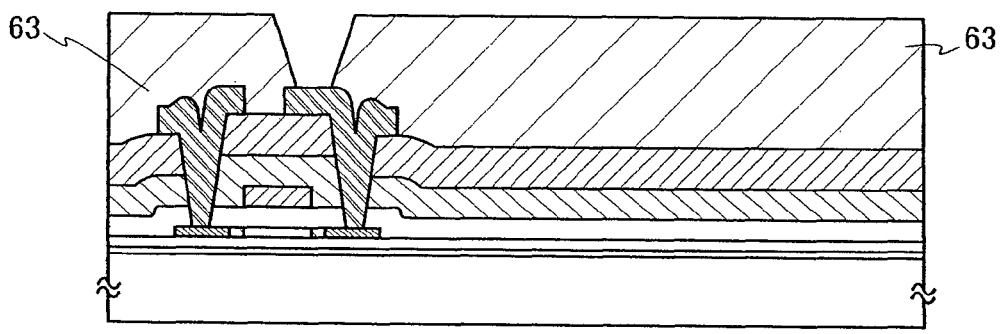

A second interlayer insulating layer 63 is formed to cover the connection portion 61a, the wiring 61b, and the first interlayer insulating layer 60. As the material of the second interlayer insulating layer 63, a self-planarized coating formed of acrylic, polyimide, siloxane, or the like is preferably used. In this embodiment, the second interlayer insulating layer 63 is formed of siloxane (FIG. 2E).

Next, an insulating layer may be formed of silicon nitride over the second interlayer insulating layer 63. This is to prevent the second interlayer insulating layer 63 from being etched more than necessarily in a later step of etching a pixel electrode. Therefore, the insulating layer is not necessary in particular when the difference of the etching rate is large between the pixel electrode and the second interlayer insulating layer. Next, a contact hole penetrating the second interlayer insulating layer 63 to reach the connection portion 61a is formed.

After a light-transmitting conductive layer is formed so as to cover the contact hole and the second interlayer insulating layer 63 (or the insulating layer), the light-transmitting conductive layer is processed to form the first electrode 64 of the thin film light emitting element. Here, the first electrode 64 electrically contacts the connection portion 61a.

The first electrode 64 can be formed from a conductive film as shown in Embodiment 1 using a material of a conductive metal such as aluminum (Al), silver (Ag), gold (Au), platinum (Pt), nickel (Ni), tungsten (W), chromium (Cr), molybdenum (Mo), iron (Fe), cobalt (Co), copper (Cu), palladium (Pd), lithium (Li), cesium (Cs), magnesium (Mg), calcium (Ca), strontium (Sr), or titanium (Ti); an alloy thereof such as aluminum-Si (Al—Si), aluminum-titanium (Al—Ti), or aluminum-silicon-copper (Al—Si—Cu); a nitride of a metal material such as titanium nitride (TiN), a metal compound such as indium tin oxide (indium tin oxide), ITO containing silicon, IZO (indium zinc oxide) in which 2 to 20 wt % of zinc oxide (ZnO) is mixed with indium oxide, or the like.

Figure 3A:
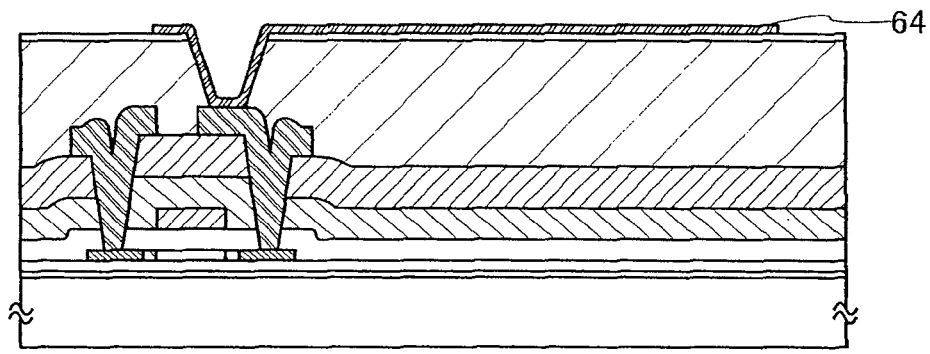
FIGS. 3A to 3C are cross-sectional views for explaining a method of manufacturing an active matrix light emitting device of the present invention.

An electrode through which light is emitted may preferably be formed using a light-transmitting conductive film. For example, a metal compound such as ITO (indium tin oxide), ITO containing silicon (ITSO), or IZO (indium zinc oxide) in which 2 to 20% of zinc oxide (ZnO) is mixed with indium oxide can be used. In addition, an extremely thin film of metal such as Al or Ag is used. When light is emitted through a second electrode, a material having high reflectance (e.g., Al, Ag or the like) can be used for the first electrode. In this embodiment, ITSO is used as the first electrode 64 (FIG. 3A).

Figure 3B:
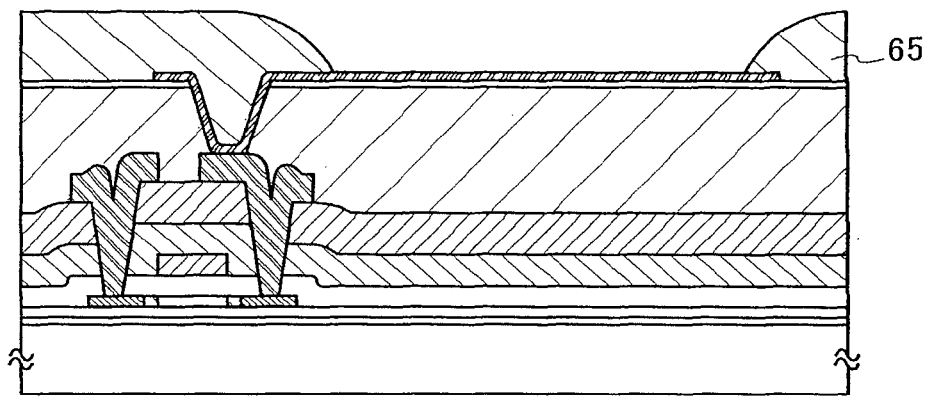
Figure 3C:
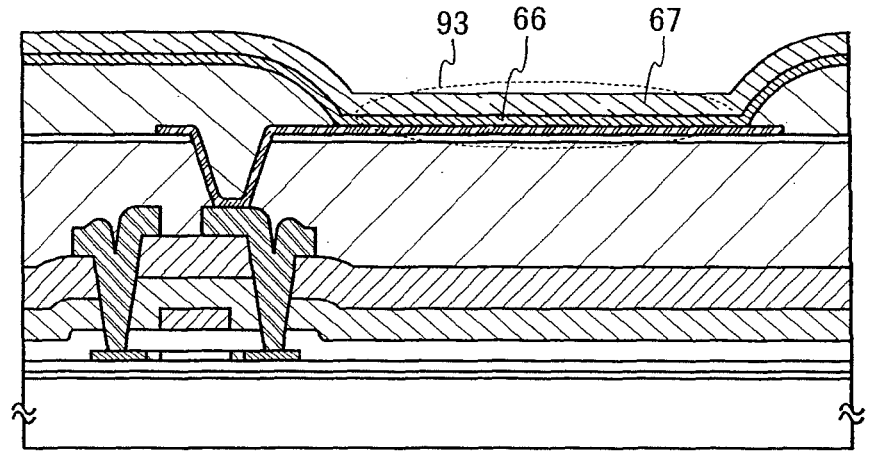

Next, an insulating layer formed of an organic material or an inorganic material is formed so as to cover the second interlayer insulating layer 63 (or the insulating layer) and the first electrode 64. Subsequently, the insulating layer is processed so as to partially expose the first electrode 64, thereby forming a partition wall 65. As the material of the partition wall 65, a photosensitive organic material (such as acrylic or polyimide) is preferable. Alternatively, a non-photosensitive organic or inorganic material may also be used. Further, the partition wall 65 may be used as a black matrix by making the partition wall 65 black in such a way that a black pigment or dye such as titanium black or carbon nitride is diffused into the material of the partition wall 65 using a dispersant or the like. It is desirable that the partition wall 65 has a tapered shape in its end surface toward the first electrode with its curvature changing continuously (FIG. 3B).

Next, a layer 66 containing a light emitting material is formed, and a second electrode 67 covering the layer 66 containing a light emitting substance is formed subsequently. Thus, a light emitting element 93 in which the layer 66 containing a light emitting substance is sandwiched between the first electrode 64 and the second electrode 67, and light emission can be obtained by applying higher voltage to the first electrode than the second electrode. For an electrode material used for forming the second electrode 67, the same material as the material of the first electrode can be used. Aluminum is used for the second electrode in this embodiment.

Further, the layer 66 containing a light emitting substance is formed by vapor deposition, an ink-jet method, spin coating, dip coating, or the like. The layer 66 containing a light emitting substance contains an anthracene derivative described in Embodiment 1. The layer 66 containing a light emitting material may be a laminate of layers having each function as explained in Embodiment 2, or may be a ingle layer of a light emitting layer. Further, the anthracene derivative described in Embodiment 1 is included as a light emitting layer in the layer 66 containing a light emitting material. The anthracene derivative described in Embodiment 1 may be contained as a host or a dopant or both of them of the light emitting layer. Further, the anthracene derivative described in Embodiment 1 may be contained in a layer other than the light emitting layer or as a part thereof in the layer containing a light emitting material. In particular, since the anthracene derivative of the present invention including a diarylamino group is superior in hole transport characteristics, it can be used for a hole transport layer. Further, a material to be combined with an anthracene derivative described in Embodiment 1 may be a low molecular weight material, an intermediate molecular weight material (including oligomer and dendrimer), or a high molecular weight material. Further, as a material to be used for a layer containing a light emitting material, a single layer of an organic compound or a laminate of organic compounds is generally used; however, in this embodiment, a structure in which an organic compound is contained in a part of a film of an organic compound is also included.

After that, a silicon oxide film containing nitrogen is formed as a passivation film by plasma CVD. In the case of using the silicon oxide film containing nitrogen, a silicon oxynitride film manufactured using $SiH_4$, $N_2O$, and $NH_3$ by plasma CVD, a silicon oxynitride film manufactured using $SiH_4$ and $N_2O$ by plasma CVD, or a silicon oxynitride film manufactured using a gas in which $SiH_4$ and $N_2O$ are diluted with Ar by plasma CVD is preferably formed.

As the passivation film, a silicon oxynitride hydride film manufactured using $SiH_4$, $N_2O$, and $H_2$ is also applicable. Naturally, the structure of the first passivation film is not limited to a single-layer structure, and the first passivation film may be formed in a single-layer structure or a layered structure including another insulating layer containing silicon. A multilayer film of a carbon nitride film and a silicon nitride film, a multilayer film including a styrene polymer, a silicon nitride film, or a diamond-like carbon film may be formed instead of a silicon oxide film containing nitrogen.

Subsequently, in order to protect the light emitting element from a deterioration-promoting material such as moisture, the display area is sealed. In the case of using a counter substrate for the sealing, the counter substrate and an element substrate are attached together with an insulating sealing material so as to expose an external connection portion. The space between the counter substrate and the element substrate may be filled with an inert gas such as dry nitrogen, or the whole surface of the pixel area may be coated with the sealing material for attaching the counter substrate. It is preferable to use an ultraviolet curable resin or the like for the sealing material. A drying agent or particles for keeping the gap between the substrates uniform may be mixed into the sealing material. Subsequently, a flexible wiring substrate is pasted on the external connection portion, thereby completing a light emitting device.

An example of the structure of the thus manufactured light emitting device will be described with reference to FIGS. 4A and 4B. Although the shapes are different, parts having the same function are denoted by the same reference numerals and the description thereof may be omitted. In this embodiment, the thin film transistor 70 having an LDD structure connects to the light emitting element 93 via the connection portion 61a.

Figure 4A:
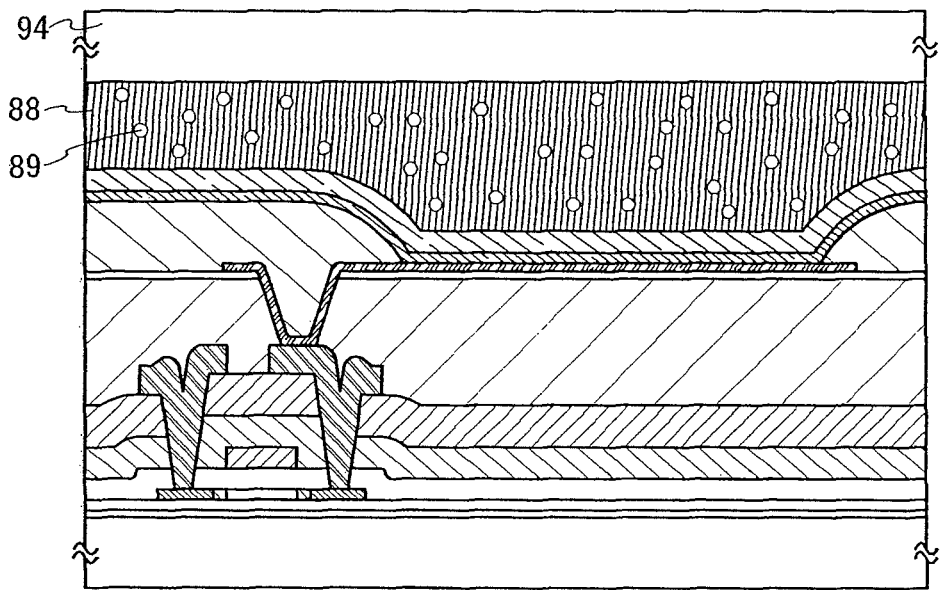
FIGS. 4A and 4B are cross-sectional views each showing a light emitting device of the present invention.

In FIG. 4A, the first electrode 64 is formed using a light-transmitting conductive film and has a structure in which light emitted from the light emitting stack 66 is extracted from the substrate 50 side. Reference numeral 94 denotes a counter substrate, which is to be fixed to the substrate 50 with a sealing material or the like after forming the light emitting element 93. By filling the space between the counter substrate 94 and the element with a light-transmitting resin 88 or the like and sealing the space, it is possible to prevent the light emitting element 93 from deteriorating due to the moisture. Further, the resin 88 desirably has hygroscopicity. In addition, it is more desirable that a desiccant 89 having high light-transmitting properties is diffused in the resin 88, so that the effect of moisture can be further suppressed.

Figure 4B:
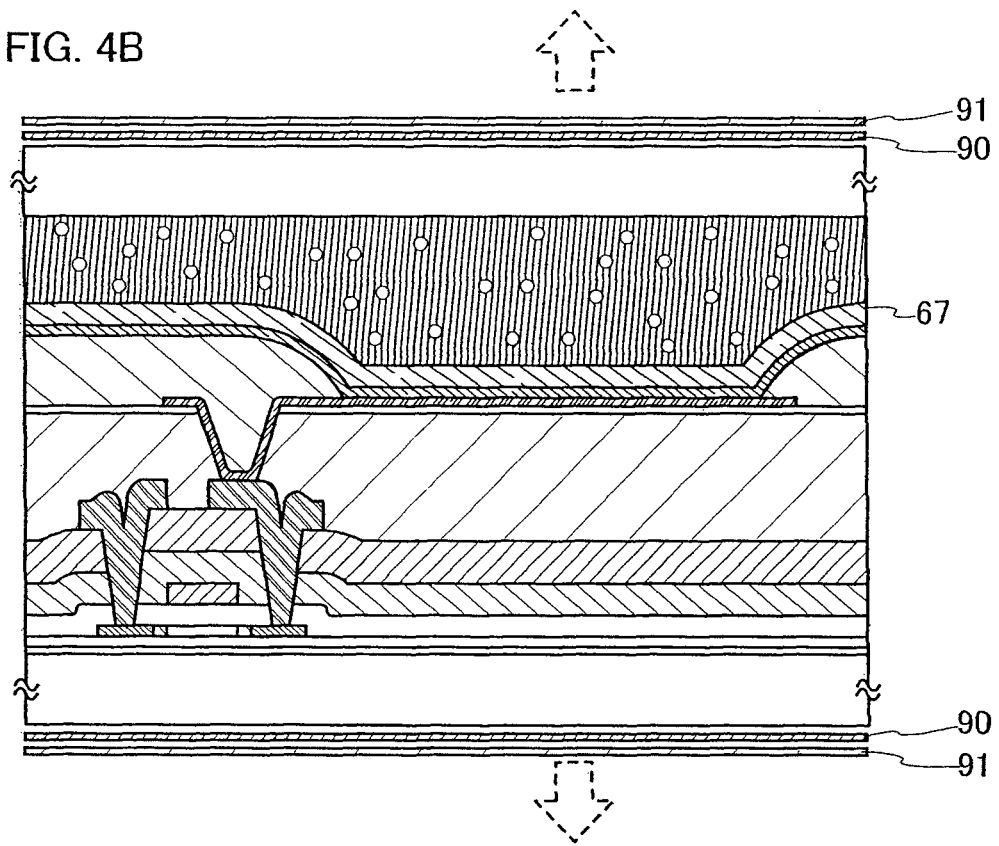

In FIG. 4B, each of the first electrode 64 and the second electrode 106 is formed with a light-transmitting conductive film and has a structure in which light can be extracted from both the substrate 50 and the counter substrate 94. With this structure, it is possible to prevent the screen from becoming transparent by respectively providing polarizing plates 90 outside the substrate 50 and the counter substrate 94, whereby increasing the visibility. A protective film 91 is preferably provided outside the polarizing plate 90.

Either an analog video signal or a digital video signal may be used in the light emitting device having a display function according to the present invention. The digital video signal includes a video signal using voltage and a video signal using current. When the light emitting element emits light, the video signal inputted into a pixel uses a constant voltage or a constant current. When the video signal uses a constant voltage, the voltage applied to the light emitting element or the current flowing in the light emitting element is constant. Meanwhile, when the video signal uses a constant current, the voltage applied to the light emitting element or the current flowing in the light emitting element is constant. The light emitting element to which the constant voltage is applied is driven by constant voltage driving, and the light emitting element in which the constant current flows is driven by the constant current driving. A constant current flows in the light emitting element driven by the constant current without being affected by the change in the resistance of the light emitting element. Any one of the driving methods described above can be used for a light emitting device and the driving method thereof according to the present invention.

A light emitting device having such a structure according to the present invention is highly reliable. A light emitting device having such a structure according to the present invention can provide blue light emission with good color purity. Further, a light emitting device having such a structure according to the present invention can provide good color reproducibility.

This embodiment can be combined with an appropriate structure of Embodiment 1 or Embodiment 2.

Embodiment 4

Figure 5A:
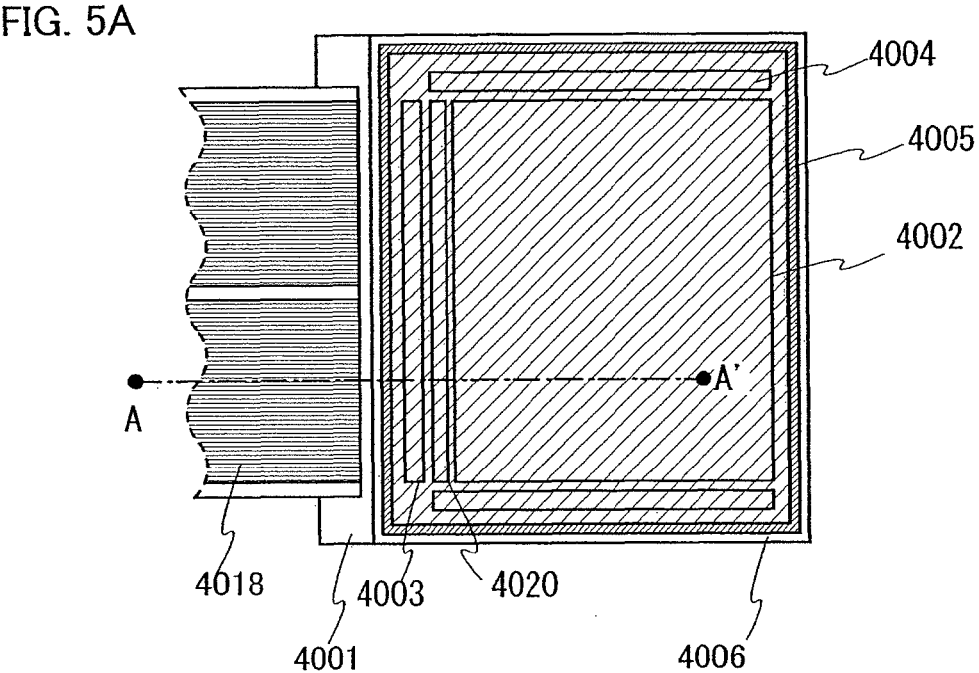
FIGS. 5A and 5B are a top view and a cross-sectional view of a light emitting device according to the present invention.
Figure 5B:
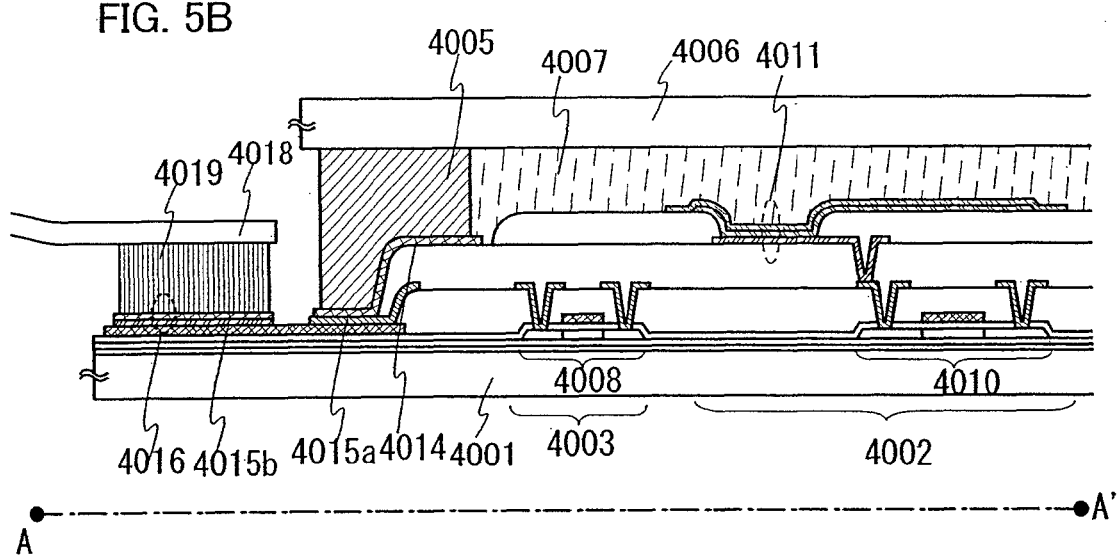

This embodiment will describe an appearance of a panel which is a light emitting device of the present invention with reference to FIGS. 5A and 5B. FIG. 5A is a top view of a panel in which a transistor and a light emitting element formed over a substrate are sealed with a sealing material formed between the substrate and a counter substrate 4006. FIG. 5B is a cross-sectional view corresponding to FIG. 5A. The light emitting element mounted on this panel has a structure as described in Embodiment 2.

A sealing material 4005 is provided so as to surround a pixel area 4002, a signal line driver circuit 4003, and a scan line driver circuit 4004 which are provided over a substrate 4001. In addition, the counter substrate 4006 is provided over the pixel area 4002, the signal line driver circuit 4003, and the scan line driver circuit 4004. Thus, the pixel area 4002, the signal line driver circuit 4003, and the scan line driver circuit 4004 together with the filler 4007 are sealed with the substrate 4001, the sealing material 4005, and the counter substrate 4006.

The pixel area 4002, the signal line driver circuit 4003, and the scan line driver circuit 4004 provided over the substrate 4001 have a plurality of thin film transistors. FIG. 5B shows a thin film transistor 4008 included in the signal line driver circuit 4003 and a thin film transistor 4010 included in the pixel area 4002.

The light emitting element 4011 is electrically connected to the thin film transistor 4010.

Further, a lead wiring 4014 corresponds to a wiring for supplying a signal or a power source voltage to the pixel area 4002, the signal line driver circuit 4003, and the scan line driver circuit 4004. The lead wiring 4014 is connected to a connection terminal 4016 via a lead wiring 4015. The connection terminal 4016 is electrically connected to a terminal of a flexible printed circuit (FPC) 4018 via an anisotropic conductive film 4019.

As the filler 4007, in addition to inert gas such as nitrogen or argon, an ultraviolet curable resin or a thermosetting resin can be used. For example, polyvinyl chloride, acrylic, polyimide, an epoxy resin, a silicone resin, polyvinyl butyral, or ethylene vinylene acetate can be used.

It is to be noted that the light emitting device according to the present invention includes in its category the panel in which the pixel area having the light emitting element is formed and a module in which an IC is mounted on the panel.

A light emitting device according to the invention as described above has a light emitting element described in Embodiment 2 as the light emitting element included in a pixel area, so that the pixel area of the light emitting device is highly reliable. Further, a light emitting device according to the invention as described above has a light emitting element described in Embodiment 2 as the light emitting element included in a pixel area, so that the light emitting device can provide blue light emission with good color purity. Further, a light emitting device according to the invention as described above has a light emitting element described in Embodiment 2 as the light emitting element included in a pixel area, so that the light emitting device can provide good color reproducibility and high display quality.

This embodiment can be used in appropriate combination with a structure of any one of Embodiment 1 to Embodiment 3.

Embodiment 5

This embodiment will describe a pixel circuit and a protective circuit in the panel and the module shown in Embodiment 4, and their operations. FIGS. 2A to 5B are cross sectional views of a driving TFT 1403 and a light emitting element 1405 in FIGS. 6A to 6F.

Figure 6A:
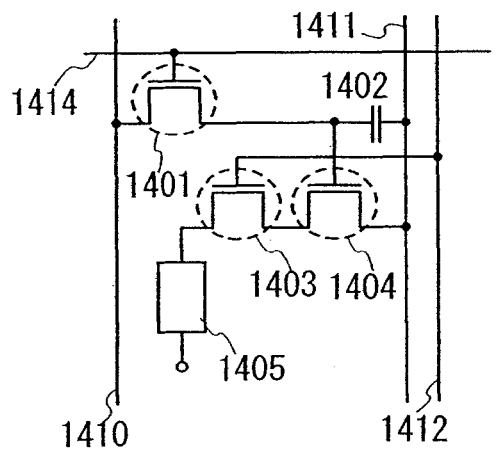
FIGS. 6A to 6F are figures showing examples of a pixel circuit of a light emitting device of the present invention.

A pixel shown in FIG. 6A includes a signal line 1410 and power source lines 1411 and 1412 in a column direction and a scan line 1414 in a row direction. The pixel further includes a switching TFT 1401, the driving TFT 1403, a current control TFT 1404, a capacitor 1402, and the light emitting element 1405.

Figure 6B:
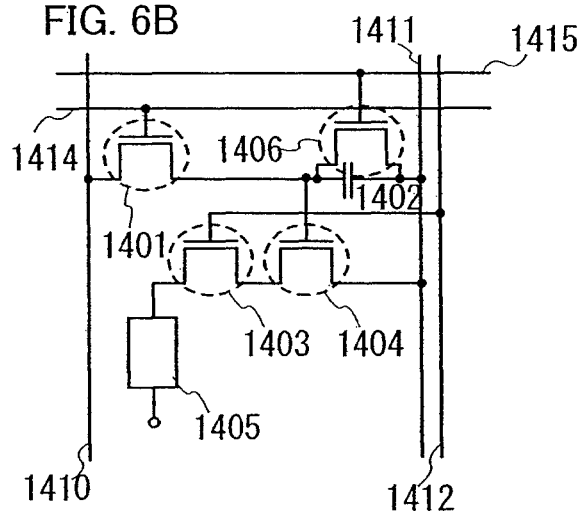
Figure 6C:
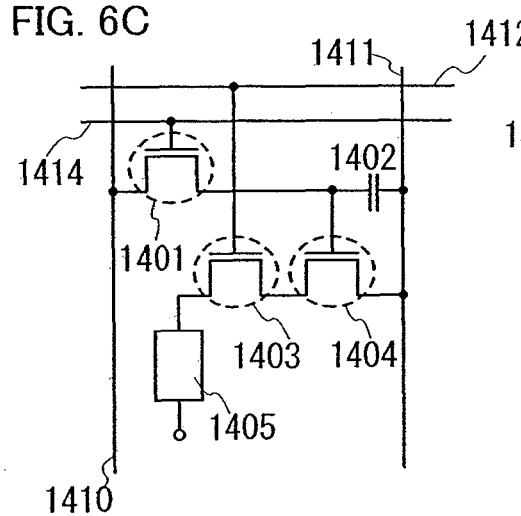
Figure 6D:
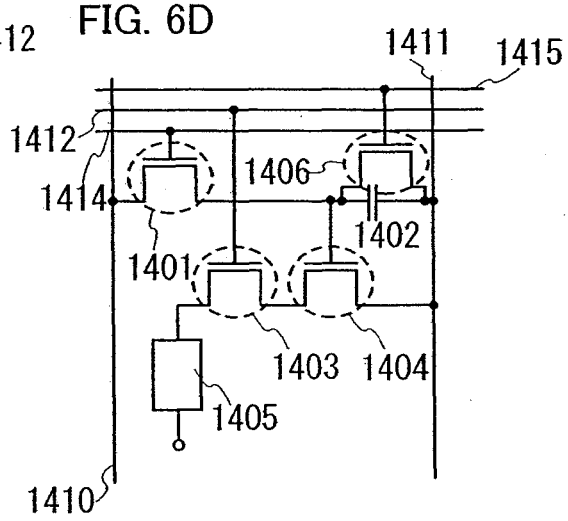

A pixel shown in FIG. 6C has the same structure as one in FIG. 6A except for that a gate electrode of the driving TFT 1403 is connected to the power source line 1412 provided in the row direction. In other words, the pixels shown in FIGS. 6A and 6C have the same equivalent circuit diagram. However, in the case of arranging the power source line 1412 in the column direction (FIG. 6A) and in the case of arranging the power source line 1412 in the row direction (FIG. 6C), each power source line is formed with a conductive film in different layers. Here, attention is paid to a wiring connected to the gate electrode of the driving TFT 1403, and the structure is shown separately in FIGS. 6A and 6C in order to show that these wirings are manufactured with different layers.

As a feature of the pixels shown in FIGS. 6A and 6C, the driving TFT 1403 and the current control TFT 1404 are connected serially within the pixel, and it is preferable to set the channel length L (1403) and the channel width W (1403) of the driving TFT 1403, and the channel length L (1404) and the channel width W (1404) of the current control TFT 1404 so as to satisfy L (1403)/W (1403):L (1404)/W (1404)=5 to 6000: 1.

The driving TFT 1403 operates in a saturation region and serves to control the current value of the current flowing into the light emitting element 1405. The current control TFT 1404 operates in a linear region and serves to control the current supply to the light emitting element 1405. Both TFTs preferably have the same conductivity type in the manufacturing step, and the TFTs are n-channel type TFTs in this embodiment. The driving TFT 1403 may be either an enhancement type or a depletion type. Since the current control TFT 1404 operates in the linear region in a light emitting device having the above structure according to the present invention, slight fluctuation of Vgs of the current control TFT 1404 does not affect the current value of the light emitting element 1405. That is to say, the current value of the light emitting element 1405 can be determined by the driving TFT 1403 operating in the saturation region. With the above structure, the unevenness of the luminance of the light emitting element due to the variation of the characteristic of the TFT can be improved, thereby providing a light emitting device in which the image quality is improved.

In the pixels shown in FIGS. 6A to 6D, the switching TFT 1401 is to control the input of the video signal to the pixel, and the video signal is inputted into the pixel when the switching TFT 1401 is turned on. Then, the voltage of the video signal is held in the capacitor 1402. Although FIGS. 6A and 6C show the structure in which the capacitor 1402 is provided, the present invention is not limited thereto. When the gate capacitance and the like can serve as a capacitor holding the video signal, the capacitor 1402 is not necessarily provided.

A pixel shown in FIG. 6B has the same pixel structure as that in FIG. 6A except for that a TFT 1406 and a scan line 1414 are added. In the same way, a pixel shown in FIG. 6D has the same pixel structure as that in FIG. 6C expect that the TFT 1406 and the scan line 1414 are added.

On and off of the TFT 1406 is controlled by the additionally provided scan line 1414. When the TFT 1406 is turned on, the charge held in the capacitor 1402 is discharged, thereby turning off the current control TFT 1404. In other words, by the provision of the TFT 1406, a state can be produced compellingly in which the current is not flowed into the light emitting element 1405. For this reason, the TFT 1406 can be referred to as an eraser TFT. Consequently, in the structures shown in FIGS. 6B and 6D, a lighting period can be started at the same time as or just after the start of a writing period before the writing of the signal into all the pixels; therefore the duty ratio can be increased.

Figure 6E:
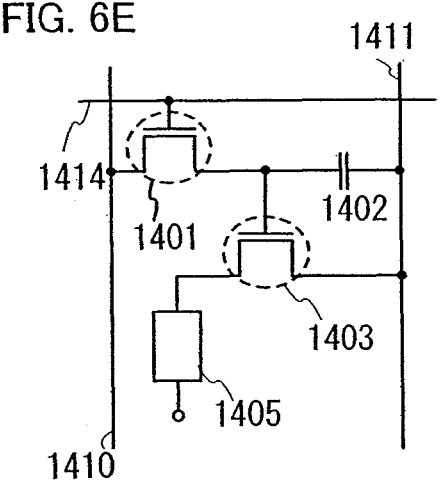
Figure 6F:
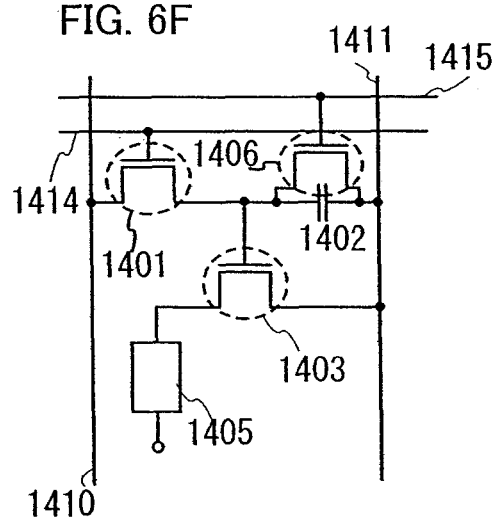

In a pixel shown in FIG. 6E, the signal line 1410 and the power source line 1411 are arranged in the column direction, and the scan line 1414 is arranged in the row direction. Further, the pixel includes the switching TFT 1401, the driving TFT 1403, the capacitor 1402, and the light emitting element 1405. A pixel shown in FIG. 6F has the same pixel structure as that shown in FIG. 6E except for that the TFT 1406 and a scan line 1415 are added. In the structure shown in FIG. 6F, the duty ratio can also be increased by the provision of the TFT 1406.

As thus described, various pixel circuits can be employed. In particular, in the case of forming a thin film transistor from an amorphous semiconductor film, the semiconductor film for the driving TFT 1403 is preferably large. In the case where the semiconductor is large, in the above pixel circuit, a top emission type is preferable in which light from a light emitting stack is emitted from the sealing substrate side.

Such an active matrix light emitting device can be driven at low voltage when the pixel density increases, because the TFTs are provided in respective pixels. Therefore, it is considered that the active matrix light emitting device is advantageous.

Although this embodiment describes the active matrix light emitting device in which the respective TFTs are provided in respective pixels, a passive matrix light emitting device can also be formed in which TFTs are provided in each column. Since the TFTs are not provided in respective pixels in the passive matrix light emitting device, high aperture ratio can be obtained. In the case of a light emitting device in which light is emitted to both sides of the light emitting stack, the transmissivity of the passive matrix light emitting device is increased.

Subsequently, a case in which a diode is provided as a protective circuit on the scan line and the signal line with the use of an equivalent circuit shown in FIG. 6E will be described.

Figure 7:
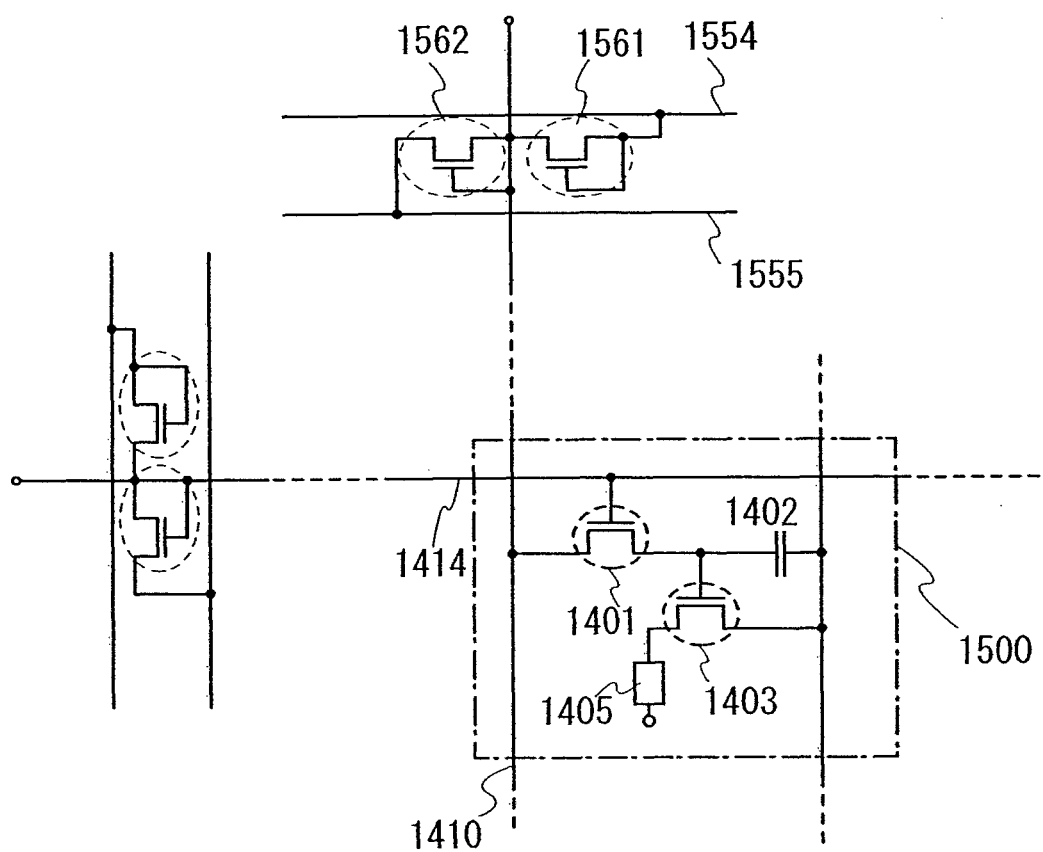
FIG. 7 is a figure showing an example of a protective circuit of a light emitting device according to the present invention.

In FIG. 7, the switching TFT 1401, the driving TFT 1403, the capacitor 1402, and the light emitting element 1405 are provided in a pixel area 1500. Diodes 1561 and 1562 are provided to the signal line 1410. In the similar way to the switching TFT 1401 and the driving TFT 1403, the diodes 1561 and 1562 are manufactured based on the above embodiments, and have a gate electrode, a semiconductor layer, a source electrode, a drain electrode, and the like. The diodes 1561 and 1562 are operated as diodes by connecting the gate electrode with the drain electrode or the source electrode.

Wirings 1554 and 1555 connecting to the diodes are formed with the same layer as the gate electrode. Therefore, in order to connect the wirings 1554 and 1555 with the source electrode or the drain electrode of the diode, it is necessary to form a contact hole in the gate insulating layer.

A diode provided on the scan line 1414 has the similar structure.

As thus described, according to the present invention, a protective diode to be provided on an input stage can be manufactured simultaneously. The position at which the protective diode is formed is not limited to this, and the diode may also be provided between the driver circuit and the pixel.

This embodiment can be appropriately combined with a suitable structure of Embodiments 1 to 4.

A light emitting device having such a protective circuit according to the present invention is highly reliable, capable of providing better color purity of blue light emission, and can provide better color reproducibility. Further, with the above structure, the reliability as a light emitting device can be further improved.

Embodiment 6

As an electronic device according to the present invention to which a light emitting device according to the present invention (module) is mounted, the following is given; a camera such as a video camera or a digital camera, a goggle type display (head mount display), a navigation system, a sound reproduction device (car audio component or the like), a computer, a game machine, a mobile information terminal (a mobile computer, a mobile telephone, a mobile game machine, an electronic book, or the like), an image reproduction device equipped with a recording medium (specifically a device which reproduces the recording medium such as a digital versatile disc (DVD) and which is equipped with a display for displaying the image), or the like. FIGS. 8A to 8E show specific examples of those electronic appliances.

Figure 8A:
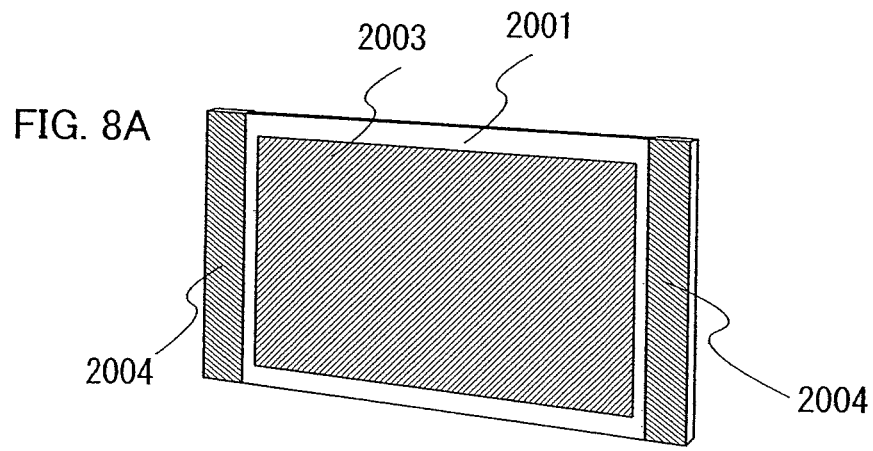
FIGS. 8A to 8E are figures showing examples of electronic device to which the present invention can be applied.

FIG. 8A shows a light emitting device, which corresponds to, for example, a television receiving device or a monitor of a personal computer. The light emitting device according to the present invention includes a case 2001, a display area 2003, speaker portions 2004, and the like. In the light emitting device according to the present invention, color reproducibility of the display area 2003 is good and the display quality is high. In the pixel area, a polarizing plate or a circular polarizing plate is preferably provided in the pixel area to improve the contrast. For example, films are preferably provided in the order of a quarter wave-plate, a half wave-plate, and a polarizing plate on a sealing substrate. Further, an anti-reflection film may be provided over the polarizing plate.

Figure 8B:
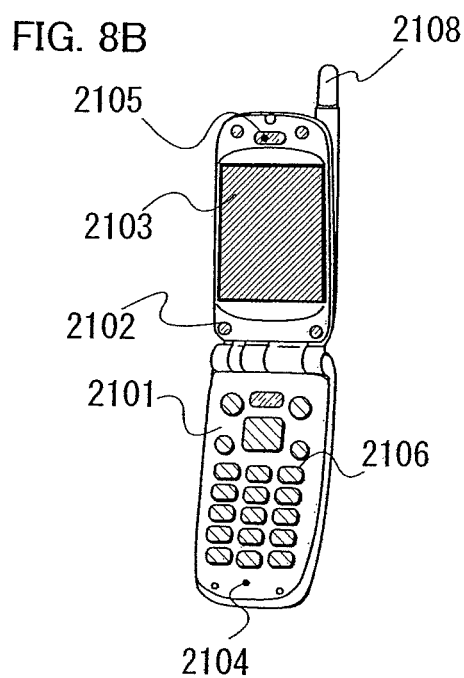

FIG. 8B shows a mobile phone including a main body 2101, a case 2102, a display area 2103, an audio input portion 2104, an audio output portion 2105, operation keys 2106, an antenna 2108, and the like. In the mobile phone according to the present invention, color reproducibility of the display area 2103 is good and the display quality is high.

Figure 8C:
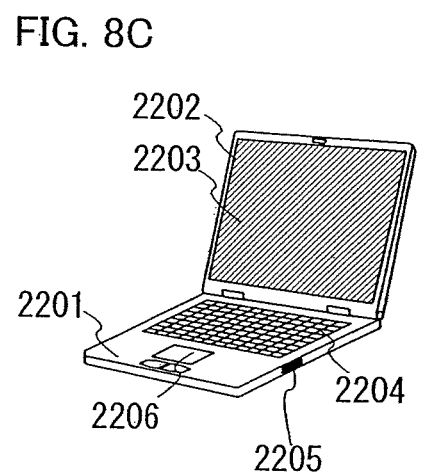

FIG. 8C shows a computer including a main body 2201, a case 2202, a display area 2203, a keyboard 2204, an external connection portion 2205, a pointing mouse 2206, and the like. In the computer according to the present invention, color reproducibility of the display area 2203 is good and the display quality is high. Although FIG. 9C shows a laptop computer, the present invention is also applicable to a desktop computer in which a display area is equipped with a hard disk.

Figure 8D:
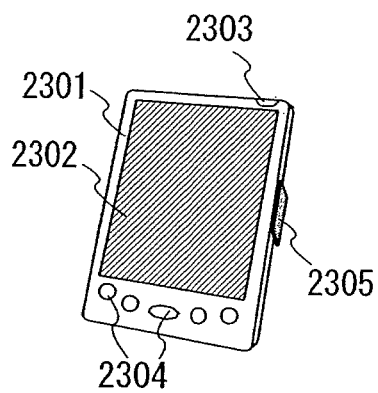

FIG. 8D shows a mobile computer including a main body 2301, a display area 2302, a switch 2303, operation keys 2304, an infrared port 2305, and the like. In the mobile computer according to the present invention, the display quality of the display area 2302 is high.

Figure 8E:
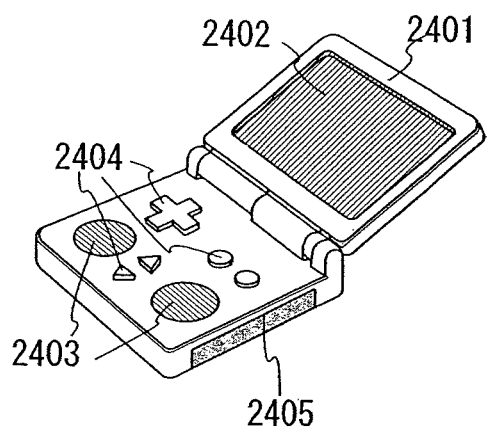

FIG. 8E shows a mobile game machine including a case 2401, a display area 2402, speaker portions 2403, operation keys 2404, an recording medium insert portion 2405, and the like. In of the mobile game machine according to the present invention, color reproducibility of the display area 2402 is good and the display quality is high.

As thus described, the present invention can be widely applied, and can be used in electronic appliances of every field.

This embodiment can be appropriately combined with a suitable structure of Embodiments 1 to 5.

EXAMPLE 1

As an example of a material according to the invention, a synthetic method of a compound represented by formula (11) 9-[4-(N-carbazolyl)] phenyl-10-phenylanthracene (hereinafter referred to as CzPA) below will be described.

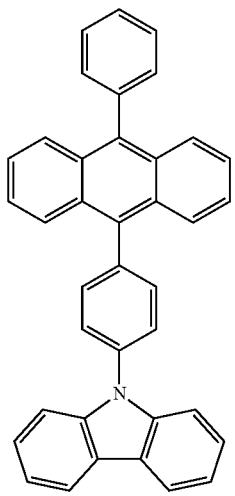

(11)

First, a synthetic method of 9-phenylanthracene will be described. 5.4 g (21.1 mmol) of 9-bromoanthracene, 2.6 g (21.1 mmol) of phenylboronic acid, 260 mg (0.21 mmol) of palladium acetate, 10 mL of 2M potassium carbonate solution, 263 mg (0.84 mmol) of tri(ortho-tolyl)phosphine, and dimethoxyethane (20 mL) are agitated at 80° C. for nine hours. After the reaction, precipitated solid was collected by filtration under reduced pressure, thereafter dissolved in toluene, and then filtered through Florisil, celite, and alumina. After the filtrate is rinsed with water and saturated salt solution, it is dried with magnesium sulfate. After the natural filtration, when the filtrate is condensed, 4.0 g of 9-phenylanthracene is obtained as a light brown solid at a yield of 75%. A synthetic scheme of 9-phenylanthracene from 9-bromo anthracene is described below.

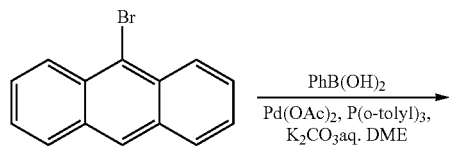

-continued

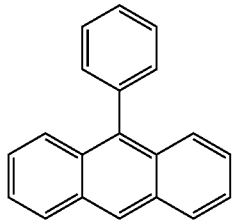

Next, a synthetic method of 9-bromo-10-phenylanthracene from 9-phenylanthracene will be described. 6.0 g (23.7 mmol) of 9-phenylanthracene prepared by the above method is dissolved in 80 mL of carbon tetrachloride, carbon tetrachloride solution (10 mL) containing 3.80 g (21.1 mmol) of boron is dropped from a dropping funnel into the reaction solution. After the dropping, it is agitated at room temperature. A sodium thiosulfate solution is added to stop the reaction. The organic layer is rinsed with sodium hydroxide solution and saturated salt solution, and dried with magnesium sulfate. After natural filtration, it is condensed and dissolved in toluene, and filtered through Florisil, celite. When the filtrate is condensed, and recrystallized with dichloromethane and hexane, 7.0 g of 9-bromo-10-phenylanthracene is obtained as a light yellow solid at a yield of 89%. A synthetic scheme of 9-bromo-10-phenylanthracene from 9-phenylanthracene is shown below.

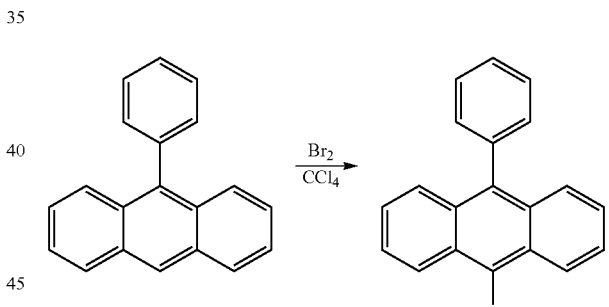

Next, a synthetic method of 9-iodo-10-phenylanthracene using 9-bromo-10-phenylanthracene prepared by the above method as a starting material will be shown. 3.33 g (10 mmol) of 9-bromo-10-phenylanthracene was dissolved in THF 80 mL, and cooled to −78° C., and n-BuLi (1.6 M, 7.5 mL, 12.0 mmol) is thereafter dropped and agitation is carried out for one hour. Subsequently, THF solution (20 mL) containing 5 g (20.0 mmol) of iodine is dropped at −78° C., and agitated for 2 hours. After the reaction, a sodium thiosulfate solution is added to stop the reaction. The organic layer is rinsed with sodium thiosulfate solution and saturated salt solution, and dried with magnesium sulfate. After natural filtration, when the filtrate is condensed and thereafter recrystallized with ethanol, 3.1 g of 9-iodo-10-phenylanthracene is obtained as a light yellow solid at a yield of 83%. A synthetic scheme of 9-iodo-10-phenylanthracene from 9-bromo-10-phenylanthracene is shown below.

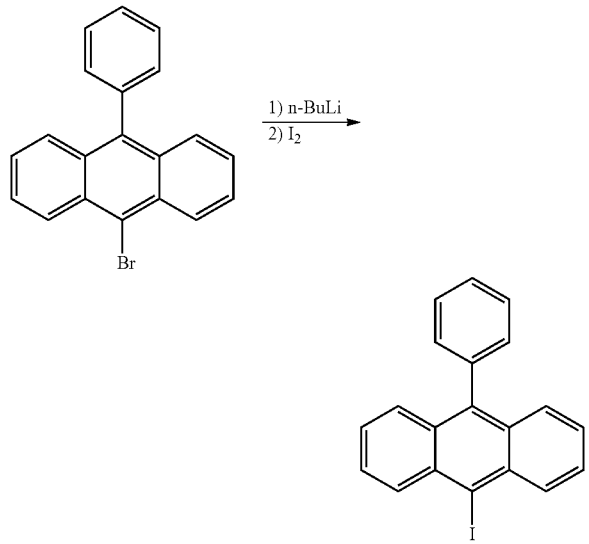

Next, a synthetic method of 9-phenyl-10-(4-bromophenyl) anthracene using 9-iodo-10-phenylanthracene prepared by the above method as a starting material will be shown. A mixture of 1.0 g (2.63 mmol) of 9-iodo-10-phenylanthracene, 542 mg (2.70 mmol) of p-bromo phenylboronic acid, 46 mg (0.03 mmol) of tetrakis (triphenylphosphine) palladium, 2M potassium carbonate solution (3 mL), and 10 mL of toluene is agitated at 80° C. 9 hours. After reaction, toluene is added and filtration is carried out using Florisil, celite, and alumina. After the filtrate is rinsed with water and saturated salt solution, it is dried with magnesium sulfate. After natural filtration, the filtrate is condensed, and when it is recrystallized with chloroform and hexane, 562 mg of 9-phenyl-10-(4-bromophenyl) anthracene is obtained as a light brown solid at a yield of 45%. A synthetic scheme of 9-phenyl-10-(4-bromophenyl) anthracene from 9-iodo-10-phenylanthracene is shown below.

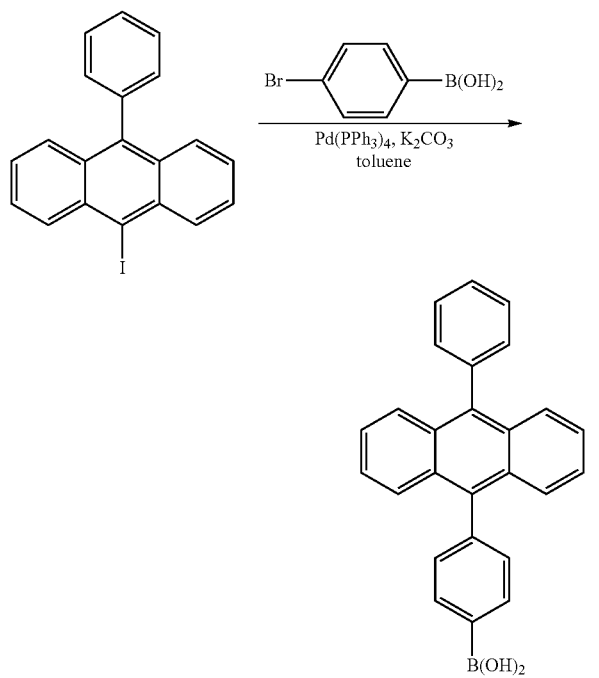

Next, a synthetic method of CzPA using 9-phenyl-10-(4-bromophenyl) anthracene phenylanthracene prepared by the above method as a starting material will be shown. A mixture of 1.3 g (3.2 mmol) of 9-phenyl-10-(4-bromophenyl) anthracene, 578 mg (3.5 mmol) of carbazole, 50 mg (0.017 mmol) dibenzylidine palladium (II), 1.0 mg (0.010 mmol) of t-butoxy sodium, 0.1 mL of tri(t-butylphosphine), and 30 mL of toluene is heated to reflux at 110° C. for 10 hours. After the reaction, the solution is rinsed with water, aqueous layer is extracted with toluene, and it is rinsed together with the organic layer using saturated salt solution, and thereafter dried with magnesium sulfate. An oily product obtained by natural filtration and condensation is purified with silica gel column chromatography (hexane:toluene=7:3), and recrystallized using dichloromethane and hexane to obtain 1.5 g of CzPA which is the desired product at a yield of 93%. Purification of 5.50 g of the obtained CzPA is conducted by sublimation under conditions of at 270° C., under a stream of argon (flow rate: 3.0 ml/min), at a pressure of 6.7 Pa for 20 hours; thus, 3.98 g is recovered and the recovery was 72%. A synthetic scheme of CzPA from 9-phenyl-10-(4-bromophenyl) anthracene is shown below.

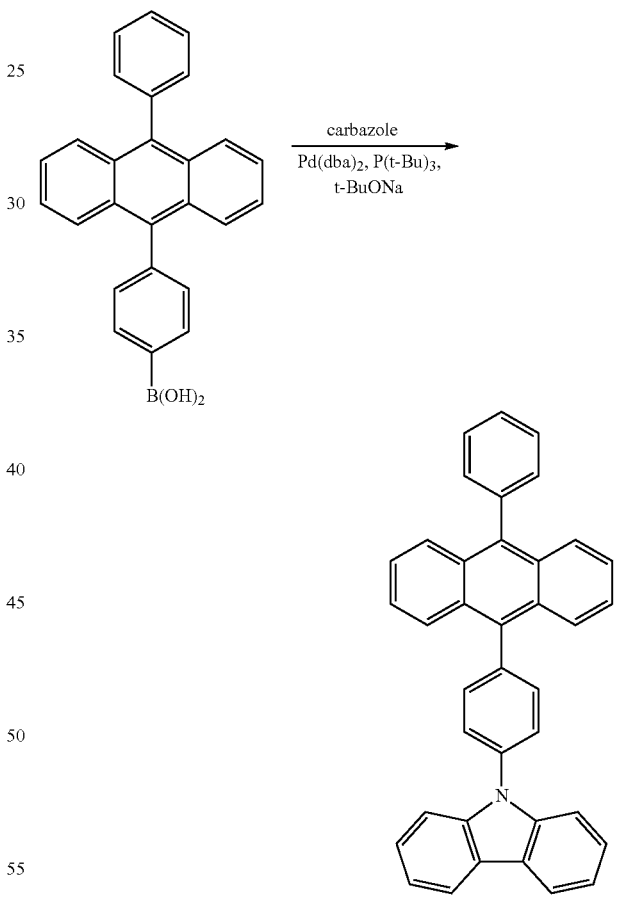

Figure 9:
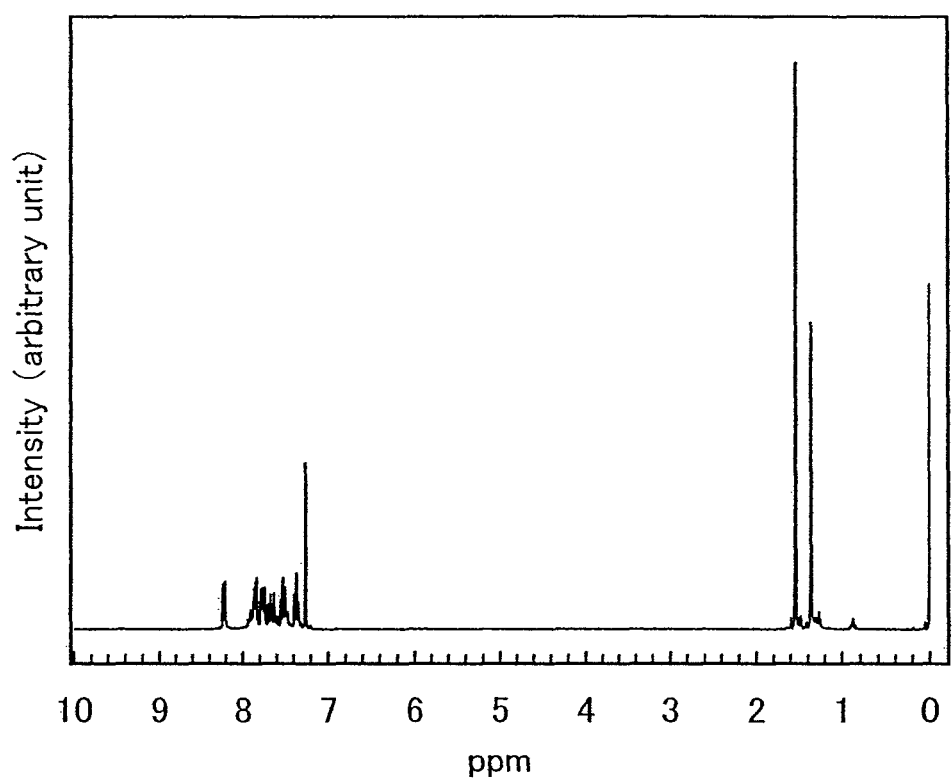
FIG. 9 shows $^1$H NMR spectrum of CzPA.

NMR data of the obtained CzPA is shown below. $^1$H NMR (300 MHz, CDCl$_3$); δ=8.22 (d, J=7.8 Hz, 2H), 7.86-7.82 (m, 3H), 7.61-7.36 (m, 20H). Further, the chart of $^1$H NMR is shown in FIG. 9.

CzPA is a light brown powdery solid. Thermogravimetry-differential thermal analysis (TG-DTA) of the obtained CzPA is conducted. Note that a thermogravimetry-differential thermal analysis apparatus (TG/DTA SCC 5200 manufactured by Seiko Instruments Inc.) is used to measure the CzPA. Thermophysical properties are evaluated under a nitrogen atmosphere with a rising temperature of 10° C./min. Consequently, based on gravity-temperature relationship (thermogravimetric measurement), the decomposing temperature under normal pressure was 348° C. that is the temperature at which the gravity was 95% or less of the gravity at the starting point of the measurement. The glass transition temperature and the melting point of the obtained compound CzPA is examined with a differential scanning calorimeter (Pyris 1 DSC manufactured by Perkin Elmer Co., Ltd.). The results are 125° C. and 305° C. respectively; thus, CzPA is proved to be thermally stable.

Figure 10:
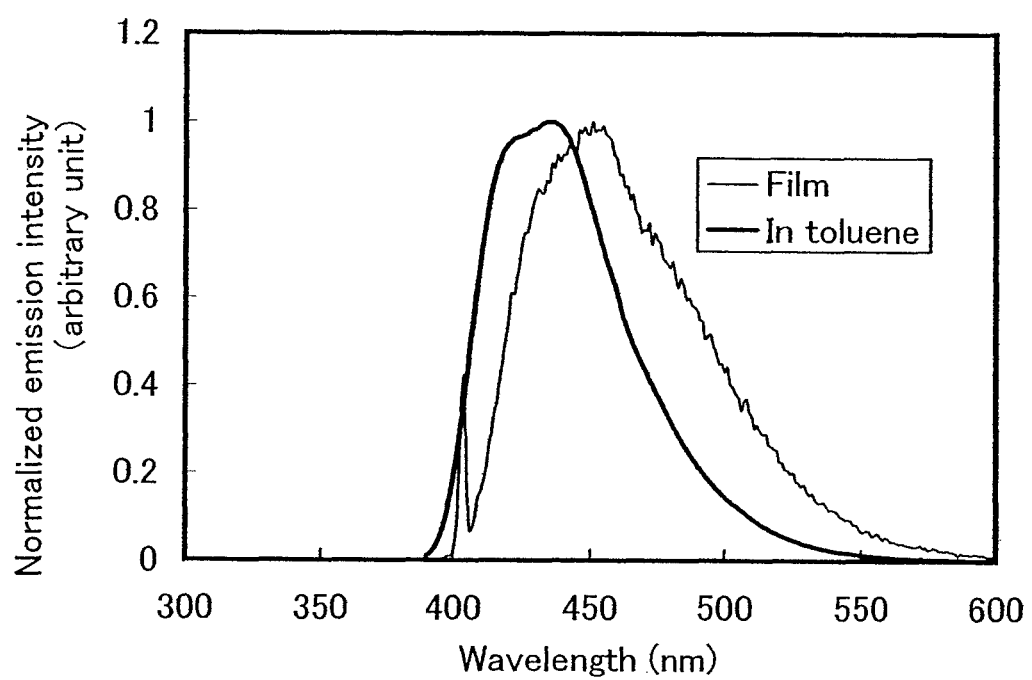
FIG. 10 shows light emitting spectrum in a thin film of CzPA and toluene.

An absorption spectrum of toluene solution of CzPA and a thin film state of CzPA are measured. The absorption of the toluene solution of CzPA and thin film state of CzPA based on anthracene are observed at about 390 nm and 400 nm, respectively. In addition, FIG. 10 shows emission spectrum of toluene solution of CzPA and the thin film state of CzPA. In FIG. 10, the horizontal axis indicates a wavelength (nm) and the vertical axis indicates emission intensity (arbitrary unit). It can be found that the maximum emission wavelength of toluene solution and the thin film state of CzPA are 448 nm (excitation wavelength 370 nm) and 451 nm (excitation wavelength 370 nm), respectively, and thus, blue light emission can be obtained.

HOMO level and LUMO level in the thin film state of CzPA are measured. The value of HOMO level is obtained by converting a value of the ionization potential measured with a photoelectron spectroscopy device (AC-2 manufactured by Riken Keiki Co., Ltd) to a negative value. The value of LUMO level is obtained by adding an energy gap between absorption edges of the thin film to a value of HOMO level. As a result, HOMO level and LUMO level are −5.64 eV and −2.71 eV, respectively and thus the extremely large band gap of 2.93 eV is obtained.

EXAMPLE 2

As an example of a material according to the invention, a synthetic method of a compound represented by formula (59) 9-[4-(3,6-diphenyl-N-carbazolyl)] phenyl-10-phenylanthracene (hereinafter referred to as DPCzPA) below will be described.

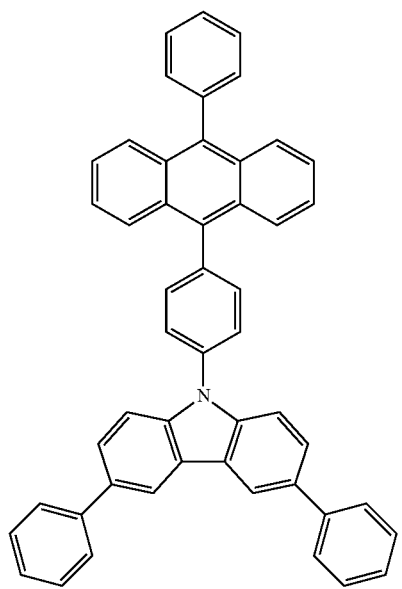

(59)

This compound is prepared in accordance with the synthetic method shown below. Note that 9-phenyl-10-(4-bromophenyl) anthracene is prepared in the manner shown in Example 1.

First, a synthetic method of 3,6-dibromocarbazole will be shown below. A mixture of 6.5 g (20.0 mmol) 3,6-dibromocarbazole, 5.0 g (41.0 mmol) of phenylboronic acid, 93 mg (0.40 mmol) of palladium acetate, 6.9 g (5.2 mmol) of potassium carbonate, water (25 mL), 610 mg of tri(ortho-tolyl) phosphine, and dimethoxyethane (50 mL) is heated to reflux at 80° C. for 3.5 three hours. After the reaction, the solution is rinsed with water, aqueous layer is extracted with toluene, and it is rinsed together with the organic layer using saturated salt solution, and thereafter dried with magnesium sulfate. After natural filtration, the filtrate is condensed to obtain 4.1 g of 3,6-di(2-phenyl-phenyl)-carbazoleas a white solid at a yield of 63%. A synthetic scheme of 3,6-di(2-phenyl-phenyl)-carbazoleis shown below.

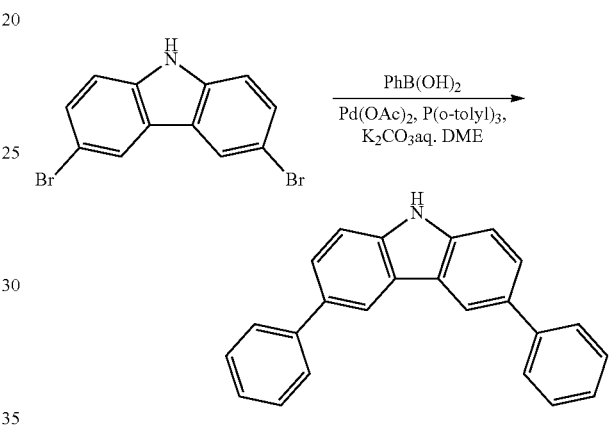

Next, a synthetic method of DPCzPA by coupling reaction of 3, 6-diphenylcarbazole and 9-phenyl-10-(4-bromophenyl) anthracene will be shown. A mixture of 819 mg (2.0 mmol) of 9-phenyl-10-(4-bromophenyl) anthracene, 666 mg (2.1 mmol) of 3,6-diphenylcarbazole, 14 mg (0.02 mmol) of dibenzylidine palladium (II), 1.0 g (10 mmol) of t-butoxy sodium, 0.1 mL of tri(t-butyl) phosphine, 20 mL of toluene is refluxed at 110° C. for 10 hours. After the reaction, the solution is rinsed with water, aqueous layer is extracted with toluene, and it is rinsed together with the organic layer using saturated salt solution, and thereafter dried with magnesium sulfate. An oily product obtained by natural filtration and condensation is dissolved in toluene, and filtered through celite, Florisil, and alumina. The filtrate is condensed, and purified by silica gel column chromatography (toluene). Recrystallization is carried out using dichloromethane and hexane to obtain 937 mg of DPCzPA at a yield of 71%. A synthetic scheme of DPCzPA by coupling reaction of 3,6-diphenylcarbazole and 9-phenyl-10-(4-bromophenyl) anthracene is shown below.

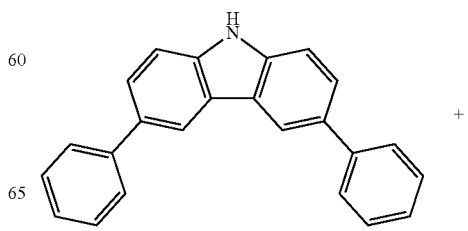

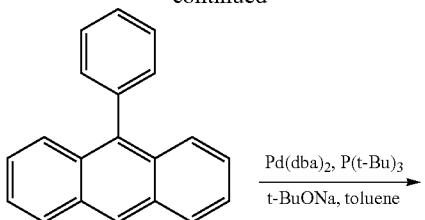

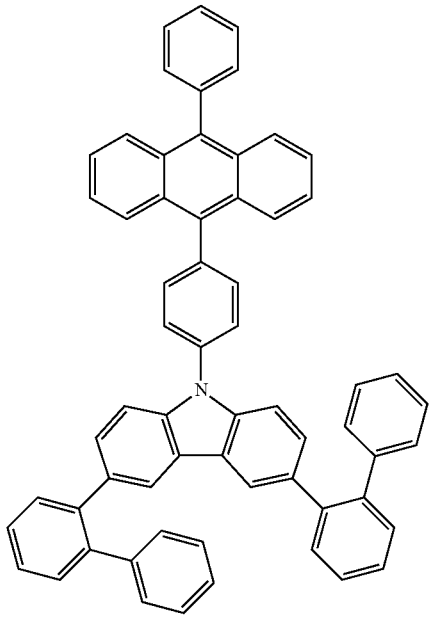

Figure 11:
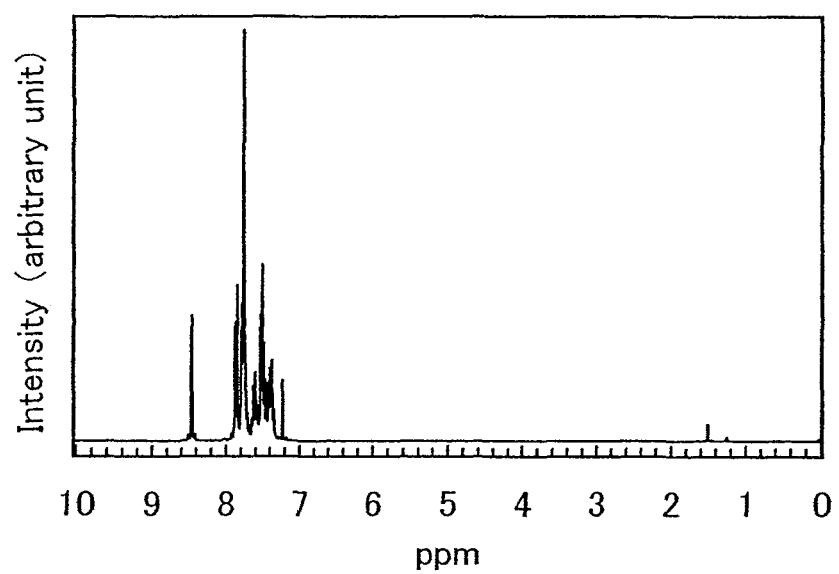
FIG. 11 shows $^1$H NMR spectrum of DPCzPA.
Figure 12:
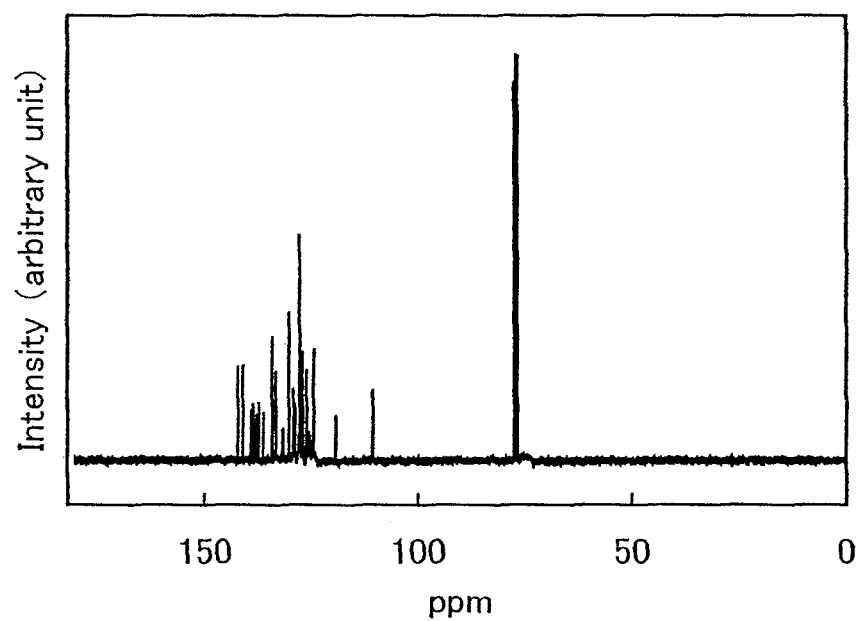
FIG. 12 shows $^{13}$C NMR spectrum of DPCzPA.

NMR data of DPCzPA is shown below. $^1$H NMR (300 MHz, CDCl$_3$); δ=8.47 (s, 2H), 7.91-7.86 (m, 3H), 7.80-7.75 (m, 12H), 7.64-7.38 (m, 16H). $^{13}$C NMR (75 MHz, CDCl$_3$); δ=141.9, 140.7, 138.9, 138.4, 137.6, 137.0, 135.9, 133.8, 132.9, 131.3, 129.9, 128.8, 128.5, 127.6, 127.3, 127.2, 126.7, 125.8, 125.4, 125.3, 125.2, 125.1, 124.2, 119.0, 118.9, 110.3. Further, the $^1$H NMR chart and $^{13}$C NMR chart of the obtained DPCzPA are respectively shown in FIG. 11 and FIG. 12.

DPCzPA is a light yellow powdery solid. Thermogravimetry-differential thermal analysis (TG-DTA) of DPCzPA was conducted. A thermogravimetry-differential thermal analysis apparatus (TG/DTA SCC 5200 manufactured by Seiko Instruments Inc.) is used to measure the DPCzPA. Thermophysical properties are evaluated under a nitrogen atmosphere with a rising temperature of 10° C./min. Consequently, based on gravity-temperature relationship (thermogravimetric measurement), the decomposing temperature under normal pressure is 431° C.

Figure 13:
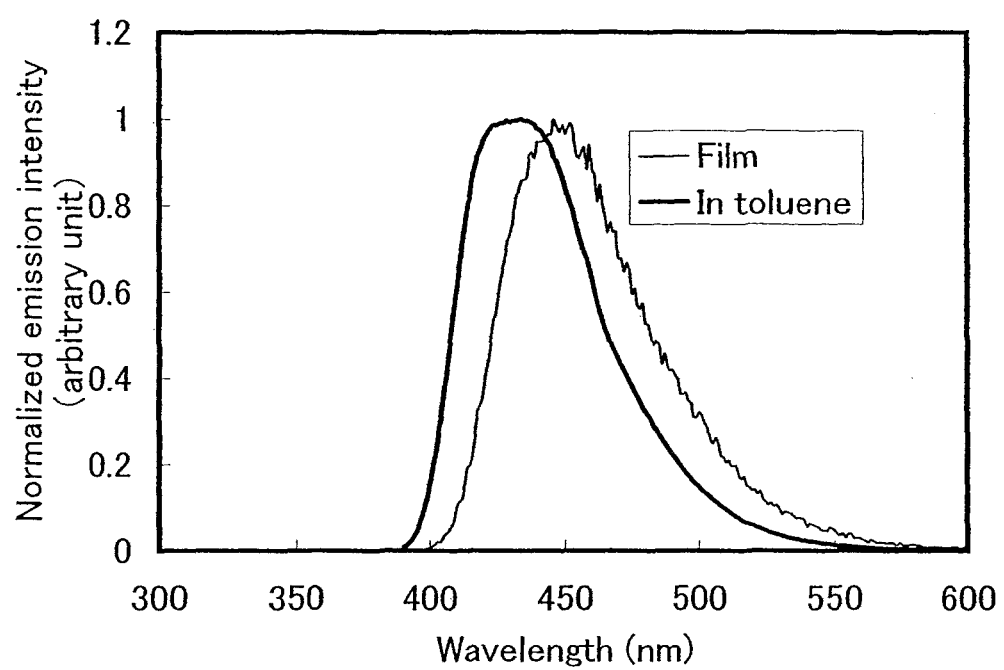
FIG. 13 shows light emitting spectrum in a thin film of DPCzPA and toluene.

An absorption spectrum of toluene solution of DPCzPA and a thin film state of DPCzPA are measured. The absorption of the toluene solution of DPCzPA and thin film state of DPCzPA based on anthracene are observed at about 390 nm and 380 nm, respectively. In addition, FIG. 13 shows emission spectrum of toluene solution of DPCzPA and the thin film state of DPCzPA. In FIG. 13, the horizontal axis indicates a wavelength (nm) and the vertical axis indicates emission intensity (arbitrary unit). It can be found that the maximum emission wavelength of toluene solution and the thin film state of DPCzPA are 440 nm (excitation wavelength 370 nm) and 446 nm (excitation wavelength 380 nm), respectively, and thus, blue light emission can be obtained.

HOMO level and LUMO level in the thin film state of DPCzPA are measured. The value of HOMO level is obtained by converting a value of the ionization potential measured with a photoelectron spectroscopy device (AC-2 manufactured by Riken Keiki Co., Ltd) to a negative value. The value of LUMO level is obtained by adding an energy gap between absorption edges of the thin film to a value of HOMO level. As a result, HOMO level and LUMO level are −5.75 eV and −2.77 eV, respectively and thus the extremely large band gap of 2.98 eV is obtained.

EXAMPLE 3

As an example of a material according to the invention, a synthetic method of a compound represented by formula (67) 9-{4-[3,6-di(2-phenyl)phenyl-N-carbazolyl]phenyl}-10-phenylanthracene (hereinafter referred to as BPCzPA) below will be described. Note that 9-phenyl-10-(4-bromophenyl) anthracene is prepared in the manner shown in Example 1.

(67)

First, a synthetic method of 3,6-di(2-phenyl-phenyl)-carbazole will be shown below. A mixture of 3.25 g (10.0 mmol) 3,6-dibromocarbazole, 4.2 g (21.0 mmol) of o-biphenylboronic acid, 50 mg (0.21 mmol) of palladium acetate, 6.9 g (5.2 mmol) of potassium carbonate, water (25 mL), 308 mg (1.0 mmol) of tri(ortho-tolyl) phosphine, and 30 mL of dimethoxyethane is heated to reflux at 80° C. for 3.5 three hours. After the reaction, the solution is rinsed with water, aqueous layer is thereafter extracted with toluene, and it is rinsed together with the organic layer using saturated salt solution, and thereafter dried with magnesium sulfate. After natural filtration, the filtrate is condensed to obtain 2.2 g of 3,6-di(2-phenyl-phenyl)-carbazole as a white solid at a yield of 46%. A synthetic scheme of 3,6-di(2-phenyl-phenyl)-carbazole is shown below.

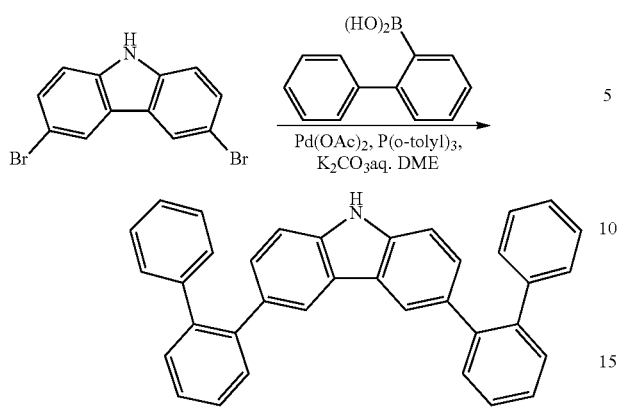

Next, a synthetic method of BPCzPA by coupling reaction of 3,6-di(2-phenyl-phenyl)-carbazole and 9-phenyl-10-(4-bromophenyl) anthracene will be shown. A mixture of 550 mg (1.34 mmol) of 9-phenyl-10-(4-bromophenyl) anthracene, 644 mg (1.35 mmol) of 3,6-di(2-phenyl-phenyl)-carbazole, 58 mg (0.09 mmol) of dibenzylidine palladium (II), 534 mg (2.47 mmol) of t-butoxy sodium, 0.1 mL of tri(t-butylphosphine), 10 mL of toluene is heated to reflux at 110° C. for 5.5 hours. After the reaction, the solution is rinsed with water, aqueous layer is extracted with toluene, and it is rinsed together with the organic layer using saturated salt solution, and thereafter dried with magnesium sulfate. An oily product obtained by natural filtration and condensation is dissolved in toluene, and filtered through celite, Florisil, and alumina. The filtrate is condensed, and purified by silica gel column chromatography (hexane:toluene=7:3). Recrystallization is carried out using dichloromethane and hexane to obtain 703 mg of BPCzPA as a light yellow powdery solid at a yield of 65%. A synthetic scheme of BPCzPA by coupling reaction of 3,6-di(2-phenyl-phenyl)-carbazole and 9-phenyl-10-(4-bromophenyl) anthracene is shown below.

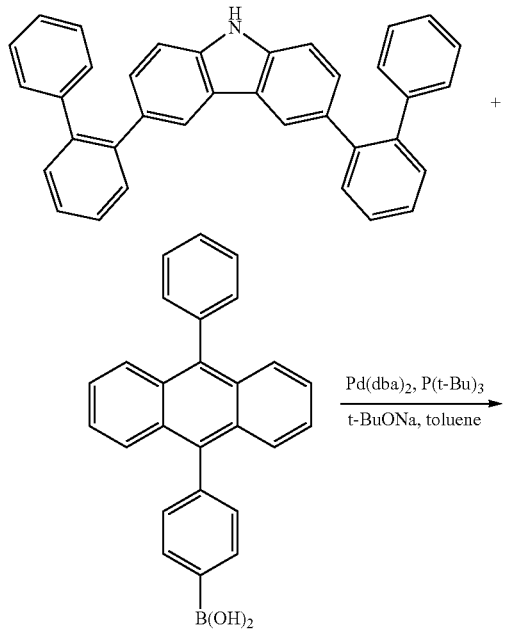

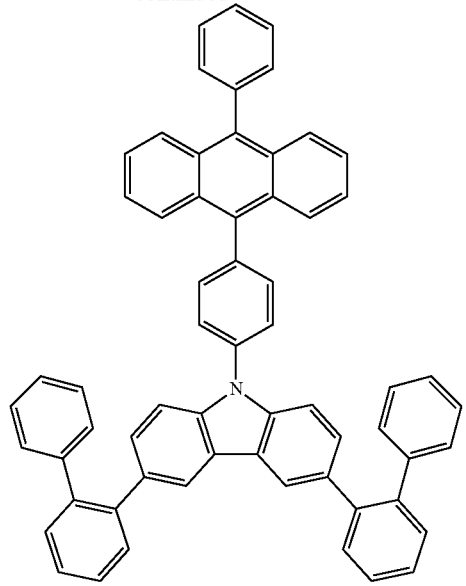

Figure 14:
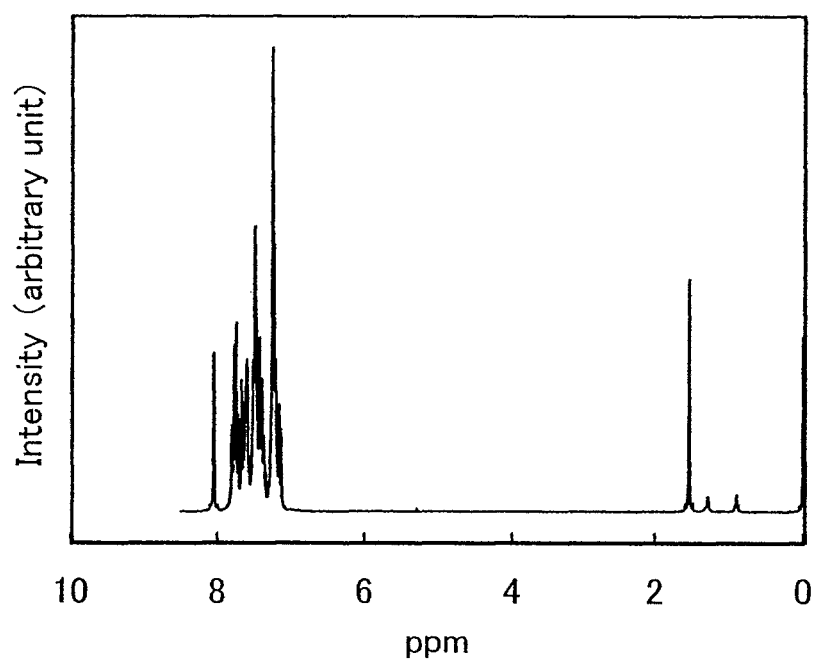
FIG. 14 shows $^1$H NMR spectrum of BPCzPA.
Figure 15:
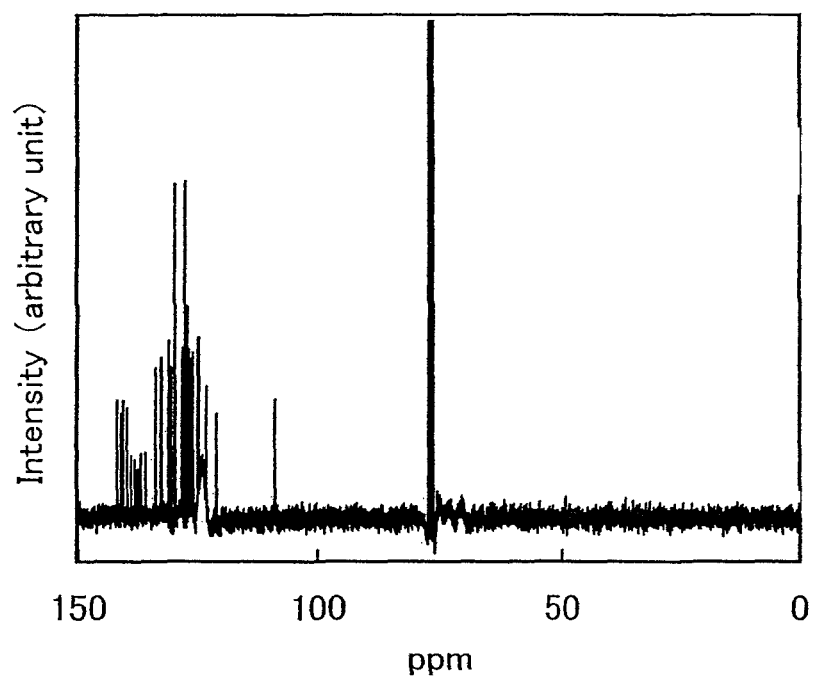
FIG. 15 shows $^{13}$C NMR spectrum of BPCzPA.

NMR data of BPCzPA is shown below. $^1$H NMR (300 MHz, CDCl$_3$); δ=8.09 (s, 2H), 7.80-7.34 (m, 28H), 7.23-7.12 (m, 11H). $^{13}$C NMR (75 MHz, CDCl$_3$); δ=141.9, 141.1, 140.7, 139.8, 138.9, 138.1, 137.5, 136.9, 135.9, 133.8, 132.7, 131.3, 131.2, 130.8, 130.0, 129.91, 129.90, 129.8, 128.6, 128.4, 128.0, 127.5, 127.2, 127.1, 126.7, 126.6, 126.3, 125.3, 125.1, 123.5, 121.3, 109.2. Further, the $^1$H NMR chart and $^{13}$C NMR chart of the obtained BPCzPA are respectively shown in FIG. 14 and FIG. 15.

BPCzPA was a light yellow powdery solid. Thermogravimetry-differential thermal analysis (TG-DTA) of BPCzPA is conducted. A thermogravimetry-differential thermal analysis apparatus (TG/DTA SCC 5200 manufactured by Seiko Instruments Inc.) is used to measure the BPCzPA. Thermophysical properties are evaluated under a nitrogen atmosphere with a rising temperature of 10° C./min. Consequently, based on gravity-temperature relationship (thermogravimetric measurement), the temperature under normal pressure where reduction of the gravity starts is 445° C. Further, the glass transition temperature and the melting point of the obtained compound BPCzPA is examined with a differential scanning calorimeter (Pyris 1 DSC manufactured by Perkin Elmer Co., Ltd.). The results are 167° C. and 330° C. respectively; thus, BPCzPA is proved to be thermally stable.

Figure 16:
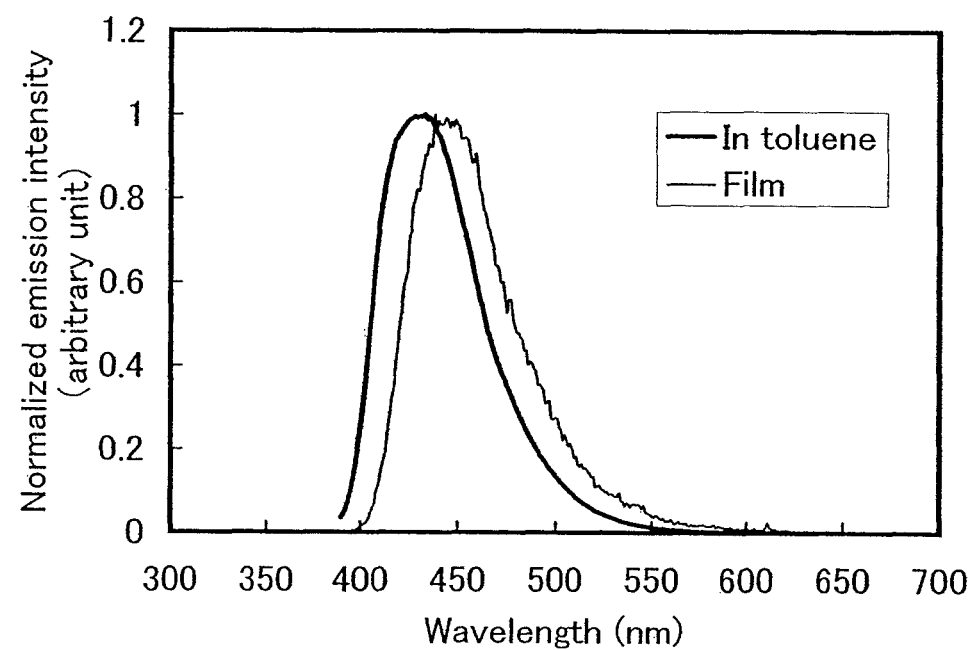
FIG. 16 shows light emitting spectrum of BPCzPA in toluene.

An absorption spectrum of toluene solution of BPCzPA is measured. The absorption of the toluene solution of BPCzPA based on anthracene is observed at about 370 nm. In addition, FIG. 16 shows emission spectrum of toluene solution of. In FIG. 16, the horizontal axis indicates a wavelength (nm) and the vertical axis indicates emission intensity (arbitrary unit). It can be found that the maximum emission wavelength is 437 nm (excitation wavelength 370 nm), and thus, blue light emission can be obtained.

HOMO level and LUMO level in the thin film state of BPCzPA are measured. The value of HOMO level is obtained by converting a value of the ionization potential measured with a photoelectron spectroscopy device (AC-2 manufactured by Riken Keiki Co., Ltd) to a negative value. The value of LUMO level is obtained by adding an energy gap between absorption edges of the thin film to a value of HOMO level. As a result, HOMO level and LUMO level are −5.68 eV and −2.75 eV, respectively and thus the extremely large band gap of 2.93 eV is obtained.

EXAMPLE 4

As an example of a material according to the invention, a synthetic method of a compound represented by formula (73) 9-{4-[3-(N,N-diphenylamino)-N-carbazolyl]phenyl}-10-phenylanthracene (hereinafter referred to as CzAlPA) below will be described. Note that, 9-phenyl-10-(4-bromophenyl) anthracene is prepared in the manner shown in Example 1.

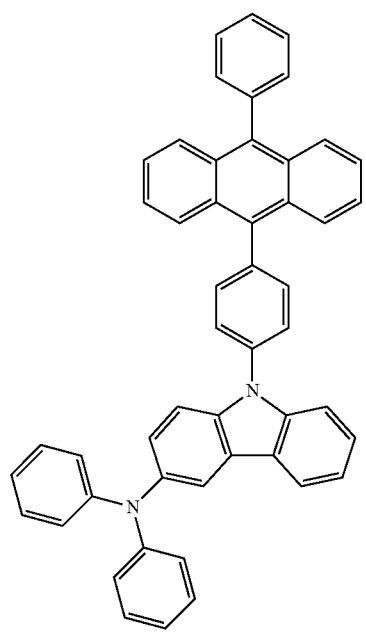
(73)

First, a synthetic method of 3-iodocarbazole will be shown below. 4.5 g (20 mmol) of N-iodo succinimide (NIS) is added into a glacial acetic acid (450 mL) solution containing 3.5 g (21 mmol) of carbazole little by little. After agitating it at room temperature overnight, reaction mixture is dropped into about 750 mL of water. The precipitate is collected. After the precipitate is rinsed with water, it is dissolved in about 150 mL of ethyl acetate. The solution is rinsed with sodium hydrogen carbonate solution, water, and saturated salt solution, and dried by adding magnesium sulfate. The solution is filtered and condensed to obtain 6.0 g of 3-iodocarbazole as white powder at a yield of 97%. The synthetic scheme of 3-iodocarbazole is shown below.

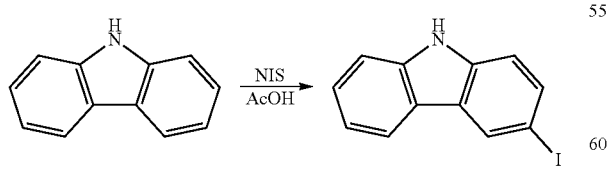

Next, a synthetic method of 9-acetyl-3-iodocarbazole will be shown below. Under a nitrogen atmosphere, a suspension of THF solution (50 mL) containing 4.7 g (16 mmol) of 3-iodocarbazole prepared by the above manner is slowly dropped into iced sodium hydride 1.0 g (60% in oil, 25 mmol) dehydrated THF (35 mL), and thereafter agitated for 30 minutes. 2.0 g (25 mmol) of acetyl chloride is dropped into the mixture. After the mixture is agitated for 1 hour, and further agitated overnight at room temperature. Approximately 30 mL of water is added to the mixture. The organic layer is rinsed with water and saturated salt solution, and about 50 mL of ethyl acetate is added to extract the organic material in the aqueous layer therein after that, the ethyl acetate is added to the organic layer. Magnesium sulfate is added to the organic layer to be dried. After the filtration and concentration, the obtained solid is rinsed with about 20 mL of hexane to obtain 5.1 g off-white powder of 9-acetyl-3-iodocarbazole at a yield of 94%. The synthetic scheme of 9-acetyl-3-iodocarbazole is shown below.

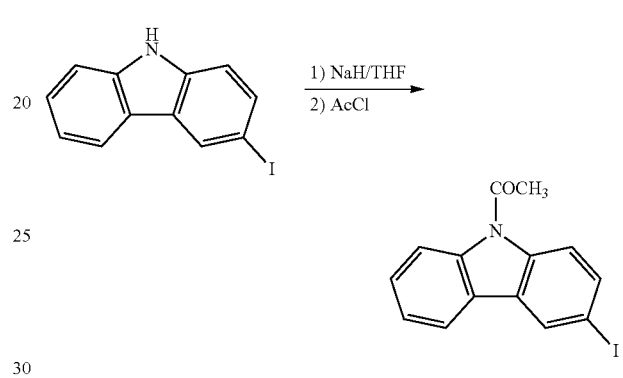

Next, a synthetic method of 9-acetyl-3-(N,N-diphenyl) aminocarbazole will be shown below. Under a nitrogen atmosphere, a suspension of 3.4 g, (10 mmol) of 9-acetyl-3-iodocarbazole, 2.0 g (12 mmol) of diphenylamine, 2.1 g (15 mmol) of copper (I) oxide, and 70 mL of N,N-dimethylacetamide is heated and agitated at 160° C. for 20 hours. After cooling to room temperature, about 50 mL of methanol is added and filtered through celite. The obtained filtrate is condensed. The residue is purified by silica gel column chromatography (developing solution, toluene:hexane=1:1) to obtain 1.8 g cream colored powder of 9-acetyl-3-(N,N-diphenyl)aminocarbazole at a yield of 48%. The synthetic scheme of 9-acetyl-3-(N,N-diphenyl)aminocarbazole is shown below.

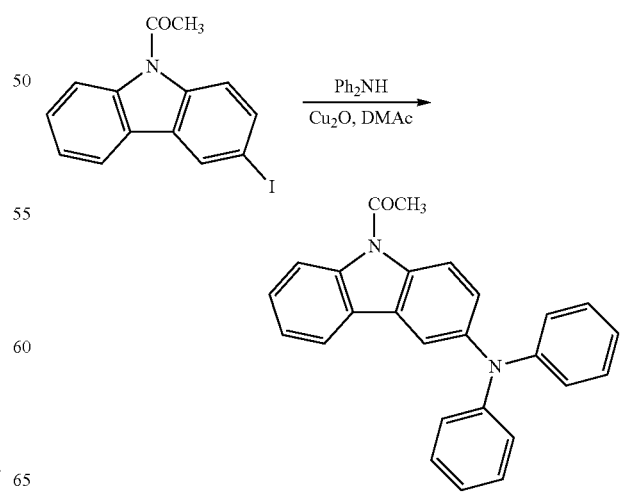

Figure 17:
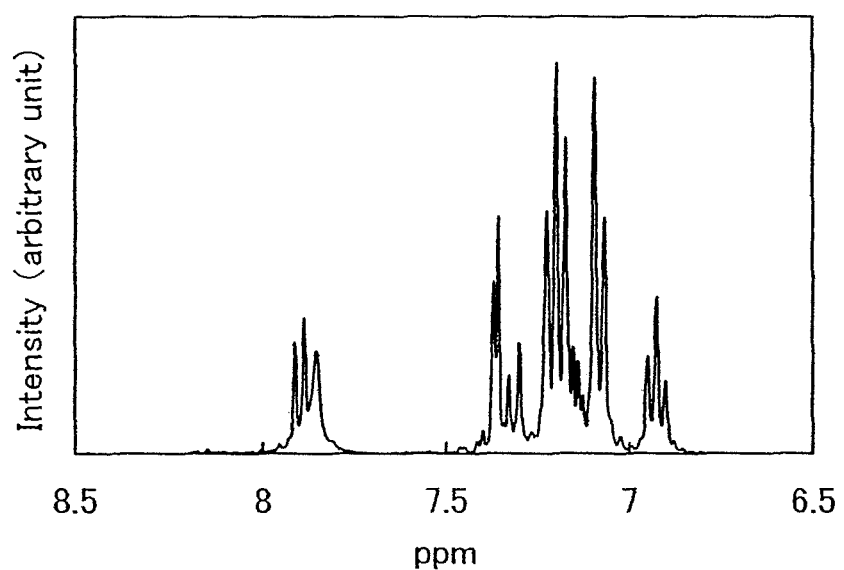
FIG. 17 shows $^1$H NMR spectrum of 3-(N,N-diphenyl)aminocarbazole.

A synthetic method of 3-(N,N-diphenyl)aminocarbazole will be shown below. A solution (3 mL) containing 2.8 g of potassium hydroxide and 50 mL of dimethylsulfide are added to THF (50 mL) solution containing 1.8 g (5 mmol) of 9-acetyl-3-(N,N-diphenyl)aminocarbazole, and heated and agitated at 100° C. 5 hours. About 100 mL of water is added, and extracted with about 150 mL of ethyl acetate. The organic layer is dried with magnesium sulfate. Filtration and condensation are carried out. The residue is purified by silica gel column chromatography (developing solution, toluene:hexane=1:1) to obtain 400 mg beige color powder of 3-(N,N-diphenyl)aminocarbazole at a yield of 27%. The synthetic scheme of 3-(N, N-diphenyl)aminocarbazole is shown below NMR data of the obtained 3-(N,N-diphenyl)aminocarbazole will be shown below. $^1$H NMR (300 MHz, CDCl3) δ=6.93 (t, J=7.5 Hz, 2H), 7.08 (d, J=7.8 Hz, 4H), 7.13-7.22 (m, 7H), 7.03-7.37 (m, 3H), 7.85 (s, 1H), 7.90 (d, J=7.8 Hz, 1H). Further, the NMR chart of 3-(N,N-diphenyl)aminocarbazole is shown in FIG. 17.

Next, a synthetic method of CzAlPA by coupling reaction of 3-(N,N-diphenyl)aminocarbazole and 9-phenyl-10-(4-bromophenyl) anthracene will be shown below. Xylene suspension (3.5 mL) containing 340 mg (1.0 mmol) of 3-(N,N-diphenyl)aminocarbazole, 490 mg (1.2 mmol) of 9-phenyl-10-(4-bromophenyl) anthracene, 58 mg (0.1 mmol) of dibenzylidine (II) palladium, and t-butoxy sodium (300 mg, 3.0 mmol) is degassed for 3 minutes. After that, tri(t-butylphosphine)(10% hexane solution 1.0 mL, 0.5 mL) is added, and it was heated and agitated at 90° C. for 4.5 hours. About 300 mL of toluene is added, and filtration through Florisil, alumina, and celite is conducted. The obtained filtrate is rinsed with water and saturated salt solution, and is dried by adding magnesium sulfate. That was filtered and condensed, and the residue is purified by silica gel column chromatography (developing solution, toluene:hexane=3:7). As a result, 300 mg of CzAlPA is obtained as cream colored powder at a yield of 45%. The synthetic scheme of CzAlPA by coupling reaction of 3-(N,N-diphenyl)aminocarbazole and 9-phenyl-10-(4-bromophenyl) anthracene is shown below.

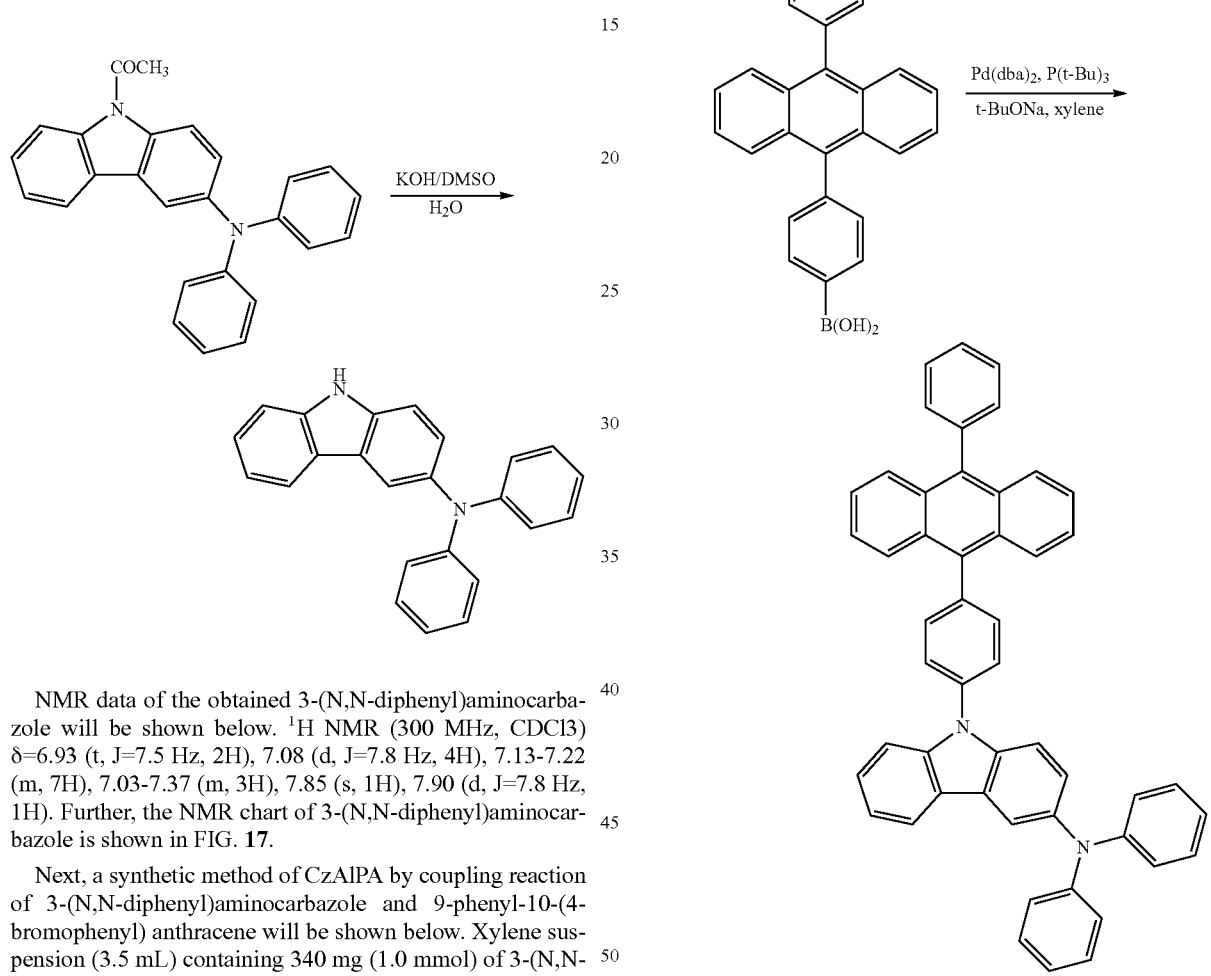

Figure 18:
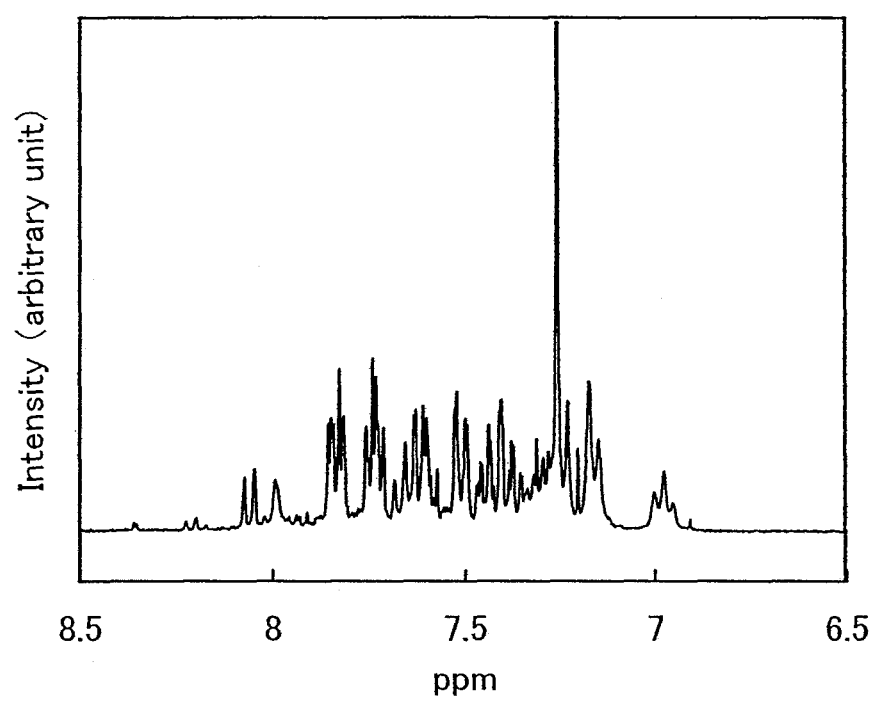
FIG. 18 shows $^1$H NMR spectrum of CzAlPA.

NMR data of the obtained CzAlPA will be shown below. $^1$H NMR (300 MHz, CDCl$_3$) δ=6.98 (t, J=7.2 Hz, 2H), 7.16 (d, J=7.8 Hz, 4H), 7.20-7.86 (m, 26H), 7.99 (s, 1H), 8.06 (d, J=7.8 Hz, 1H). Further, the NMR chart of CzAlPA is shown in FIG. 18.

Thermogravimetry-differential thermal analysis (TG-DTA) of CzAlPA was conducted. A thermogravimetry-differential thermal analysis apparatus (TG/DTA SCC 5200 manufactured by Seiko Instruments Inc.) is used to measure the CaAlPA. Thermophysical properties are evaluated under a nitrogen atmosphere with a rising temperature of 10° C./min. Consequently, based on gravity-temperature relationship (thermogravimetric measurement), the temperature under normal pressure where reduction of the gravity starts is 420° C. Further, the glass transition temperature and the melting point of the obtained compound CzAlPA is examined with a differential scanning calorimeter (Pyris 1 DSC manufactured by Perkin Elmer Co., Ltd.). The results are 153° C. and 313° C. respectively; thus, CzAlPA is proved to be thermally stable.

Figure 19:
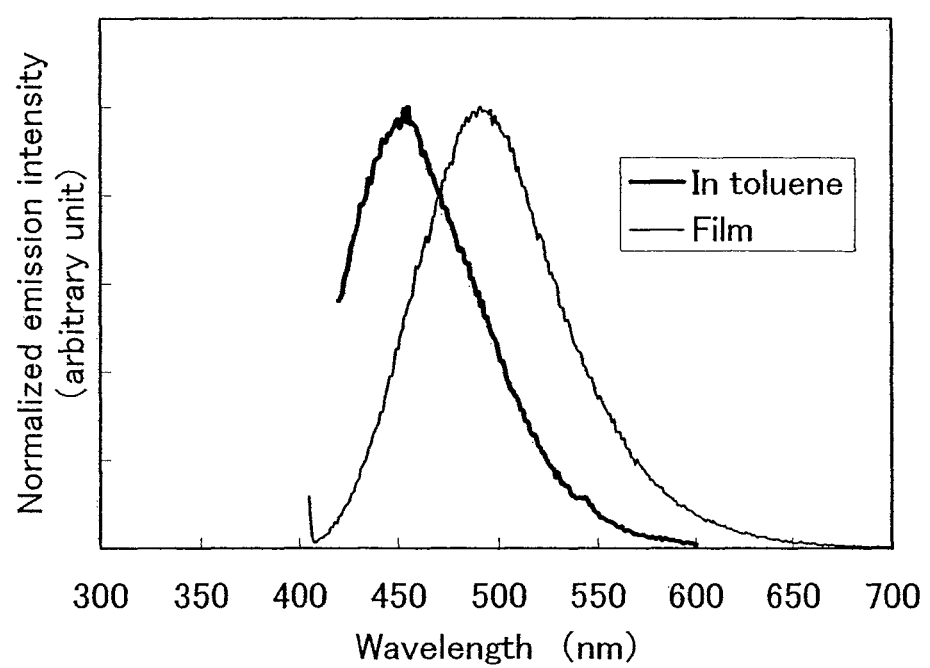
FIG. 19 shows light emitting spectrum in a thin film of CzAlPA and toluene.

An absorption spectrum of toluene solution of CzAlPA and a thin film state of CzAlPA are measured. The absorption of the toluene solution of CzAlPA and thin film state of CzAlPA based on anthracene are observed at about 370 nm and 400 nm, respectively. In addition, FIG. 19 shows emission spectrum of toluene solution of CzAlPA and the thin film state of CzAlPA. In FIG. 19, the horizontal axis indicates a wavelength (nm) and the vertical axis indicates emission intensity (arbitrary unit). It can be found that the maximum emission wavelength of toluene solution and the thin film state of CzAlPA are 453 nm (excitation wavelength 370 nm) and 491 nm (excitation wavelength 380 nm), respectively, and thus, blue light emission can be obtained.

HOMO level and LUMO level in the thin film state of CzAlPA are measured. The value of HOMO level is obtained by converting a value of the ionization potential measured with a photoelectron spectroscopy device (AC-2 manufactured by Riken Keiki Co., Ltd) to a negative value. The value of LUMO level is obtained by adding an energy gap between absorption edges of the thin film to a value of HOMO level. As a result, HOMO level and LUMO level are −5.30 eV and −2.38 eV, respectively and thus the extremely large band gap of 2.82 eV is obtained.

COMPARATIVE EXAMPLE 1

As compared with a material of the present invention, a synthetic method of 2-t-butyl-9,10-bis(4-(N-carbazolyl)phenyl)anthracene (hereinafter referred to as CzBPA) which is a compound represented by formula (121).

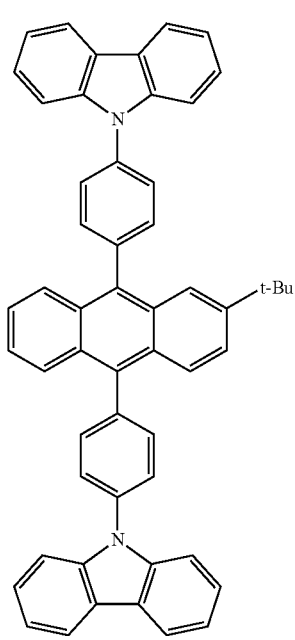

(121)

Under a stream of nitrogen, 0.3 mL of tri(t-butyl) phosphine (10% hexane solution) is added to toluene solution (30 mL) containing 3.00 g (5.53 mmol) of 9,10-bis (4-bromophenyl)-2-t-butylanthracene, 1.93 g (11.2 mmol) of carbazole, 318 mg (0.55 mmol) of dibenzylidineacetone palladium, and 3.00 g (31.2 mmol) of t-butoxy sodium, and it is refluxed at 110° C. for 3 hours. After the reaction solution is rinsed with water, the aqueous layer is extracted with toluene, and rinsed together with the organic layer with saturated salt solution. The organic layer is dried with magnesium sulfate, and an oily product which is naturally filtered and condensed is purified by alumina column chromatography (eluent: chloroform). In addition, the obtained solid is recrystallized with dichloromethane/hexane to obtain 1.80 g light yellow solid of CzBPA (at a yield of 45%). The synthetic scheme of CzBPA is shown below.

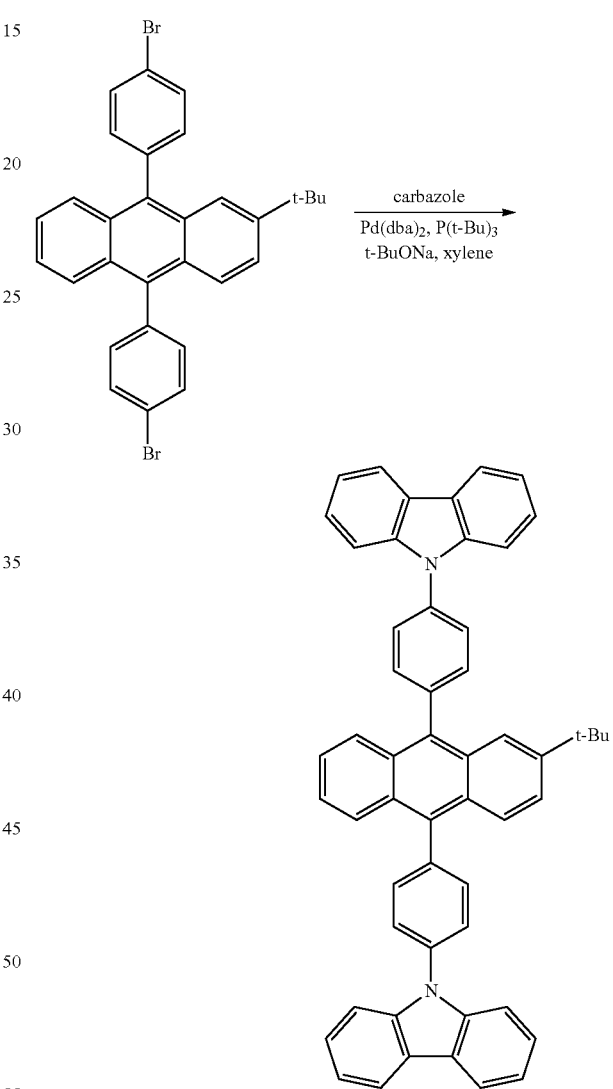

Figure 20:
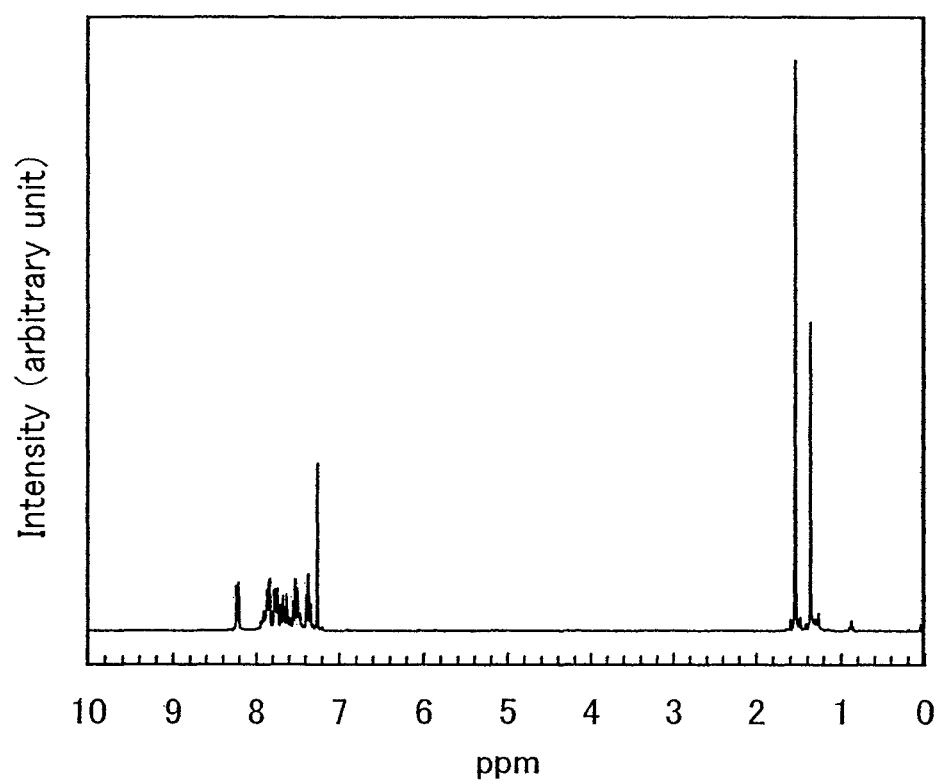
FIG. 20 shows $^1$H NMR spectrum of CzBPA.

NMR data of the obtained CzBPA will be shown below. $^1$H NMR (300 MHz, CDCl$_3$) δ=8.23 (d, J=7.2 Hz, 4H), 7.94-7.63 (m, 16H), 7.59 (d, J=1.8 Hz, 1H), 7.55-7.47 (m, 6H), 7.39-7.34 (m, 4H), 1.36 (s, 9H). Further, the NMR chart of CzBPA is shown in FIG. 20.

Thermogravimetry-differential thermal analysis (TG-DTA) of CzBPA was conducted. A thermogravimetry-differential thermal analysis apparatus (TG/DTA SCC 5200 manufactured by Seiko Instruments Inc.) is used to measure the CzBPA. Thermophysical properties are evaluated under a nitrogen atmosphere with a rising temperature of 10° C./min.

Consequently, based on gravity-temperature relationship (thermogravimetric measurement), the temperature under normal pressure where reduction of the gravity starts is 460° C.

REFERENCE EXAMPLE

In this reference example, a condensed aromatic group and a phenyl group which are to be introduced into 9 or 10 position of an anthracene skeleton represented by structural formula (1) as bulky substituent are compared. As the anthracene derivative in which a phenyl group is introduced into 9 or 10 position, 9,10-diphenylanthracene (hereinafter referred to as DPAnth) is used, and as a comparable compound, in which a condensed aromatic group is introduced into 9 or 10 position, 2-t-butyl-9,10-di(2-naphthyl) anthracene (hereinafter referred to as t-BuDNA) is used.

First, electrochemical stability of DPAnth and t-BuDNA is evaluated by cyclic voltammetry (CV) measurement. Further, an electrochemical analyzer (#ALS model 600A, BAS Inc.) is used for the measurement device. As to a solution used in the CV measurement, dehydrated dimethylformamide (DMF) is used as a solvent. Tetraperchlorate-n-butylammonium (n-$Bu_4NClO_4$), which is a supporting electrolyte, is dissolved in the solvent such that the concentration of the tetraperchlorate-n-butylammonium is 100 mM. Also, the DPAnth, which is an object to be measured, is dissolved such that the concentration thereof is set to be 1 mM. Further, a platinum electrode (a PTE platinum electrode, BAS Inc.) is used as a work electrode. A platinum electrode (a VC-3 Pt counter electrode (5 cm), BAS Inc.) is used as an auxiliary electrode. An Ag/$Ag^+$ electrode (an RE 5 reference electrode for non-aqueous solvents, BAS Inc.) is used as a reference electrode. The scanning speed is set at 0.1 V/sec, and 200 times of scanning are conducted on each of a oxidation side and a reduction side.

Figure 21A:
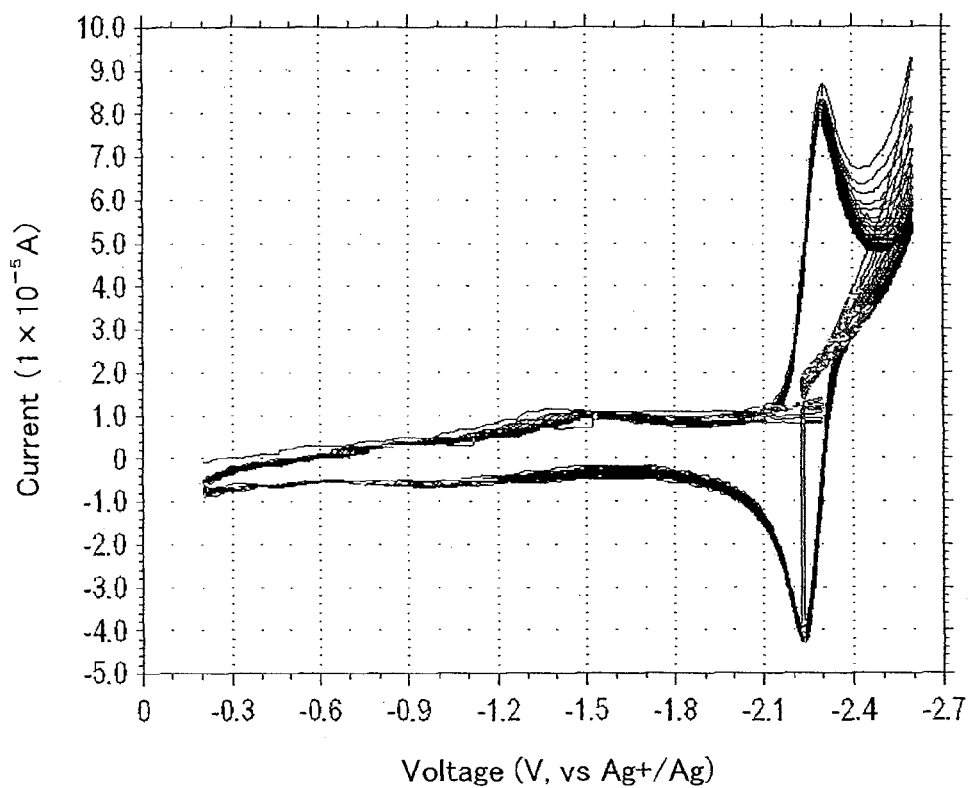
FIGS. 21A and 21B show CV charts of DPAnth.
Figure 21B:
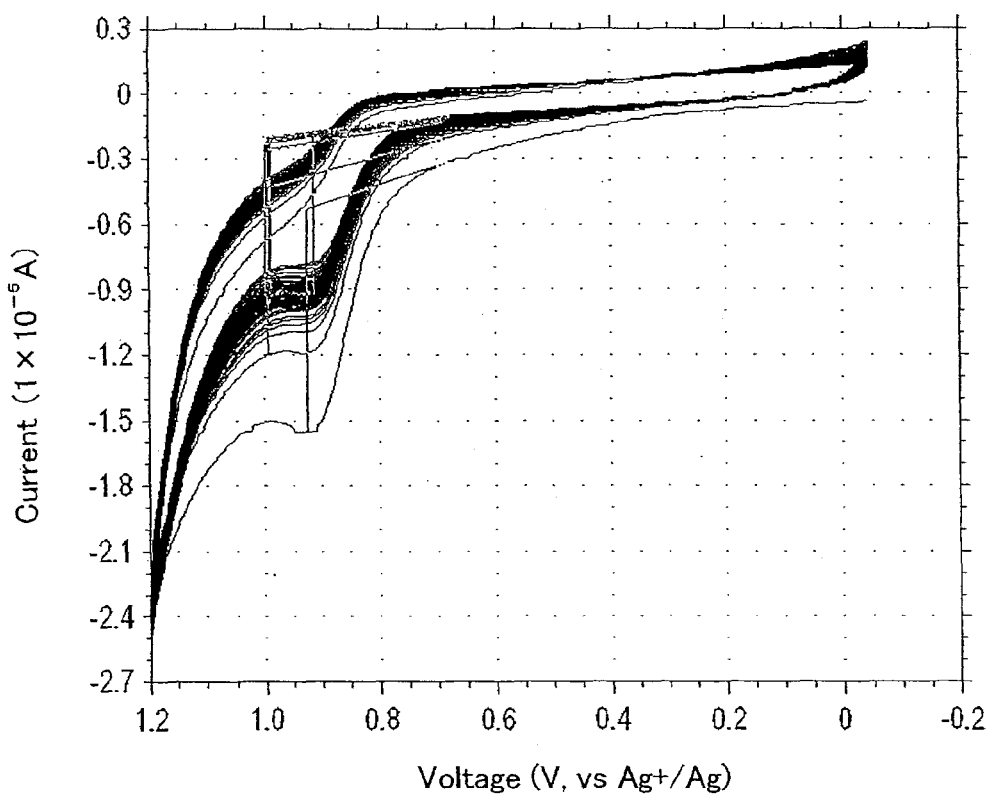
Figure 22A:
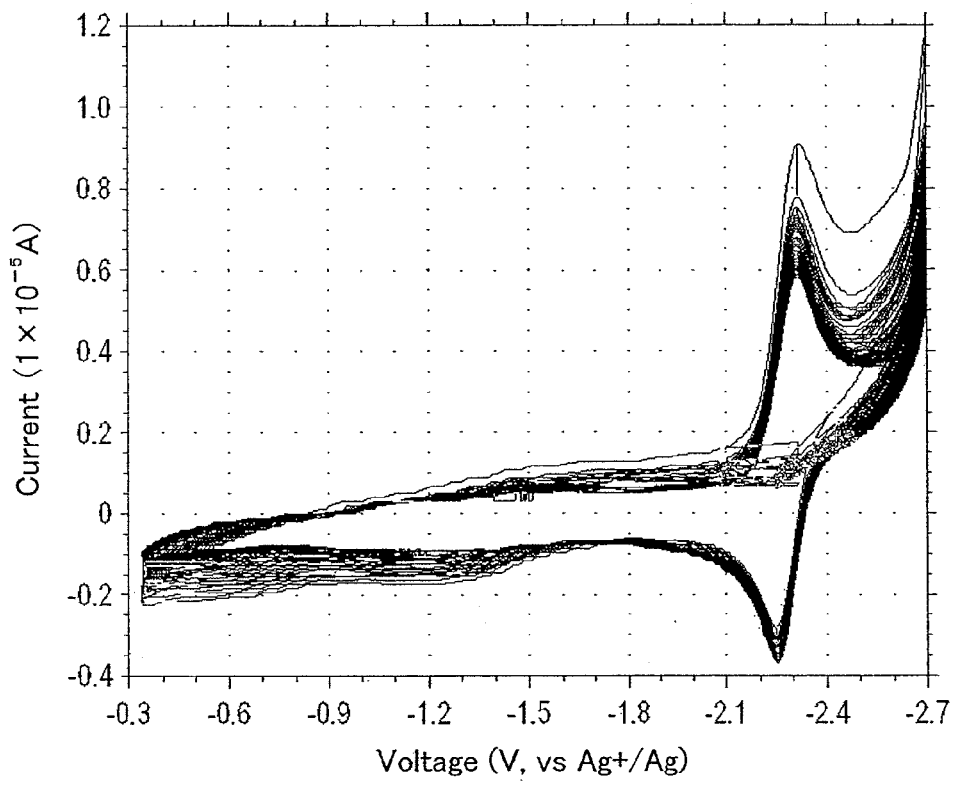
FIGS. 22A and 22B show CV charts of t-BuDNA.
Figure 22B:
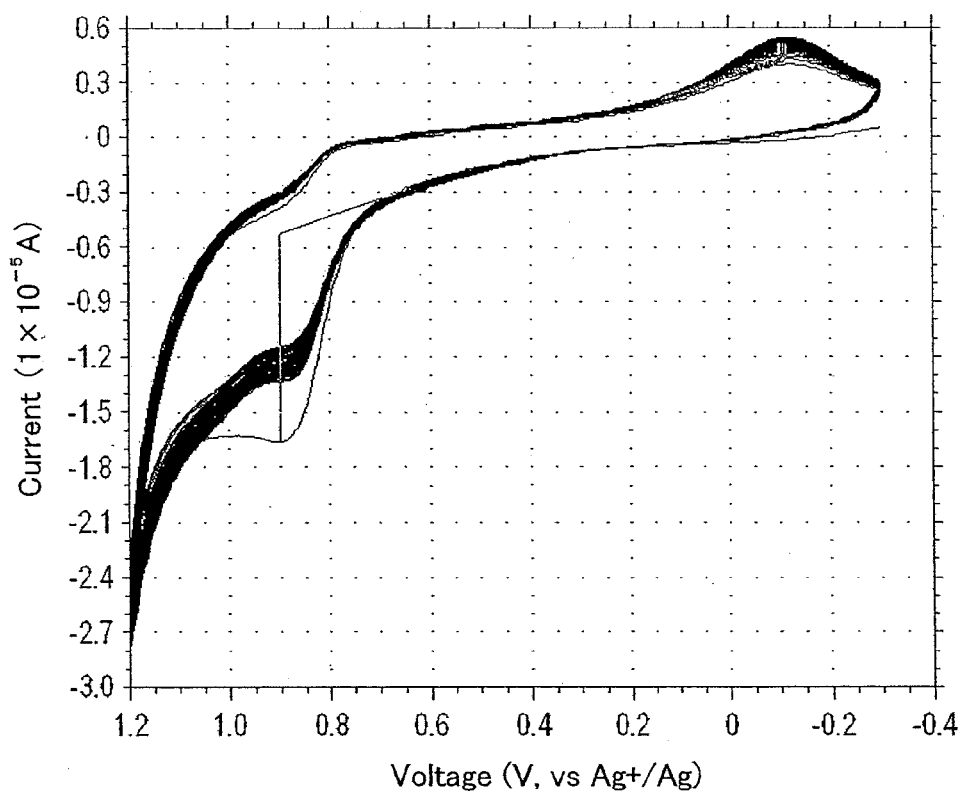

FIG. 21 and FIG. 22 respectively show CV measurement results of DPAnth and t-BuDNA. In the figures, (A) indicates the measurement result of the reduction side, and (B) indicates measurement result of the oxidation side. It is found that either of the reduction side or the oxidation side of the compounds provides reversible peak. Further, it is found that even when oxidation to reduction or reduction to oxidation is repeated 200 times, the height of oxidation peak or reduction peak, specifically the current value of reduction hardly changes. This means that DPAnth and t-BuDNA are stable to oxidation and reduction. Accordingly, it can be said that even when either one of the phenyl group or the naphthyl group is introduced into 9 or 10 position, the electrochemical stability hardly changes.

Next, stability of the excited state is evaluated. The evaluation manner will be described below. First, DPAnth and t-BuDNA are deposited on a quartz substrate (1.0 cm×5 cm) using a vacuum evaporation apparatus. The film thickness is 250 nm. The film is irradiated with light of a high pressure mercury lamp through a glass filter under a nitrogen atmosphere. Since the irradiation is carried out through the glass filter, it corresponds to the irradiation with light of about 350 nm or more. This means that the anthracene parts of DPAnth and t-BuDNA are specifically excited. Therefore, in this experiment, DPAnth and t-BuDNA is to repeat excitation-deactivation. By conducting the light irradiation and monitoring luminous intensity of absorption (300 to 400 nm) based on anthracene, photochemical stability of the anthracene skeleton can be measured.

Specifically if the anthracene skeleton is excited by light irradiation and thereafter returns to a ground state, the absorption intensity based on the anthracene skeleton does not change. However, when the excited state reacts in some manner, the anthracene does not return to the original molecules and the absorption is to be reduced.

Figure 23:
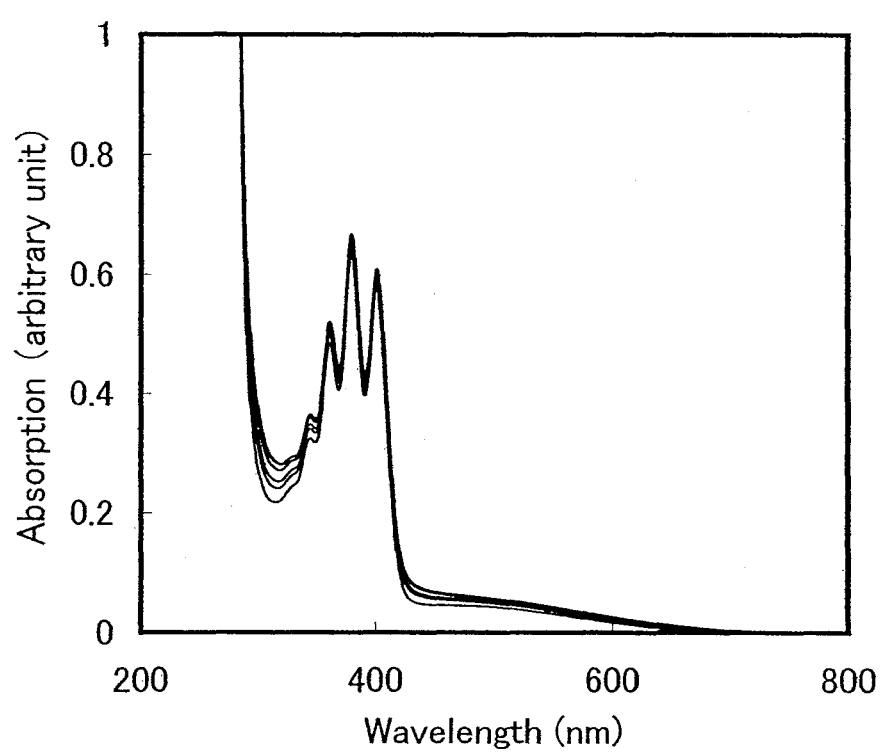
FIG. 23 shows change of absorption spectrum of a thin film of DPAnth under light irradiation over time.
Figure 24:
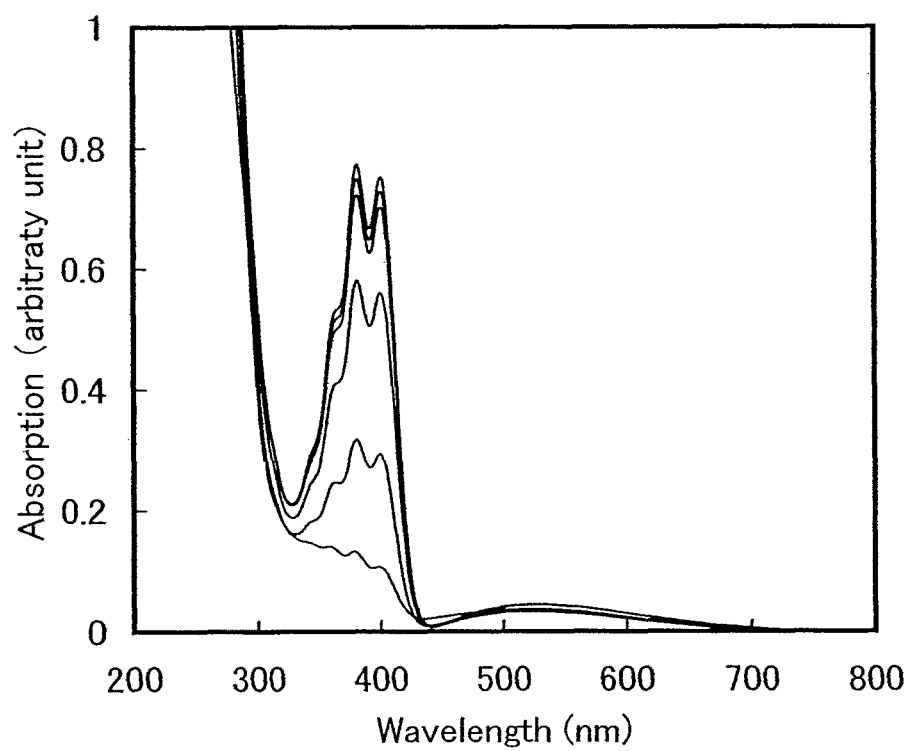
FIG. 24 shows change of absorption spectrum of a thin film under light irradiation over time.
Figure 25:
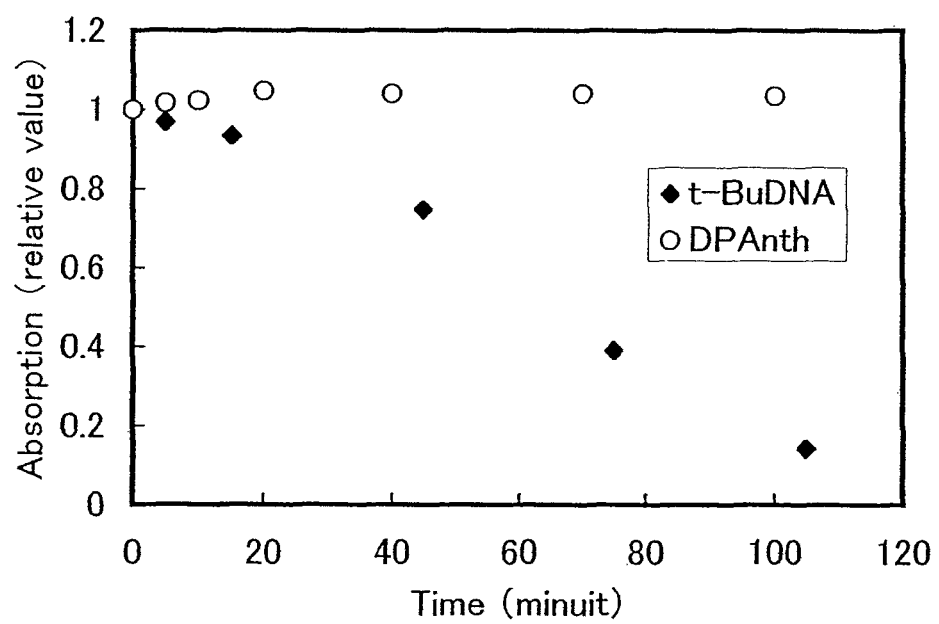
FIG. 25 shows change of absorption intensity of a 400 nm thin film of t-BuDNA and DPAnth under light irradiation over time.

FIG. 23 and FIG. 24 show change of absorption over time in irradiating DPAnth and t-BuDNA respectively with light. FIG. 23 shows the measurement result of the absorption in irradiating DPAnth with light for 0 minute, 5 minutes, 10 minutes, 20 minutes, 40 minutes, 70 minutes, and 100 minutes respectively. According to this, it is found that the absorption DPAnth based on anthracene hardly changed by light irradiation. FIG. 24 shows the measurement result of the absorption in irradiating t-BuNA with light for 0 minute, 5 minutes, 15 minutes, 45 minutes, 75 minutes, and 105 minutes. In the case of t-BuDNA, it is found that the anthracene absorption rapidly reduces. Change of absorption intensity with respect to 400 nm is plotted in FIG. 25. As shown in FIG. 24, it is found that the absorption intensity of DPAnth hardly changes through light irradiation for about 120 minutes while the absorption intensity of t-BuDNA significantly reduces. Therefore, in the case where a naphthyl group is introduced into 9 or 10 position as a substituent, the photochemical stability is found to reduce significantly. In contrast, photochemical stability is high in the case of a phenyl group.

EXAMPLE 5

This example will describe electrochemical stability of an anthracene derivative of the present invention in which an anthracene skeleton and a carbazolyl skeleton are introduced in a molecule, and an anthracene derivative in which two carbazolyl groups for one anthracene skeleton are introduced into a molecule which are represented by general formulae (2) and (3).

Figure 26A:
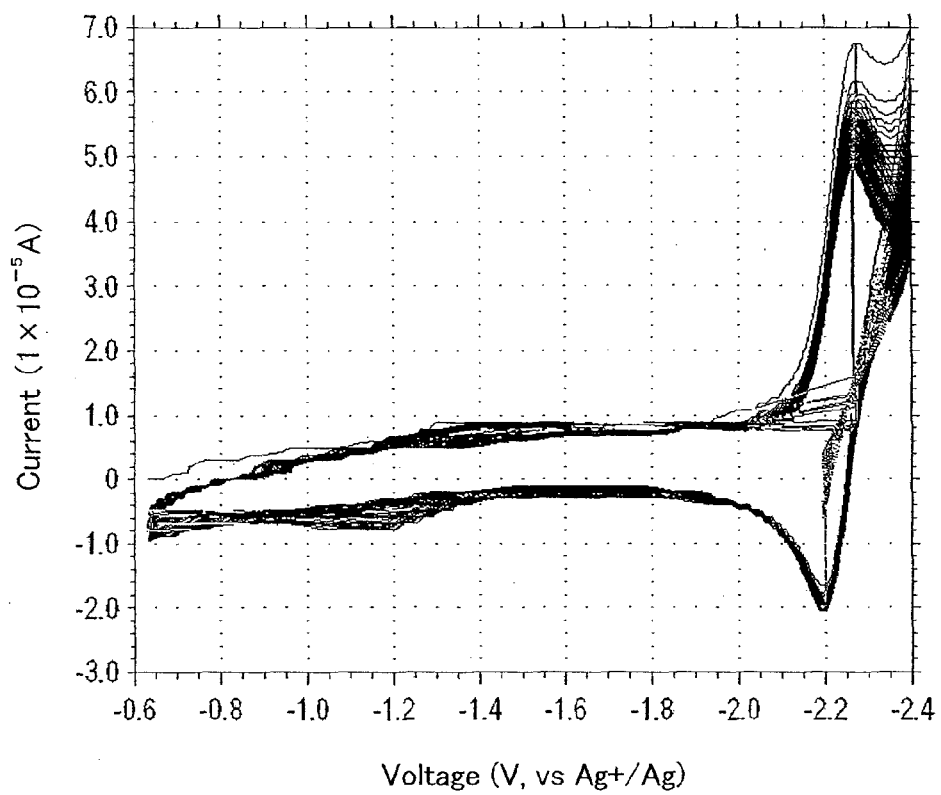
FIGS. 26A and 26B show CV charts of reduction side (A) and oxidation side (B) of CzPA.
Figure 26B:
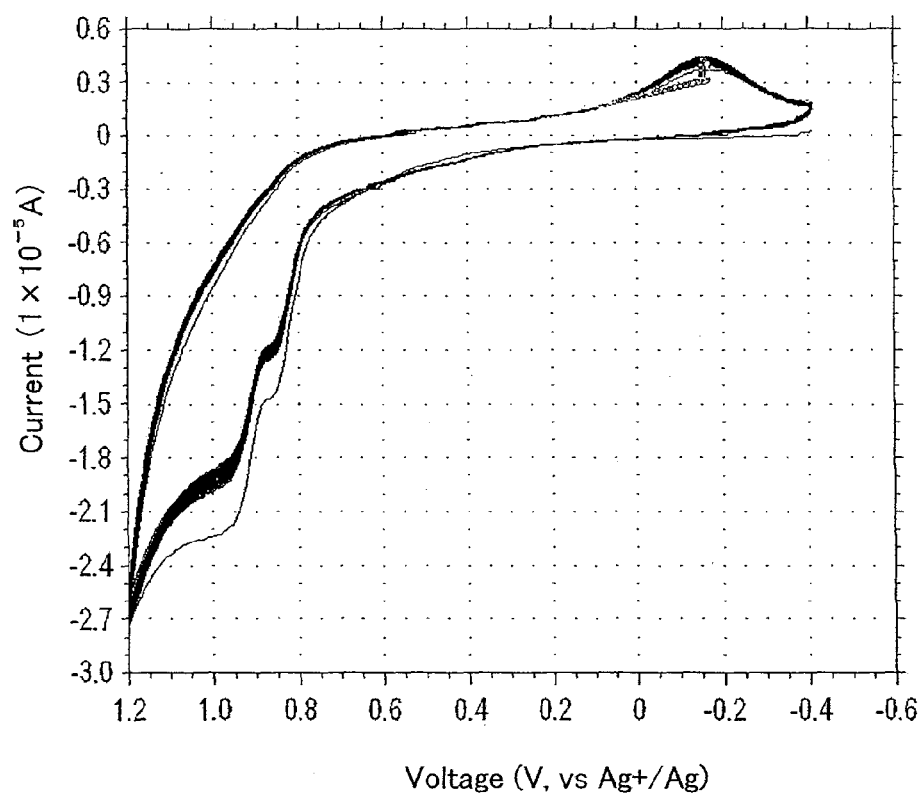
Figure 27A:
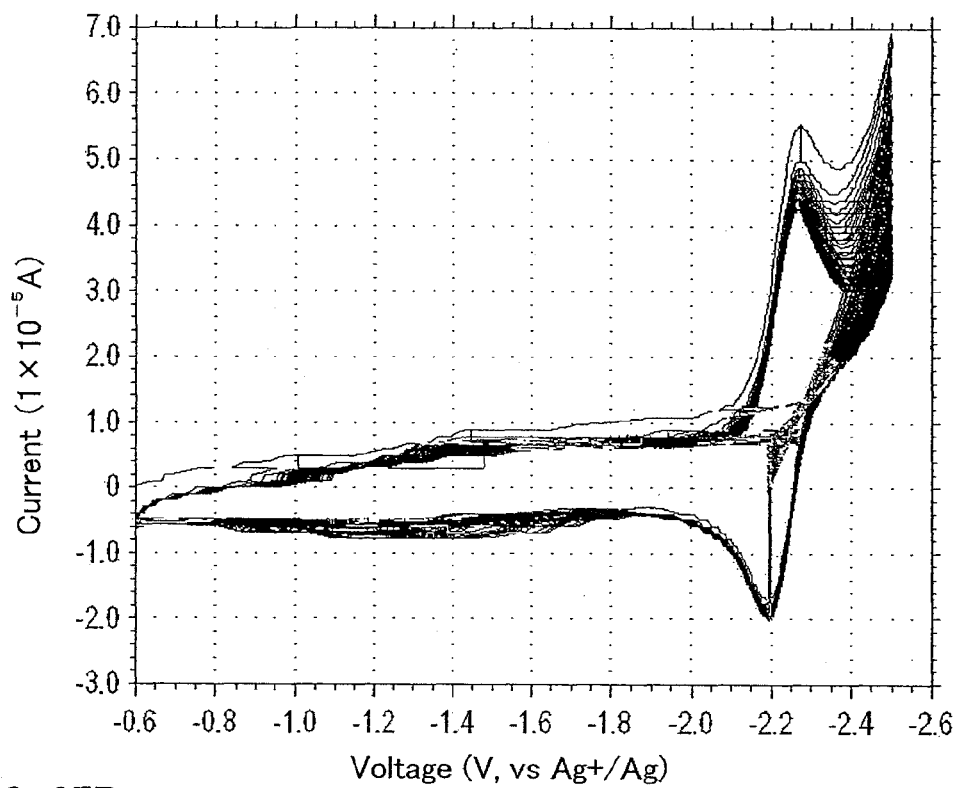
FIGS. 27A and 27B show CV charts of reduction side (A) and oxidation side (B) of DPCzPA.
Figure 27B:
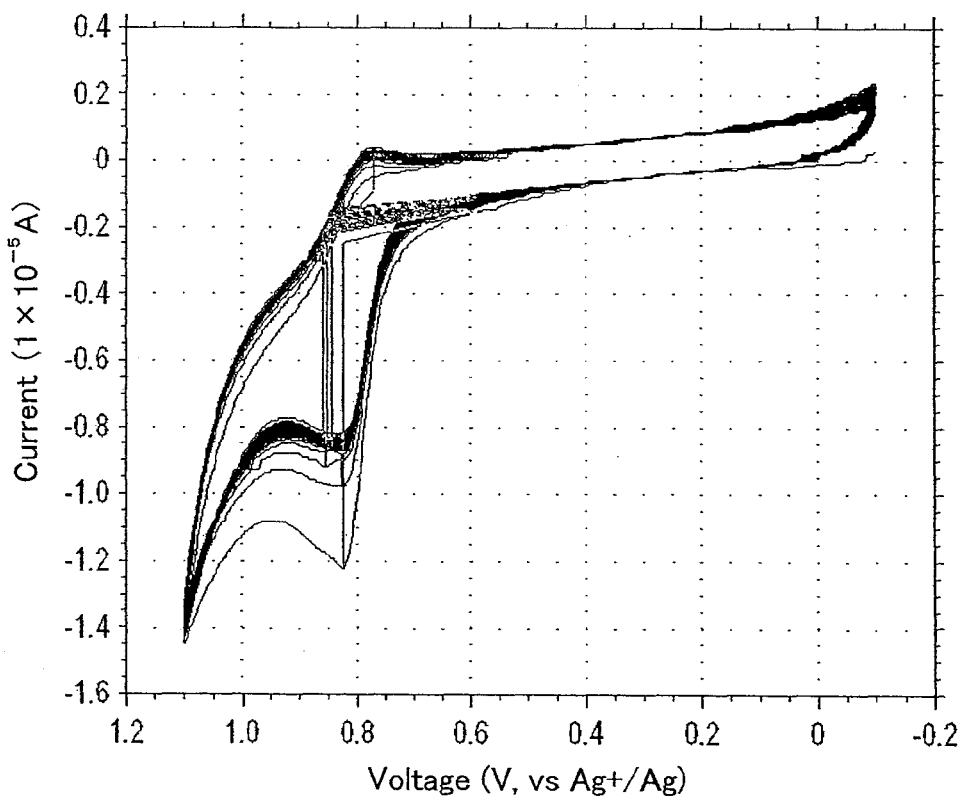
Figure 28A:
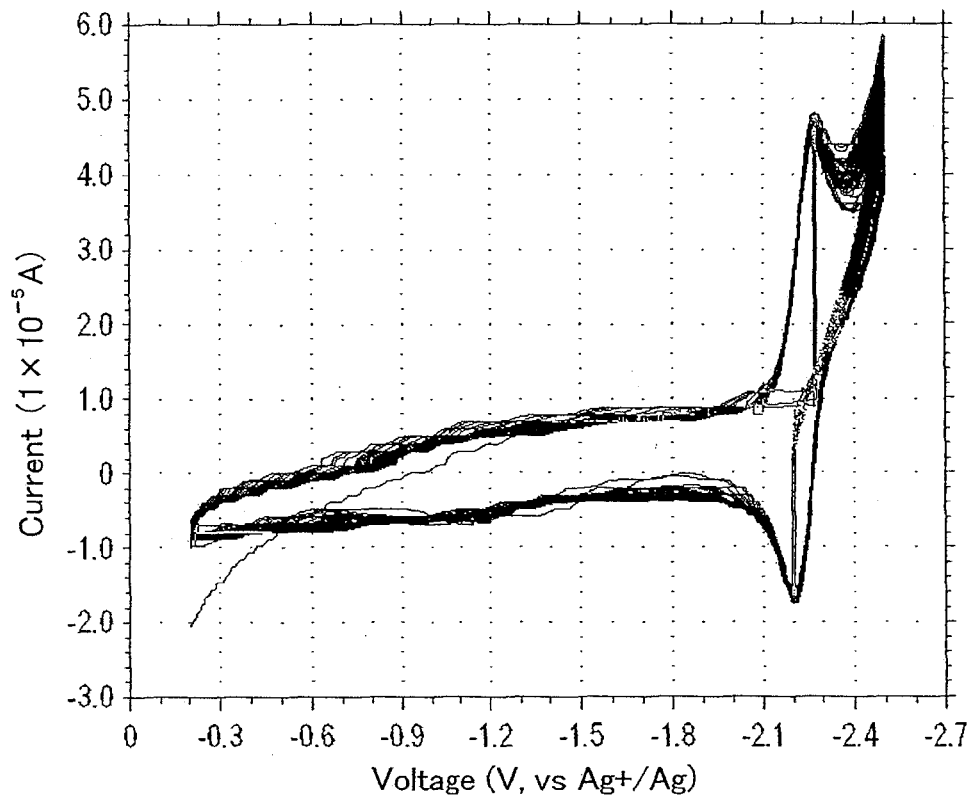
FIGS. 28A and 28B show CV charts of reduction side (A) and oxidation side (B) of CzAlPA.
Figure 28B:
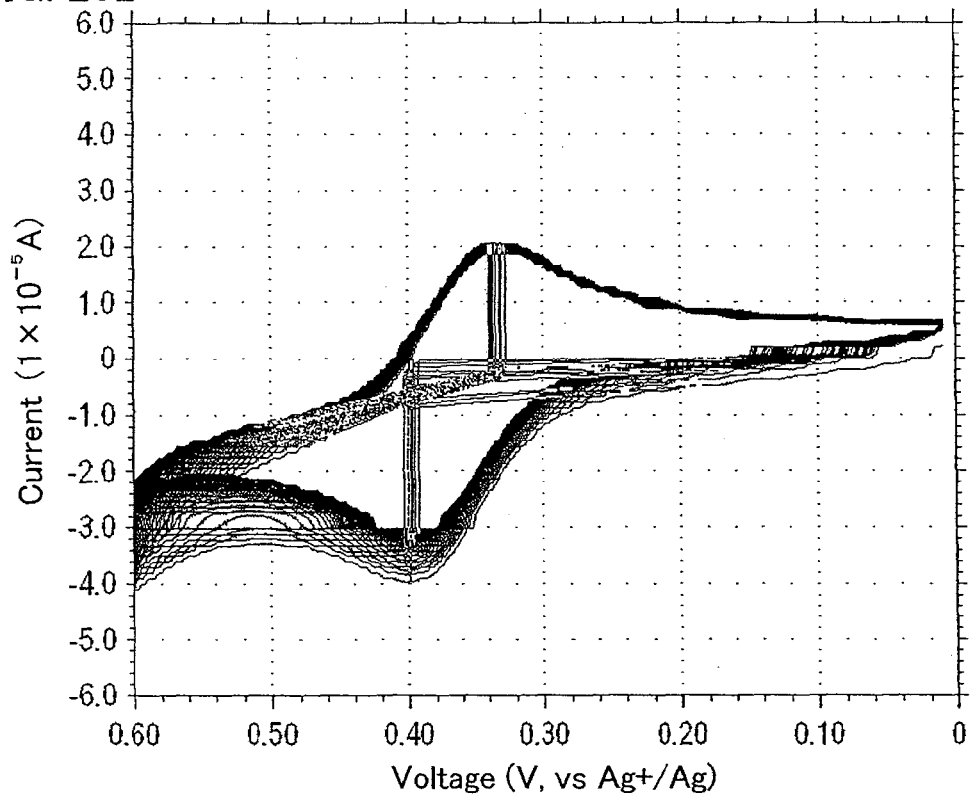
Figure 29A:
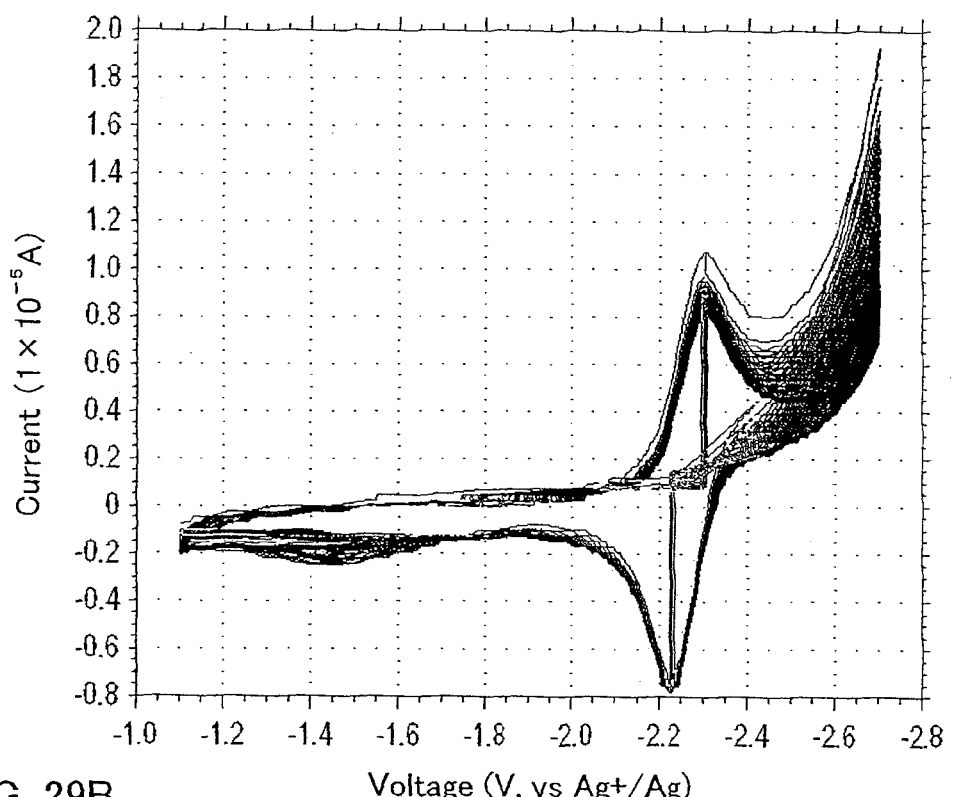
FIGS. 29A and 29B show CV charts of reduction side (A) and oxidation side (B) of CzBPA.
Figure 29B:
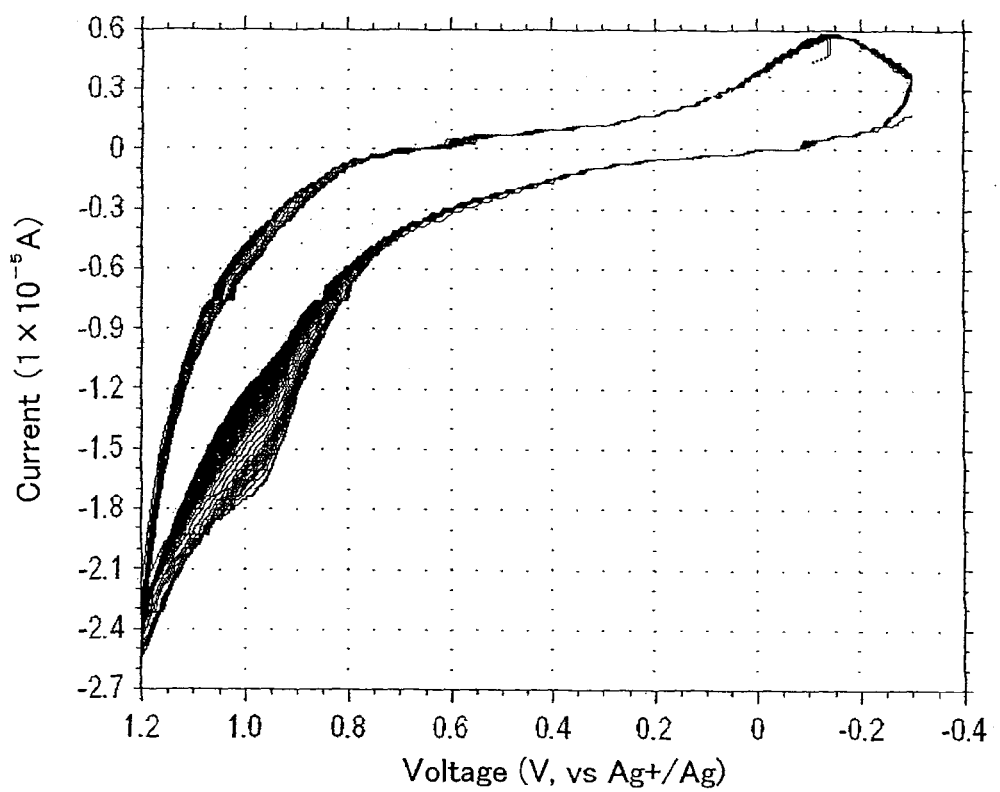

The electrochemical stability was evaluated by carrying out a CV measurement as in the reference example. The measurement conditions are the same as ones shown in the reference example. CzPA, DPCzPA, and CzAlPA into which an anthracene skeleton and a carbazolyl skeleton are introduced; and CzBPA into which an anthracene skeleton and two carbazolyl skeletons are introduced are used as the samples for CV measurement. FIG. 26 shows a CV chart of CzPA, FIG. 27 shows a CV chart of DPCzPA, FIG. 28 shows a CV chart of CzAlPA, and FIG. 29 shows a CV chart of CzBPA. Note that in the figures, (A) indicates a measurement result of a reduction side, and (B) indicates a measurement result of an oxidation side.

In the case of CzPA, both the oxidation side and the reduction side each show a reversible peak, and the peak intensity hardly changes even though cycles reaching 200 times of oxidation-reduction or reduction-oxidation are repeated. Similarly, in the case of DPCzPA and CzAlPA, the oxidation side and the reduction side behaves reversibly, and the peak intensity hardly changes even though cycles reaching 200 times of oxidation-reduction or reduction-oxidation are repeated. Thus, the anthracene derivative having an anthracene skeleton and a carbazolyl skeleton is electrochemically stable.

On the other hand, in the case of CzBPA, the reduction side behaves reversibly, and almost the same peak is provided after the cycles reaching 200 times; thus, CzBPA is stable to the cycles of reduction-oxidation. However, in the oxidation side, although reversible behavior is observed, the oxidation peak intensity gradually reduces after the 200 cycles repeated. This means that CzBPA is specifically in an oxidized state; accordingly, the holes of CzBPA are chemically unstable.

From the foregoing, a compound in which a carbazolyl group and an anthryl group are introduced is electrochemically stable, and in contrast, a compound in which two carbazolyl groups for an anthryl group are introduced is electrochemically unstable. In an organic light emitting element, the organic compound repeats oxidation-reduction, or reduction-oxidation in light emission. Therefore, an anthracene derivative of the present invention in which an anthracene skeleton and a carbazolyl skeleton are introduced into a molecule as represented by general formulae (2) and (3) is suitable to achieve high reliability.

EXAMPLE 6

This example will describe that an anthracene derivative of the present invention in which an anthracene skeleton and a carbazolyl skeleton are introduced into a molecule, and a phenyl group is introduced into 9 and 10 positions of the anthracene are highly reliable, and the reliability of an element can be improved by using such an anthracene derivative.

First, as comparable objects, an element using CzBPA having two carbazolyl skeletons for an anthracene skeleton, and an element using t-BuDNA as a compound in which a condensed aromatic ring is introduced into 9 and 10 positions of an anthracene skeleton were manufactured.

The element was formed over a glass substrate, ITSO is formed to a film thickness of 1100 nm as a first electrode sequentially from the glass substrate side. The ITSO is deposited by sputtering. Note that in the present invention, the shape of the first electrode is 2 mm×2 mm. Next, the substrate surface is washed with a porous resin (generally, PVA (polyvinyl alcohol) or nylon), heat treatment is carried out at 200° C. for one hour, and UV ozone treatment is conducted for 370 seconds as pretreatment for forming a light emitting element over the first electrode.

Next, as a hole injection layer, 4,4'-bis[N-(4-(N,N-di-m-tolylamino) phenyl)-N-phenylamino] biphenyl (hereinafter referred to as DNTPD) is formed to 20 nm. Subsequently, NPB is formed to 40 nm as a hole transporting material. t-BuDNA or CzBPA is formed to a film thickness of 40 nm as a light emitting layer over the film stack. Further, Alq is formed to 20 nm as an electron transporting layer, and calcium fluoride ($CaF_2$) is formed to 1 nm as an electron injection layer. Finally, Al is formed to a film thickness of 200 nm as a second electrode to complete the element. Note that, each of the films of the hole injection layer to the second electrode are formed by vapor deposition by resistance heating. Here, an element using t-BuDNA for the light emitting layer is element A, and an element using CzBPA for the light emitting layer is element B.

Original properties of the element A and the element B are shown in Table 1.

TABLE 1

Original properties of element A and element B

| Element | Light emitting Starting voltage (V) | Voltage at 500 $Cd/m^2$ (V) | Chromaticity (x, y) | Efficiency at 500 $Cd/m^2$ (Cd/A) |
|---|---|---|---|---|
| A | 3.4 | 6.4 | (0.15, 0.09) | 1.63 |
| B | 4.2 | 7.2 | (0.15, 0.10) | 2.28 |

Figure 30:
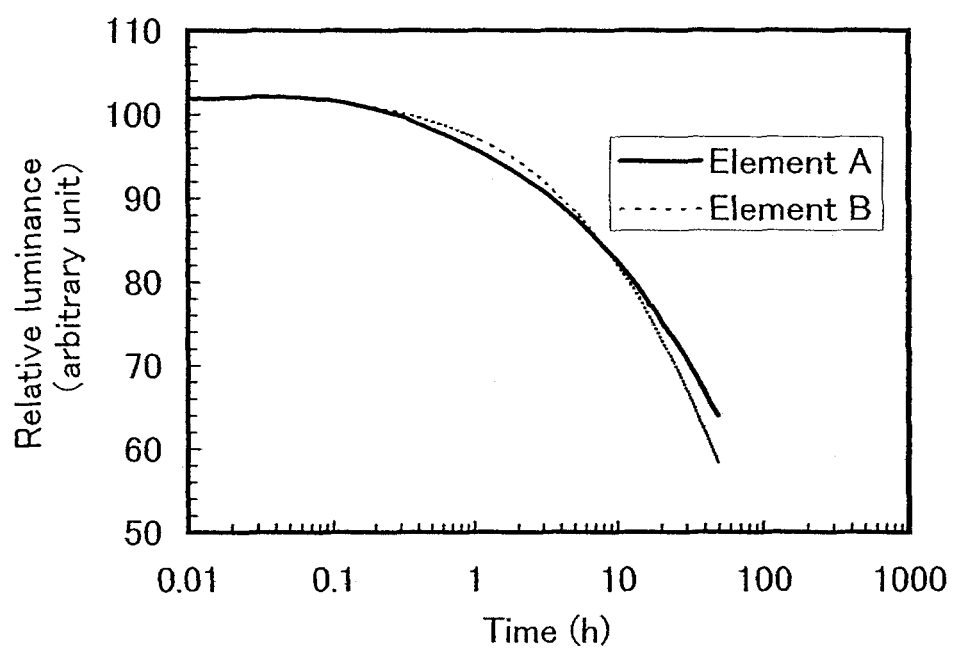
FIG. 30 shows a reliability measurement result of an element A and an element B.

Whichever of the elements A or B provides excellent chromaticity as a blue color light emitting element; however, the current efficiency was found to be low. The reliability test result of those elements are shown in FIG. 30. The test condition are set as follows: the initial luminance is set at 500 cd/A, the element is driven by constant current, and the change of the luminance over time is measured.

The half-life of whichever of the elements is less than 100 hours; thus, it is found that adequate reliability cannot be achieved with respect to a light emitting element using t-BuDNA in which a condensed aromatic ring is introduced into 9 and 10 positions of an anthracene skeleton, or CzBPA having two carbazolyl groups for an anthracene skeleton for a light emitting layer.

In contrast, when CzPA which is an anthracene derivative according to the invention which has an anthracene skeleton and a carbazolyl skeleton is used, the reliability is improved. The specific data is shown below.

As with the above described method, CuPc is formed to 20 nm as a hole injection layer over ITSO 4,4'-di[N,N'-(2-spirofluorenyl)-N,N'-diphenyl]amino-1,1-biphenyl (hereinafter referred to as BSPB) was formed to 40 nm as a hole transporting layer, CzPA is formed to 40 nm as a light emitting layer, Alq is formed to 20 nm as an electron transporting layer, calcium fluoride ($CaF_2$) is formed to 1 nm as an electron injection layer, and Al is formed to 200 nm as a second electrode. This element is an element C. For the comparison, an element in which t-BuDNA is formed to 40 nm instead of CzPA as a light emitting (hereinafter referred to as an element D), and an element in which 9,10-di(2-naphthyl) anthracene (hereinafter referred to as DNA) is formed to a film thickness of 40 nm instead of CzPA (hereinafter referred to as an element E) are manufactured.

Initial properties of the element C, the element D, and element E are shown in Table 2.

TABLE 2

Original properties of elements C, D and E

| Element | Light emitting Starting voltage (V) | Voltage at 500 $Cd/m^2$ (V) | Chromaticity (x, y) | Efficiency at 500 $Cd/m^2$ (Cd/A) |
|---|---|---|---|---|
| C | 5.4 | 9.6 | (0.15, 0.13) | 3.42 |
| D | 5.2 | 10.2 | (0.15, 0.10) | 1.81 |
| E | 5.6 | 10.2 | (0.16, 0.17) | 2.94 |

Whichever of the elements A or B provides excellent chromaticity as a blue color light emitting element; however, the current efficiency of the element C is greatly increased. Accordingly, the current efficiency of the element CzPA is higher compared with BuDNA or DNA.

Figure 31:
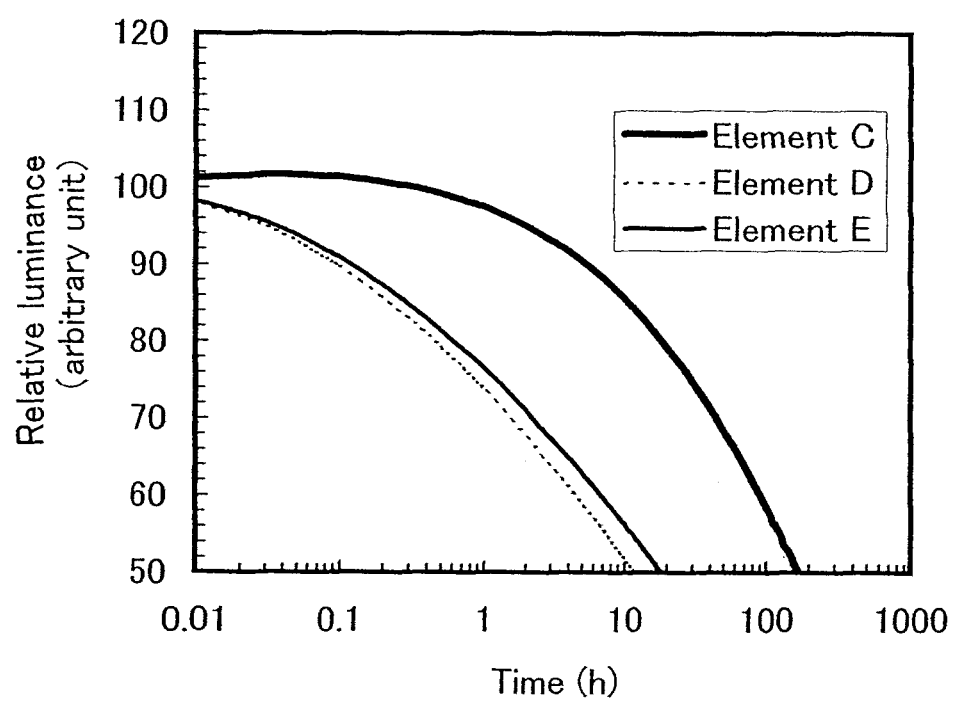
FIG. 31 shows a reliability measurement result of an element C, an element D, and an element E.

A reliability test result of those elements are shown in FIG. 31. The test conditions are set as follows: the initial luminance is set at 500 cd/A, the element is driven by constant current, and the change of the luminance over time is measured. The half-life of the elements D and E is less than 20 hours; meanwhile, that of the element C is over 100 hours. Thus, it is found that the light emitting element using CzPA which is an anthracene derivative of the present invention which has an anthracene skeleton and a carbazolyl skeleton is highly reliable.

EXAMPLE 7

In this example, as a host of a dope-type element (which has a light emitting layer having a host and a guest), as with the anthracene derivative of the present invention, an anthracene derivative in which an anthracene skeleton and a carbazolyl skeleton are introduced, and a phenyl group is introduced into 9 and 10 positions of the anthracene skeleton is used; thus, the reliability of the element can be improved.

The element was manufactured in the same manner as Example 6. DNTPD was formed to 50 nm as a hole injection layer over ITSO which is a first electrode, and NPB was formed thereover to 10 nm as a hole transporting material. Next, a light emitting layer was formed to 40 nm. The structure of the light emitting layer may have a structure of an element F using a co-deposited film of CzPA which is an anthracene derivative of the present invention and 2,5,8,11-tetra-t-butylperylene (hereinafter referred to as TBP), or a structure of an element G using a co-deposited film of t-BuDNA and TBP. Weight ratios of TBP and CzPA or t-BuDNA which is a host was both 1:0.01. Alq was formed to 20 nm as an electron transporting layer, and calcium fluoride ($CaF_2$) was formed to 1 nm as an electron injection layer, and Al was formed to 200 nm as a second electrode over the light emitting layer of those.

The properties of the elements are shown in Table 3.

TABLE 3

Original properties of elements F and G

| Element | Light emitting Starting voltage (V) | Voltage at 500 Cd/$m^2$ (V) | Chromaticity (x, y) | Efficiency at 500 Cd/$m^2$ (Cd/A) |
|---|---|---|---|---|
| F | 4.0 | 6.8 | (0.16, 0.27) | 5.01 |
| G | 3.4 | 6.0 | (0.15, 0.24) | 4.33 |

It is found that whichever of the elements achieved relatively high efficiency.

Figure 32:
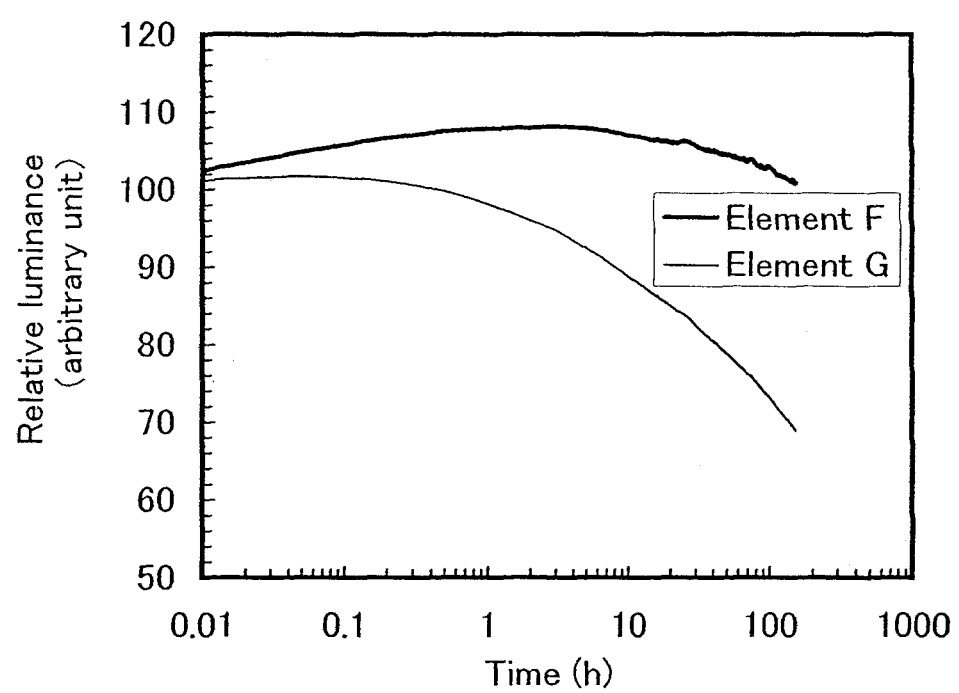
FIG. 32 shows a reliability measurement result of an element F and an element G.

Reliability test results of the elements are shown in FIG. 32. The test condition was as follows: the initial luminance was set at 500 cd/A, the elements were driven by constant current, and the change of luminance over time was measured. In the element G, 10% luminance deterioration was approximately for approximately 8 hours, and the expected half-life is within approximately several hundred hours. Meanwhile, as to the element F, although drive the luminance slightly increases in an early period of driving, it shows substantially almost no deterioration of luminance after 100 hours. The expected life half-life is about 5200 hours. Thus, CzPA according to the present invention in which an anthracene group and a carbazolyl skeleton are included, and one carbazolyl group for one anthracene skeleton is included is used as a host in a light emitting layer, the reliability can be improved.

EXAMPLE 8

In this example, Example 7, as a host of a dope-type element, an anthracene derivative according to the invention in which an anthracene skeleton and a carbazolyl skeleton are introduced, and a phenyl group is introduced into 9 and 10 positions of an anthracene skeleton is used; thus, the reliability of the element can be improved.

The element was manufactured in the same manner as Example 7, DNTPD was formed to 50 nm as a hole injection layer, NBP was formed thereover to 10 nm as a hole transporting material over ITSO which is a first electrode. Next, a light emitting layer was formed thereover to a 40 nm. The structure for the light emitting layer is a structure of an element H using a co-deposited film of CzPA which is an anthracene derivative of the invention and 9,10-bis{4-[N-(4-diphenylamino)phenyl-N-phenyl]aminophenyl}-2-t-butylanthracene (hereinafter referred to as DPABPA), and the structure of an element I using a co-deposited film of t-BuDNA and DPABPA. Weight ratios of DPABPA and CzPA or t-BuDNA which is a host was both 1:0.05. Alq was formed to 20 nm as an electron transporting layer, and calcium fluoride ($CaF_2$) was formed to 1 nm as an electron injection layer, and Al was formed to 200 nm as a second electrode over the light emitting layer of those.

The properties of the elements are shown in Table 4.

TABLE 4

Original properties of elements H and I

| Element | Light emitting Starting voltage (V) | Voltage at 500 Cd/$m^2$ (V) | Chromaticity (x, y) | Efficiency at 500 Cd/$m^2$ (Cd/A) |
|---|---|---|---|---|
| H | 3.6 | 7.0 | (0.22, 0.43) | 9.06 |
| I | 3.2 | 6.8 | (0.19, 0.38) | 9.40 |

Whichever of the elements can achieve relatively high efficiency.

Figure 33:
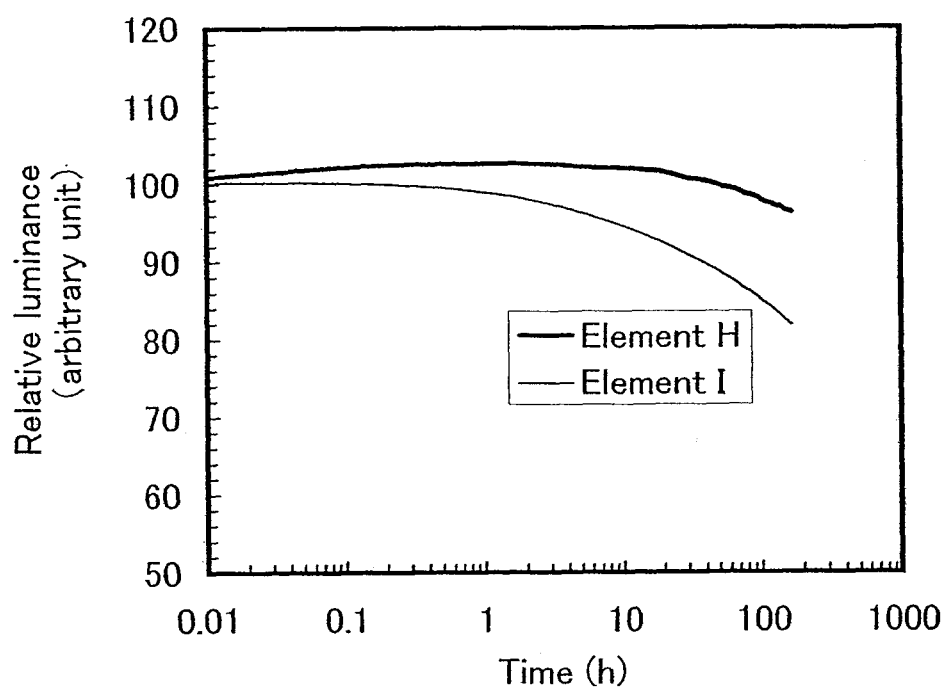
FIG. 33 shows a reliability measurement result of an element H and an element I.

Reliability test results of the elements are shown in FIG. 33. The test condition was as follows: the initial luminance was set at 500 cd/A, the elements were driven by constant current, and the change of luminance over time was measured. In the element I, 10% luminance deterioration was approximately for approximately 40 hours, and the expected half-life is within approximately 1000 hours. Meanwhile, as to the element H, it shows almost no deterioration of luminance even after 100 hours. The expected life half-life is about 5200 hours. Thus, CzPA according to the present invention in which a phenyl group is directly introduced into an anthracene skeleton, and one carbazolyl group for one anthracene skeleton is included is used as a host in a light emitting layer, adequate reliability can be achieved.

EXAMPLE 9

In this example, a manufacturing method of an element of DPCzPA proposed as an anthracene derivative in the present invention, and the properties thereof will be described.

The element was manufactured in the same manner as Example 7, CuPc was formed to 20 nm as a hole injection layer, BSPB was formed thereover to 40 nm as a hole transporting material over ITSO which is a first electrode. Next, DPCzPA was formed thereover to a 40 nm as a light emitting layer. Alq was formed to 20 nm as an electron transporting layer, and calcium fluoride ($CaF_2$) was formed to 1 nm as an electron injection layer, and Al was formed to 200 nm as a second electrode over the light emitting layer of those.

The properties of the element is shown in Table 5. Excellent chromaticity as blue can be provided.

TABLE 5

Original properties of element using DPCzPA

| Light emitting Starting voltage (V) | Voltage at 500 Cd/$m^2$ (V) | Chromaticity (x, y) | Efficiency at 500 Cd/$m^2$ (Cd/A) |
|---|---|---|---|
| 6.8 | 11.2 | (0.15, 0.10) | 3.05 |

EXAMPLE 10

In this example, as to a dope-type element using CzPA as an anthracene derivative proposed in the present invention, a manufacturing method of an element using a co-deposited film of molybdenum oxide and NPB as a hole injection layer and the characteristics thereof will be described The element was manufactured in the same manner as Example 7. A co-deposited film of NBP and molybdenum oxide was formed as a hole injection layer over ITSO which is a first electrode. The film thickness was 50 nm and the weight ratio of NPB and molybdenum oxide was 4:1. NPB is formed to 10 nm as a hole transporting material over the layer. Next, a co-deposited film of CzPA and TBP or CzPA and DPABPA was formed as a light emitting layer. The weight ratio of CzPA and TBP was 1:0.01 and the weight ratio between CzPA and DPABPA was 1:0.05. An element in using the CzPA and TBP is an element J, and an element using a co-deposited film of CzPA and DPABPA is an element K. Alq was formed to 20 nm as an electron transporting layer, and calcium fluoride ($CaF_2$) was formed to 1 nm as an electron injection layer, and Al was formed to 200 nm as a second electrode over the light emitting layer of those.

The properties of the elements are shown in Table 6.

TABLE 6

| | Original properties of elements J and K | | | |
|---|---|---|---|---|
| Element | Light emitting Starting voltage (V) | Voltage at 500 $Cd/m^2$ (V) | Chromaticity (x, y) | Efficiency at 500 $Cd/m^2$ (Cd/A) |
| J | 3.8 | 6.4 | (0.16, 0.25) | 3.53 |
| K | 3.4 | 6.6 | (0.22, 0.40) | 6.78 |

Efficient light emission was obtained in whichever of the elements; thus, CzPA was found to suitably serve as a host of a light emitting layer.

EXAMPLE 11

In this example, as to a dope-type element using CzPA as an anthracene derivative proposed in the present invention, a method of manufacturing an element using 9,10-bis{4-[N-(N-phenyl-3-carbazolyl)-N-phenyl]aminophenyl}-2-t-butylanthracene (hereinafter referred to as PCABPA), and 9,10-bis{4-[N-(4-carbazolyl)phenyl-N-phenyl]aminophenyl}-2-t-butylanthracene (hereinafter referred to as YGABPA) as dopants the properties thereof.

The element was manufactured in the same manner as Example 7. DNTPD was formed to 50 nm as a hole injection layer, and NBP was formed to 10 nm to form a stack over ITSO which is a first electrode. Next, a co-deposited film of CzPA and PCABPA or CzPA and YGABPA was formed to a film thickness of 40 nm as a light emitting layer. The weight ratio of CzPA and PCABPA was 1:0.05 and the weight ratio between CzPA and YGABPA was 1:0.1. An element in using the CzPA and PCABPA is an element L, and an element using a co-deposited film of CzPA and YGABPA is an element M. Alq was formed to 20 nm as an electron transporting layer, and calcium fluoride ($CaF_2$) was formed to 1 nm as an electron injection layer, and Al was formed to 200 nm as a second electrode over the light emitting layer of those.

The properties of the elements are shown in Table 7.

TABLE 7

| | Original properties of elements L and M | | | |
|---|---|---|---|---|
| Element | Light emitting Starting voltage (V) | Voltage at 500 $Cd/m^2$ (V) | Chromaticity (x, y) | Efficiency at 500 $Cd/m^2$ (Cd/A) |
| L | 3.0 | 4.6 | (0.17, 0.35) | 10.5 |
| M | 3.6 | 5.2 | (0.15, 0.24) | 6.81 |

Efficient light emission was obtained in whichever of the elements; thus, CzPA was found to suitably serve as a host of a light emitting layer.

EXAMPLE 12

In this example, as to a dope-type element using CzPA as an anthracene derivative proposed in the present invention, a method of manufacturing an element using 9,10-bis{4-[N-(N-phenyl-3-carbazolyl)-N-phenyl]aminophenyl}-2-t-butylanthracene (hereinafter referred to as PCABPA), and 9,10-bis {4-[N-(4-carbazolyl)phenyl-N-phenyl]aminophenyl}-2-t-butylanthracene (hereinafter referred to as YGABPA) as dopants and using a co-deposited film of molybdenum oxide and NPB for a hole injection layer, and the properties thereof.

The element was manufactured in the same manner as Example 7. A co-deposited film of NBP and molybdenum oxide was formed as a hole injection layer over ITSO which is a first electrode. The film thickness was 50 nm and the weight ratio of NPB and molybdenum oxide was 4:1. NPB is formed to 10 nm as a hole transporting material over the layer. Next, a co-deposited film of CzPA and PCABPA or CzPA and YGABPA was formed to a film thickness of 40 nm as a light emitting layer. The weight ratio of CzPA and PCABPA was 1:0.05 and the weight ratio between CzPA and YGABPA was 1:0.1. An element in using the CzPA and PCABPA is an element N, and an element using a co-deposited film of CzPA and YGABPA is an element O. Alq was formed to 20 nm as an electron transporting layer, and calcium fluoride ($CaF_2$) was formed to 1 nm as an electron injection layer, and Al was formed to 200 nm as a second electrode over the light emitting layer of those.

The properties of the elements are shown in Table 8.

TABLE 8

| | Original properties of elements N and O | | | |
|---|---|---|---|---|
| Element | Light emitting Starting voltage (V) | Voltage at 500 $Cd/m^2$ (V) | Chromaticity (x, y) | Efficiency at 500 $Cd/m^2$ (Cd/A) |
| N | 3.0 | 4.4 | (0.17, 0.31) | 7.99 |
| O | 3.4 | 5.2 | (0.16, 0.21) | 4.25 |

Efficient light emission was obtained in whichever of the elements; thus, CzPA was found to suitably serve as a host of a light emitting layer. Further, as compared with Example 11 in which DNTPD was used as a hole injection layer, chromaticity of blue was improved.

EXAMPLE 13

In this example, as to a dope-type element using CzPA and CzAlPA as anthracene derivatives proposed in the present invention, a method of manufacturing a light emitting element using CzPA as a host, and using CzAlPA as a dopant and the properties thereof will be described.

The element was manufactured in the same manner as Example 7. DNTPD was formed to a film thickness of 50 nm as a hole injection layer over ITSO which is a first electrode. NBP was formed thereover to 10 nm as a hole transporting material. Next, a co-deposited film of CzPA and CzAlPA was formed to a film thickness of 40 nm as a light emitting layer. The weight ratio of CzPA and CzAlPA was 1:0.10. Alq was formed to 10 nm or 20 nm as an electron transporting layer, and a co-deposited film of Alq and lithium (Alq: Li=1:0.01) with a thickness of 10 nm, calcium fluoride ($CaF_2$) was formed to 1 nm as an electron injection layer, and Al was formed to 200 nm as a second electrode over the light emitting layer of those. An element in which Alq was formed to 10 nm as an electron transporting layer and a co-deposited film of Alq and lithium as an electron injection layer is named as an element P1, and an element using 20 nm of Alq as an electron injection layer and using calcium fluoride as an electron transporting layer is named as an element P2.

The properties of the elements are shown in Table 9.

TABLE 9

Original properties of elements P1 and P2

| Element | Light emitting Starting voltage (V) | Voltage at 500 $Cd/m^2$ (V) | Chromaticity (x, y) | Efficiency at 500 $Cd/m^2$ (Cd/A) |
|---|---|---|---|---|
| P1 | 3.6 | 6.4 | (0.16, 0.19) | 3.71 |
| P2 | 4.0 | 7.6 | (0.16, 0.19) | 3.18 |

Efficient light emission was obtained in whichever of the elements; thus, CzPA was found to suitably serve as a host of a light emitting layer. Further, CzAlPA was found to suitably serve as a dopant of the light emitting layer.

EXAMPLE 14

In this example, a method of manufacturing a light emitting element using CzAlPA as an anthracene derivative proposed in the present invention and the properties thereof will be described.

The element was manufactured in the same manner as Example 7. DNTPD was formed to a film thickness of 50 nm as a hole injection layer. NBP was formed thereover to 10 nm as a hole transporting material. Next, CzAlPA was formed to a film thickness of 40 nm as a light emitting layer. Alq was formed to 10 nm as an electron transporting layer, and a 10 nm co-deposited film of Alq and lithium (Alq: Li=1:0.01) and Al was formed to 200 nm as a second electrode over the light emitting layer of those. The element is named as an element Q.

The properties of the elements are shown in Table 10.

TABLE 10

Original properties of element Q

| Element | Light emitting Starting voltage (V) | Voltage at 500 $Cd/m^2$ (V) | Chromaticity (x, y) | Efficiency at 500 $Cd/m^2$ (Cd/A) |
|---|---|---|---|---|
| Q | 3.6 | 5.4 | (0.22, 0.32) | 3.31 |

Efficient light emission was obtained in whichever of the elements; thus, CzPA was found to suitably serve as a host of a light emitting layer.

EXAMPLE 15

In this example, as to a dope-type element using DPCzPA as an anthracene derivative proposed in the present invention, a method of manufacturing a light emitting element using DPCzPA as a host, and using TBP as a dopant and the properties thereof will be described.

The element was manufactured in the same manner as Example 7. CuPc was formed to a film thickness of 20 nm as a hole injection layer. NBP or BSPB was formed thereover to 40 nm as a hole transporting material. Next, a co-deposited film of DPCzPA and TBP was formed to a film thickness of 40 nm as a light emitting layer. The weight ratio of DPCzPA and TBP was 1:0.01. Alq was formed to 10 nm or 20 nm as an electron transporting layer, and a co-deposited film of Alq and lithium (Alq: Li=1:0.01), calcium fluoride ($CaF_2$) was formed to 1 nm as an electron injection layer, and Al was formed to 200 nm as a second electrode over the light emitting layer of those. An element in which NPB as a hole transporting layer is denoted by R1 and an element in which BSPB is used is denoted by R2.

The properties of the element are shown in Table 11.

TABLE 11

Original properties of elements R1 and R2

| Element | Light emitting Starting voltage (V) | Voltage at 500 $Cd/m^2$ (V) | Chromaticity (x, y) | Efficiency at 500 $Cd/m^2$ (Cd/A) |
|---|---|---|---|---|
| R1 | 5.4 | 9.8 | (0.15, 0.25) | 4.88 |
| R2 | 5.5 | 10.2 | (0.15, 0.26) | 4.63 |

Efficient light emission was obtained in whichever of the elements; thus, CzPA was found to suitably serve as a host of a light emitting layer.

EXAMPLE 16

In this example, as to a dope-type element using DPCzPA as an anthracene derivative proposed in the present invention, a method of manufacturing a light emitting element using DPCzPA as a host, and using PCABPA as a dopant and the properties thereof will be described.

The element was manufactured in the same manner as Example 7. DNTPD having a film thickness of 50 nm or CuPc having a film thickness of 20 nm as a hole injection layer over ITSO which is a first electrode. NBP was formed thereover to 10 nm as a hole transporting material. Next, a co-deposited film of DPCzPA and PCABPA was formed to a film thickness of 40 nm as a light emitting layer. The weight ratio of DPCzPA and PCABPA was 1:0.04. Alq was formed to 10 nm as an electron transporting layer, and a co-deposited film of Alq and lithium (Alq: Li=1:0.01) having a thickness of 10 nm, calcium fluoride ($CaF_2$) was formed to 1 nm as an electron injection layer, and Al was formed to 200 nm as a second electrode over the light emitting layer of those. An element using DNTPD as a hole injection layer is denoted by S1, and an element using CuPc is denoted by S2.

The properties of the elements are shown in Table 12.

TABLE 12

Original properties of elements S1 and S2

| Element | Light emitting Starting voltage (V) | Voltage at 500 $Cd/m^2$ (V) | Chromaticity (x, y) | Efficiency at 500 $Cd/m^2$ (Cd/A) |
|---|---|---|---|---|
| S1 | 3.7 | 5.5 | (0.17, 0.32) | 9.87 |
| S2 | 4.0 | 6.4 | (0.17, 0.31) | 10.11 |

Efficient light emission was obtained in whichever of the elements; thus, DPCzPA was found to suitably serve as a host of a light emitting layer.

EXPLANATION OF REFERENCE

50 substrate, 52 semiconductor layer, 53 gate insulating layer, 54 gate electrode, 59 insulating film (hydride film), 60 interlayer insulating layer, 63 interlayer insulating layer, 64 electrode, 65 partition wall, 66 layer, 66 light emitting stack, 67 electrode, 70 thin film transistor, 88 resin, 89 desiccant, 90 polarizing plate, 91 protective film, 93 light emitting element, 94 counter substrate, 100 insulator, 101 electrode, 102 layer, 103 electrode, 51*a* base insulating layer, 51*b* base insulating layer, 61*a* connection portion, 61*b* wiring, 1401 switching TFT, 1402 capacitor, 1403 driving TFT, 1404 current control TFT, 1405 light emitting element, 1406 TFT, 1410 signal line, 1411 power source line, 1412 power source line, 1414 scan line, 1415 scan line, 1500 pixel area, 1554 wiring, 1561 diode, 2001 case, 2003 display area, 2004 speaker portion, 2101 main body, 2102 chassis, 2103 display area, 2104 audio input portion, 2105 audio output portion, 2106 operation key, 2108 antenna, 2201 main body, 2202 case, 2203 display area, 2204 keyboard, 2205 external connection portion, 2206 pointing mouse, 2301 main body, 2302 display area, 2303 switch, 2304 operation key, 2305 infrared port, 2401 case, 2402 display area, 2403 speaker portion, 2404 operation key, 2405 storage medium portion, 4001 substrate, 4002 pixel area, 4003 signal conductor driver circuit, 4004 scan line driver circuit, 4005 sealing material, 4006 counter substrate, 4007 filler, 4008 thin film transistor, 4010 thin film transistor, 4011 light emitting element, 4014 wiring, 4015 wiring, 4016 connection terminal, 4018 flexible printed circuit (FPC), 4019 anisotropic conductive film

What is claimed is:

1. A composition comprising:
   an anthracene derivative represented by any one of general formulae (2) and (3):

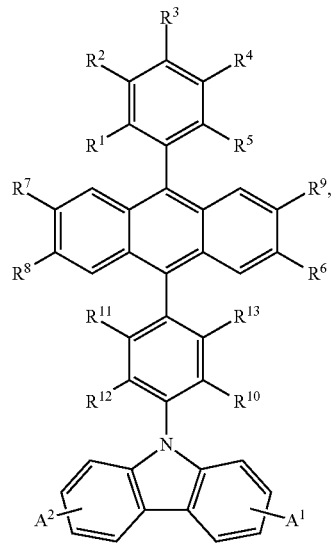

(2)

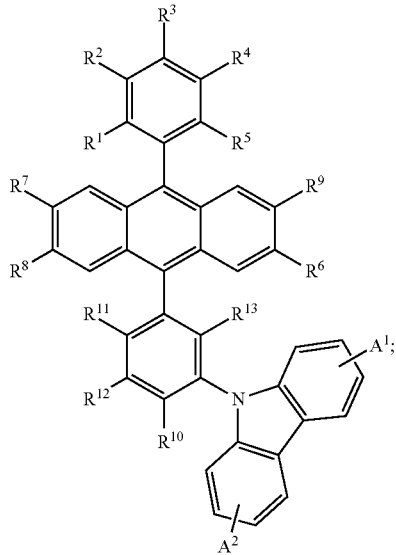

(3)

and
   a solvent,
   wherein:
   $R^1$ to $R^{13}$ are hydrogen; and
   $A^1$ and $A^2$ are independently hydrogen, an alkyl group having 1 to 6 carbon atoms, a substituted or unsubstituted aryl group having 6 to 14 carbon atoms, or a substituted or unsubstituted diarylamino group.

2. The composition according to claim 1, wherein $A^1$ is a substituted or unsubstituted diarylamino group and $A^2$ is hydrogen or a substituted or unsubstituted diarylamino group.

3. The composition according to claim 1, wherein the anthracene derivative is represented by a general formula (4):

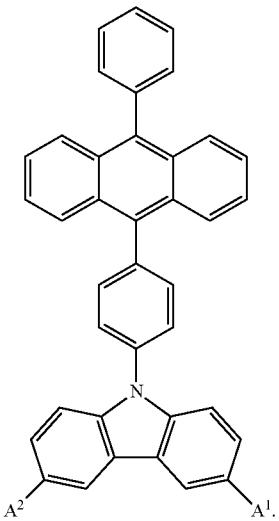

(4)

4. The composition according to claim 1, wherein $A^1$ and $A^2$ each are hydrogen.

5. A method of fabricating a light-emitting element comprising:
forming a first electrode;
forming a layer over the first electrode, the layer containing an anthracene derivative; and
forming a second electrode over the layer,
wherein the anthracene derivative is represented by any one of general formulae (2) and (3):

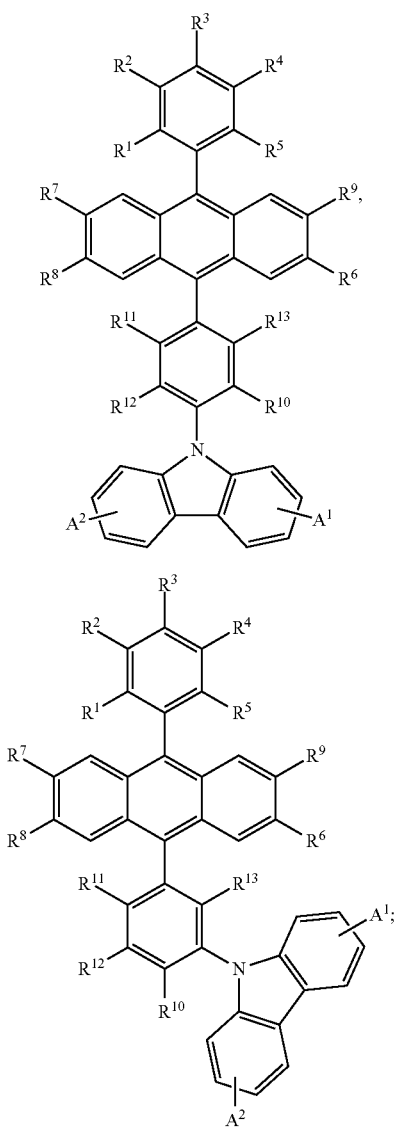

and wherein:

$R^1$ to $R^{13}$ are hydrogen; and $A^1$ and $A^2$ are independently hydrogen, an alkyl group having 1 to 6 carbon atoms, a substituted or unsubstituted aryl group having 6 to 14 carbon atoms, or a substituted or unsubstituted diarylamino group.

6. The method according to claim 5, wherein $A^1$ is a substituted or unsubstituted diarylamino group and $A^2$ is hydrogen or a substituted or unsubstituted diarylamino group.

7. The method according to claim 5, wherein the anthracene derivative is represented by a general formula (4):

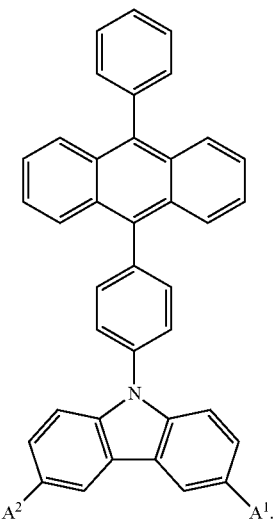

8. The method according to claim 5, wherein $A^1$ and $A^2$ each are hydrogen.

9. The method according to claim 5, wherein the layer is formed by a method selected from an ink-jet method, a spin coating method, and a dip coating method.

10. The method according to claim 5, wherein the layer consists of the anthracene derivative.

11. The method according to claim 5, wherein the layer further comprises a dopant.

12. The method according to claim 5, further comprising a step of forming a functional layer between the first electrode and the second electrode.

* * * * *

UNITED STATES PATENT AND TRADEMARK OFFICE
CERTIFICATE OF CORRECTION

| PATENT NO. | : 8,603,647 B2 |
|---|---|
| APPLICATION NO. | : 13/609956 |
| DATED | : December 10, 2013 |
| INVENTOR(S) | : Sachiko Kawakami et al. |

It is certified that error appears in the above-identified patent and that said Letters Patent is hereby corrected as shown below:

In the Specification

Column 27, line 28, replace the compound at paragraph (35) with the following:

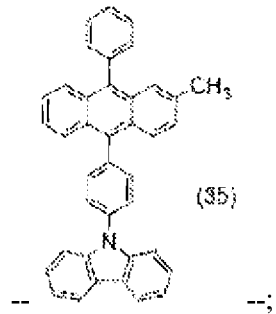

Column 83, lines 40-65, replace the schemes with the following:

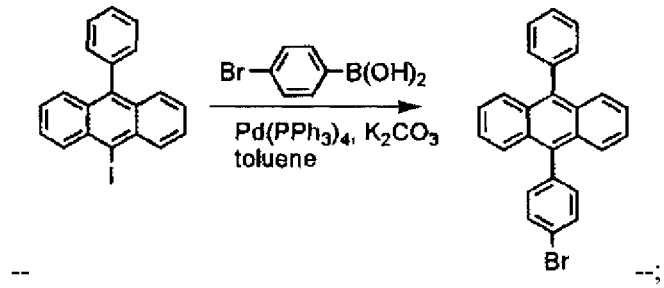

Signed and Sealed this
Ninth Day of September, 2014

Michelle K. Lee
*Deputy Director of the United States Patent and Trademark Office*

CERTIFICATE OF CORRECTION (continued)
U.S. Pat. No. 8,603,647 B2

Column 84, lines 23-57, replace the schemes with the following:

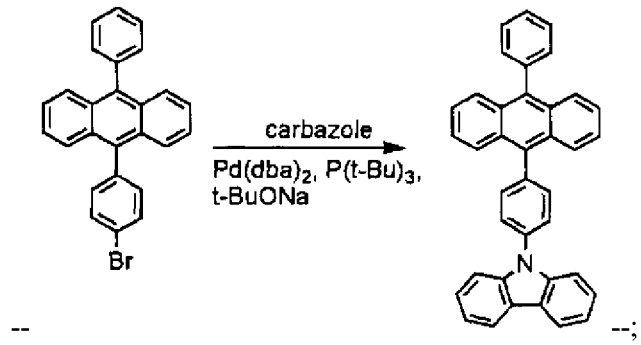

--  --;

Column 86, line 58 through Column 87, line 39, replace the schemes with the following:

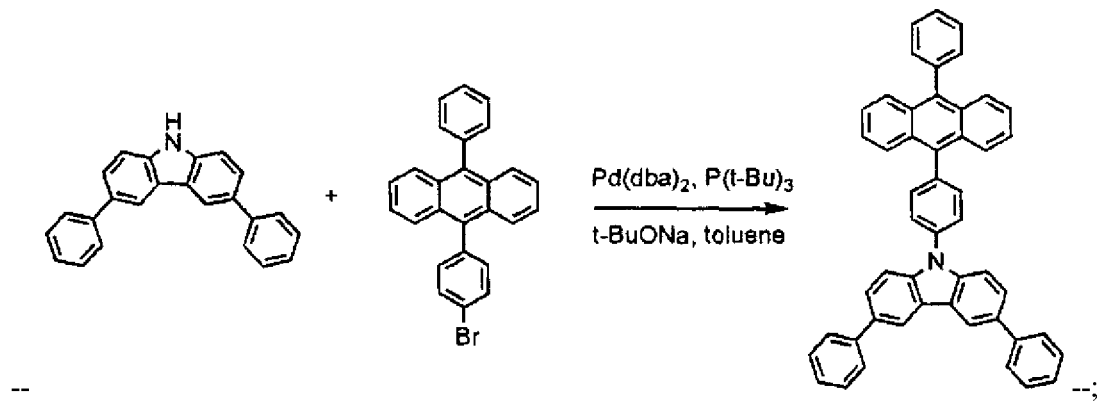

--  --;

Column 89, line 42 through Column 90, line 24, replace the schemes with the following:

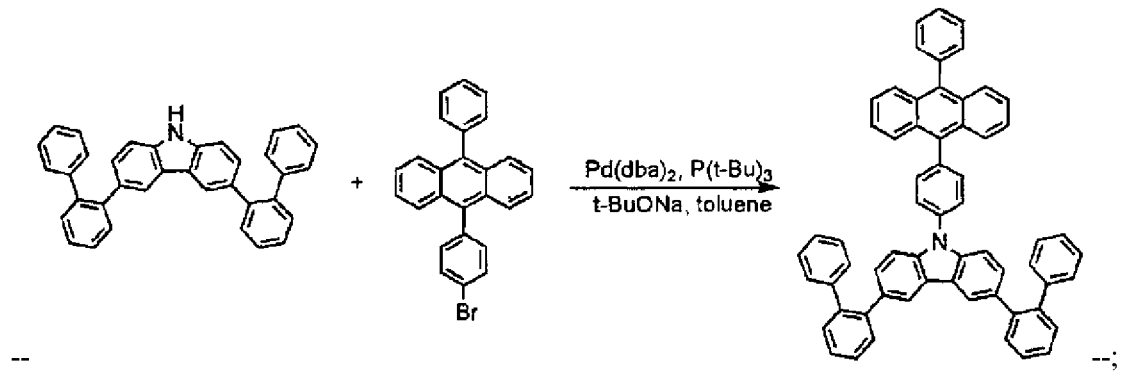

--  --;

CERTIFICATE OF CORRECTION (continued)

Column 94, lines 1-52, replace the schemes with the following:

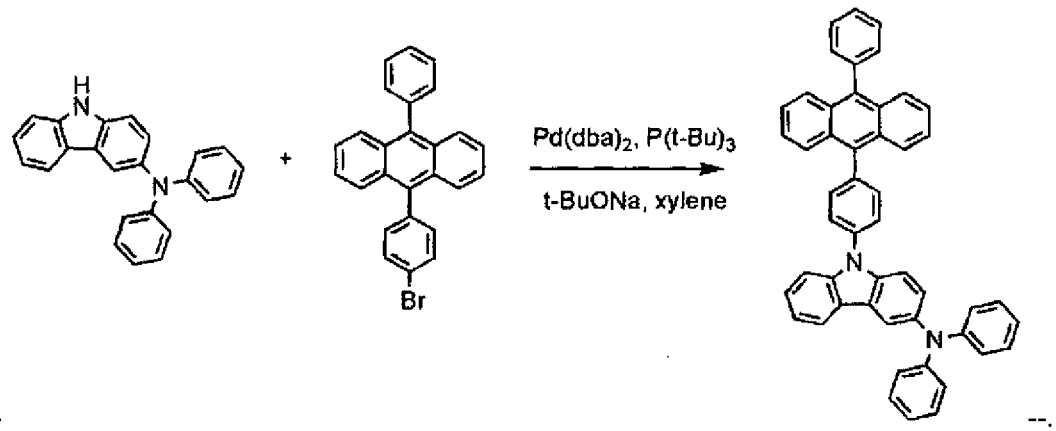

-- --.